US008916363B2

(12) United States Patent
Gusakov et al.

(10) Patent No.: US 8,916,363 B2
(45) Date of Patent: *Dec. 23, 2014

(54) CONSTRUCTION OF HIGHLY EFFICIENT CELLULASE COMPOSITIONS FOR ENZYMATIC HYDROLYSIS OF CELLULOSE

(75) Inventors: Alexander V. Gusakov, Moscow (RU); Tatyana N. Salanovich, Moscow (RU); Alexey I. Antonov, Moscow (RU); Boris B. Ustinov, Tula (RU); Oleg N. Okunev, Moscow Region (RU); Richard P. Burlingame, Jupiter, FL (US); Mark A. Emalfarb, Jupiter, FL (US); Marco A. Baez, Jupiter, FL (US); Arkady P. Sinitsyn, Moscow (RU)

(73) Assignee: Dyadic International (USA), Inc., Jupiter, FL (US)

( * ) Notice: Subject to any disclaimer, the term of this patent is extended or adjusted under 35 U.S.C. 154(b) by 383 days.

This patent is subject to a terminal disclaimer.

(21) Appl. No.: 12/908,454

(22) Filed: Oct. 20, 2010

(65) Prior Publication Data

US 2011/0045546 A1    Feb. 24, 2011

Related U.S. Application Data

(63) Continuation of application No. 11/487,547, filed on Jul. 13, 2006, now Pat. No. 7,883,872, which is a continuation-in-part of application No. 10/394,568, filed on Mar. 21, 2003, now Pat. No. 7,399,627, which is a continuation of application No. 09/548,938, filed on Apr. 13, 2000, now Pat. No. 6,573,086, which is a continuation-in-part of application No. PCT/NL99/00618, filed on Oct. 6, 1999, which is a continuation-in-part of application No. PCT/EP98/06496, filed on Oct. 6, 1998, said application No. 11/487,547 is a continuation-in-part of application No. 09/284,152, filed as application No. PCT/US97/17669 on Sep. 30, 1997, now Pat. No. 7,892,812, and a continuation-in-part of application No. 08/731,170, filed on Oct. 10, 1996, now Pat. No. 5,811,381.

(51) Int. Cl.
C12P 19/22    (2006.01)
C12P 19/14    (2006.01)
C12N 9/42     (2006.01)

(52) U.S. Cl.
CPC .............. *C12N 9/2437* (2013.01); *C12P 19/14* (2013.01); *C12Y 302/01091* (2013.01); *C12N 9/244* (2013.01); *C12Y 302/01004* (2013.01); *C12Y 302/01006* (2013.01); *C12N 9/2445* (2013.01); *Y02E 50/16* (2013.01); *C12Y 302/01021* (2013.01)
USPC ................ 435/95; 435/98; 435/74; 435/209; 435/210

(58) Field of Classification Search
None
See application file for complete search history.

(56) References Cited

U.S. PATENT DOCUMENTS

| | | |
|---|---|---|
| 2,974,001 A | 3/1961 | Windblicher et al. |
| 3,844,890 A | 10/1974 | Horikoshi et al. |
| 3,966,543 A | 6/1976 | Cayle et al. |
| 4,081,328 A | 3/1978 | Skinner et al. |
| 4,435,307 A | 3/1984 | Barbesgaard et al. |
| 4,443,355 A | 4/1984 | Murata et al. |
| 4,462,307 A | 7/1984 | Wells |
| 4,479,881 A | 10/1984 | Tai |
| 4,486,533 A | 12/1984 | Lambowitz |
| 4,610,800 A | 9/1986 | Durham et al. |
| 4,661,289 A | 4/1987 | Parslow et al. |
| 4,816,405 A | 3/1989 | Timberlake et al. |
| 4,832,864 A | 5/1989 | Olson |
| 4,885,249 A | 12/1989 | Buxton et al. |
| 4,912,056 A | 3/1990 | Olson |
| 4,935,349 A | 6/1990 | McKnight et al. |
| 4,940,838 A | 7/1990 | Schilperoort et al. |
| 5,006,126 A | 4/1991 | Olson et al. |
| 5,120,463 A | 6/1992 | Bjork et al. |
| 5,122,159 A | 6/1992 | Olson et al. |
| 5,198,345 A | 3/1993 | Gwynne et al. |

(Continued)

FOREIGN PATENT DOCUMENTS

| | | |
|---|---|---|
| EP | 0239400 A2 | 9/1987 |
| EP | 0220016 B1 | 8/1991 |

(Continued)

OTHER PUBLICATIONS

Aleksenko et al. 1997. Autonomous Plasmid Replication in *Aspergillus nidulans*: AMA1 and MATE Elements. Fungal Genetics and Biology, vol. 21, pp. 373-387.

Aleksenko et al. 1996. Gene expression from replicating plasmids in *Aspergillus nidulans*. Mol. Gen. Genet. vol. 253, pp. 242-246.

(Continued)

*Primary Examiner* — Jim Ketter
(74) *Attorney, Agent, or Firm* — Keller Life Science Law, P.A.; Michael J. Keller

(57) ABSTRACT

This invention provides novel enzyme compositions using newly identified and isolated *C. lucknowense* enzymes, including CBH Ib CBH IIb, EG II, EG VI, β-glucosidase, and xylanase II in conjunction with previously identified enzymes CBH Ia, CBH IIa (previously described as Endo 43), and EG V. These enzyme compositions demonstrate an extremely high ability to convert lignocellulosic biomass (e.g., Avicel, cotton, Douglas fir wood pretreated by organosolv) to glucose. CBH Ia and IIb, which both have a cellulose-binding module (CBM) displayed a pronounced synergism with three major endoglucanases (EG II, EG V, EG VI) from the same fungus in hydrolysis of cotton as well as a strong synergy with each other. The enzyme compositions are effective in hydrolysis of the lignocellulosic biomass.

15 Claims, 38 Drawing Sheets

(56) References Cited

U.S. PATENT DOCUMENTS

| | | |
|---|---|---|
| 5,223,409 A | 6/1993 | Ladner et al. |
| 5,252,726 A | 10/1993 | Woldike |
| 5,290,474 A | 3/1994 | Clarkson et al. |
| 5,362,638 A | 11/1994 | Dahiya |
| 5,364,770 A | 11/1994 | Berka et al. |
| 5,436,158 A | 7/1995 | Takagi et al. |
| 5,457,046 A | 10/1995 | Woldike et al. |
| 5,464,763 A | 11/1995 | Schilperoort et al. |
| 5,503,991 A | 4/1996 | Gwynne et al. |
| 5,516,670 A | 5/1996 | Kuehnle et al. |
| 5,536,661 A | 7/1996 | Boel et al. |
| 5,565,332 A | 10/1996 | Hoogenboom et al. |
| 5,578,463 A | 11/1996 | Berka et al. |
| 5,602,004 A | 2/1997 | Jensen et al. |
| 5,604,129 A | 2/1997 | Jensen et al. |
| 5,605,793 A | 2/1997 | Stemmer |
| 5,627,052 A | 5/1997 | Schrader |
| 5,686,593 A | 11/1997 | Woldike et al. |
| 5,695,965 A | 12/1997 | Stuart et al. |
| 5,695,985 A | 12/1997 | Jensen et al. |
| 5,705,358 A | 1/1998 | Gouka et al. |
| 5,728,547 A | 3/1998 | Gwynne et al. |
| 5,753,477 A | 5/1998 | Chan |
| 5,763,192 A | 6/1998 | Kauffman et al. |
| 5,763,254 A | 6/1998 | Woldike et al. |
| 5,770,356 A | 6/1998 | Light, II et al. |
| 5,776,730 A | 7/1998 | Stuart |
| 5,780,279 A | 7/1998 | Matthews et al. |
| 5,783,385 A | 7/1998 | Treco et al. |
| 5,783,431 A | 7/1998 | Peterson et al. |
| 5,811,381 A | 9/1998 | Emalfarb et al. |
| 5,820,866 A | 10/1998 | Kappler et al. |
| 5,824,485 A | 10/1998 | Thompson et al. |
| 5,830,696 A | 11/1998 | Short |
| 5,834,191 A | 11/1998 | Radford et al. |
| 5,837,847 A | 11/1998 | Royer et al. |
| 5,849,541 A | 12/1998 | Vinci et al. |
| 5,858,657 A | 1/1999 | Winter et al. |
| 5,871,907 A | 2/1999 | Winter et al. |
| 5,879,921 A | 3/1999 | Cherry et al. |
| 5,939,250 A | 8/1999 | Short |
| 5,955,316 A | 9/1999 | Conneely et al. |
| 5,958,672 A | 9/1999 | Short |
| 5,965,384 A | 10/1999 | Boel et al. |
| 5,969,108 A | 10/1999 | McCafferty et al. |
| 5,989,814 A | 11/1999 | Frankel et al. |
| 6,015,707 A | 1/2000 | Emalfarb et al. |
| 6,017,731 A | 1/2000 | Tekamp-Olson et al. |
| 6,022,725 A | 2/2000 | Fowler et al. |
| 6,025,185 A | 2/2000 | Christensen et al. |
| 6,030,779 A | 2/2000 | Short |
| 6,046,021 A | 4/2000 | Bochner |
| 6,054,267 A | 4/2000 | Short |
| 6,057,103 A | 5/2000 | Short |
| 6,060,305 A | 5/2000 | Royer et al. |
| 6,066,493 A | 5/2000 | Shuster et al. |
| 6,121,034 A | 9/2000 | Laroche et al. |
| 6,174,673 B1 | 1/2001 | Short et al. |
| 6,184,026 B1 | 2/2001 | Shuster et al. |
| 6,518,042 B1 | 2/2003 | Borchert et al. |
| 6,573,068 B1 | 6/2003 | Milne Edwards et al. |
| 6,573,086 B1 | 6/2003 | Emalfrab et al. |
| 7,122,330 B2 | 10/2006 | Emalfarb et al. |
| 7,399,627 B2 | 7/2008 | Emalfarb et al. |
| 7,794,962 B2 | 9/2010 | Emalfarb et al. |
| 7,883,872 B2 * | 2/2011 | Gusakov et al. ............ 435/96 |
| 7,892,812 B2 | 2/2011 | Emalfarb et al. |
| 7,906,309 B2 | 3/2011 | Emalfarb et al. |
| 2003/0157595 A1 | 8/2003 | Emalfarb et al. |
| 2003/0176672 A1 | 9/2003 | Salceda et al. |
| 2004/0002136 A1 | 1/2004 | Emalfarb et al. |
| 2005/0191736 A1 | 9/2005 | Brown et al. |
| 2006/0005279 A1 | 1/2006 | Dotson et al. |
| 2006/0053514 A1 | 3/2006 | Wu et al. |
| 2006/0105361 A1 | 5/2006 | Rothstein et al. |
| 2006/0134747 A1 | 6/2006 | Baldwin et al. |
| 2006/0218671 A1 | 9/2006 | Brown et al. |
| 2007/0077630 A1 | 4/2007 | Harris et al. |
| 2009/0280105 A1 | 11/2009 | Gusakov et al. |

FOREIGN PATENT DOCUMENTS

| | | |
|---|---|---|
| EP | 0194276 B2 | 11/1993 |
| EP | 0239400 B1 | 8/1994 |
| EP | 0451216 B1 | 1/1996 |
| EP | 1022335 A1 | 7/2000 |
| EP | 0215594 B2 | 10/2003 |
| GB | 1368599 A | 10/1974 |
| GB | 2094826 A | 9/1982 |
| GB | 2289218 A | 11/1995 |
| JP | 50-132269 A | 10/1975 |
| JP | 11-304666 A | 11/1999 |
| WO | 8601533 A1 | 3/1986 |
| WO | 9100092 A1 | 1/1991 |
| WO | 9100920 A2 | 1/1991 |
| WO | 9109967 A1 | 7/1991 |
| WO | 9109968 A1 | 7/1991 |
| WO | 9213831 A1 | 8/1992 |
| WO | 9307277 A1 | 4/1993 |
| WO | 9311249 A1 | 6/1993 |
| WO | 9404673 A1 | 3/1994 |
| WO | 9413820 A1 | 6/1994 |
| WO | 9602563 A1 | 2/1996 |
| WO | 9629391 A1 | 9/1996 |
| WO | 9709438 A1 | 3/1997 |
| WO | 9713853 A1 | 4/1997 |
| WO | 9726330 A2 | 7/1997 |
| WO | 9727363 A1 | 7/1997 |
| WO | 9815633 A1 | 4/1998 |
| WO | 9932617 A2 | 7/1999 |
| WO | 9951756 A2 | 10/1999 |
| WO | 9964582 A2 | 12/1999 |
| WO | 9967639 A1 | 12/1999 |
| WO | 0000632 A1 | 1/2000 |
| WO | 0020555 A2 | 4/2000 |
| WO | 0050567 A1 | 8/2000 |
| WO | 0056893 A1 | 9/2000 |
| WO | 0056900 A2 | 9/2000 |
| WO | 0078997 A1 | 12/2000 |
| WO | 0109352 A2 | 2/2001 |
| WO | 0125468 A1 | 4/2001 |
| WO | 0179558 A1 | 10/2001 |
| WO | 2004031367 A2 | 4/2004 |

OTHER PUBLICATIONS

Archer et al. 1997. The Molecular Biology of Secreted Enzyme Production by Fungi. Critical Reviews in Biotechnology, vol. 17, No. 4, pp. 273-306.

Armesilla et al. 1994. CEL1: a novel cellulose binding protein secreted by *Agaricus bisporus* during growth on crystalline cellulose. FEMS Microbiol. Lett. vol. 116, pp. 293-300.

Arnau et al. 1991. Integrative transformation by homologous recombination in the zygomycete Mucor circinelloides. Mol. Gen. Genet., vol. 225, pp. 193-198.

Arnold et al. 1999. Directed evolution of biocatalysts. Current Opinion in chemical Biology, vol. 3, pp. 54-59.

Arnold et al. 1999. Encyclopedia of Bioprocess Technology: Fermentation, Biocatalysis, and Bioseparation. Flickinger et al., eds. John Wiley & Sons, pp. 971-987.

Asgeirsdottir et al. 1999. A Sandwiched-Culture Technique for Evaluation of Heterologous Protein Production in a Filamentous Fungus. Applied and Environmental Microbiology, vol. 65, No. 5, pp. 2250-2252.

Bajpai et al.1998. Deinking with Enzymes: A Review. TAPPI Journal. vol. 81, No. 12, pp. 111-117.

Benen et al. 2000. Characterization of *Aspergillus niger* Pectate Lyase A. Biochemistry, vol. 39, pp. 15563-15569.

Berges, T. et al. 1993. Cloning of an *Aspergillus niger* invertase gene by expression in *Trichoderma reesei*. Springer-verlag, vol. 24, pp. 53-59.

(56) References Cited

OTHER PUBLICATIONS

Bhatawadekar. 1983. Studies on Optimum Conditions of Dnzymatic Desizing of LTKP Sized Fabric by Cellulase—Steeping and Cellulase-Padding Methods. Journal of the Textile Association, May 1983, pp. 83-86.

Bretthauer et al. 1999. Glycosylation of *Pichia pastoris*-derived proteins. Biotechnol. Appl. Biochem., vol. 30, pp. 193-200.

Bukhtojarov et al. 2004. Cellulase Complex of the Fungus *Chrysosporium lucknowense*: Isolation and Characterization of Endoglucanases and Cellobiohydrolases. Biochemistry (Mosc), May 2004, vol. 69, No. 5, pp. 542-551 (Abstract).

Buxton et al. 1984. The transformation of mycelial spheroplasts of *Neurospora crassa* and the Attempted Isolation of an Autonomous Replicator. Mol. Gen. Genet, vol. 196, pp. 339-344.

Canevascini, G. et al. 1983. Fractionation and Identification of Cellulases and Other Extracellular Enzymes Produced by Sporotrichum (*Chrysosporium*) Thermophile During Growth on Cellulose or Cellobiose. Can. J. Microbiol., vol. 29, pp. 1071-1080.

Chakraborty et al. 1990. Transformation of Filamentous Fungi by Electroporation. Nucleic Acids Research, vol. 18, No. 22, p. 6637.

De Vries, R.P. and Visser, J., 2001. *Aspergillus* enzymes involved in degradation of plant cell wall polysaccharides. Microbiol. Mol. Biol. R., 65, 497-522.

Degroot et al., *Agrobacterium tumefaciens*-mediated transformation of filamentous fungi, Nature Biotechnology, vol. 16, pp. 839-842 (1998).

Deutsch et al., "Intron-exon structures of eukaryotic model organisms," Nucleic Acids Research, vol. 27, No. 15, pp. 3219-3228 (1999).

Ding et al. Cloning of multiple cellulose cDNAs from *Volvariella volvacea* and their differential expression during substrate colonization and fruiting. FEMS Microbiol. Lett 2006, vol. 263, pp. 207-213.

Eriksson, K. et al. Extracellular Enzyme System Utilized by the Fungus Sporotrichum Pulverulentum (*Chrysosporium lignorum*) for the Breakdown of Cellulose. 1, Separation, Purification, and Physico-Chemical Characterisation of Five Endo-1, 4-Beta-Glucanases. European Journal of Biochemistry, 1975, vol. 51, pp. 193-206.

Flanagan, P.W. et al. Physiological Groups of Decomposer Fungi on Tundra Plant Remains. In Soil Organisms and Decomposition in Tundra, A.J. Holding et al., Eds., Tundra Biome Steering Committee (Stockholm), 1974, pp. 159-181.

Foreman et al. Transcriptional Regulation of Biomass-Degrading Enzymes in the Filamentous Fungus *Trichoderma reesei*. J. Biol. Chem. 2003, vol. 278, pp. 31988-31997.

Gems et al., "An 'instant gene bank' method for gene cloning by mutant complementation," Mol. Gen. Genet, vol. 242, pp. 467-471 (1994).

Gems et al., "Co-transformation with autonomously-replicating helper plasmids facilitates gene cloning from an *Aspergillus nidulans* gene library," Curr. Genet., vol. 24, pp. 520-524 (1993).

Gordillo et al. *Penicillium purpurogenum* Produces a Family 1 Acetyl Xylan Esterase Containing a Carbohydrate-Binding Module: Characterization of the Protein and Its Gene. Mycol. Res., 2006, vol. 110, p. 1129.

Goudar et al. Influence of microbial concentration on the rheology of non-Newtonian fermentation broths. Appl. Microbiol. Biiotechnol. 1999, vol. 51, pp. 310-315.

Gunf-Fusox, accession No. p46239, Nov. 1, 1995, P.O. Sheppard et al. The Use of Conserved Cellulase Family-Specific Sequences to Clone Cellulase Homologue cDNAs from *Fusarium oxysporum*.

Gusakov, A.V. et al. Design of Highly Efficient Cellulase Mixtures for Enzymatic Hydrolysis of Cellulose. Biotechnol. Bioeng., 2007, vol. 97, No. 5, pp. 1028-1038.

Gusakov, A.V. et al. Purification, Cloning and Characterization of Two Forms of Thermostable and Highly Active Cellobiohydrolase I (Cel7A) Produced by the Industrial Strain of *Chrysosporium lucknowense*. Enzyme Microb. Technol. 2005, vol. 36, pp. 57-69.

Gusakov, A.V. Microassays to Control the Results of Cellulase Treatment of Denim Fabrics. Textile Chemist and Colorist and American Dyestuff Reporter, 2000, vol. 32, No. 5, pp. 42-47.

Hahn-Hagerdal et al. Bio-ethanol—The Fuel of Tomorrow from the Residues of Today. Trends in Biotechnology, 2006, vol. 24, No. 12, pp. 549-556.

Harmsen Martin C. et al. 1992. Sequence Analysis of the Glyceraldehyde-3-phosphate dehydrogenase genes from the basidiomycetes *Schizopyllum commune, Phanerochaete chrysosporium* and *Agaricus bisporus*. Current Genetics, vol. 22, No. 6, pp. 447-454.

Hong et al. Unusual hydrophobic linker region of B-glucosidase (BGLII) from *Thermoascus aurantiacus* is required for hyper-activation by organic solvents. Applied Microbiol. Biotechnol., 2006, vol. 73, pp. 80-88.

Huertas-Gonzalez et al. Cloning and characterization of pl1 encoding an in planta-secreted pectate lyase of *Fusarium oxysporum*. Curr Genet, 1999, vol. 35, pp. 36-40.

Hurst, J.L. et al Association between *Chrysosporium pannorum* and *Mucor hiemalis* in *Poa flabellata* Litter. Trans. Br. Mycol. Soc., 1983, vol. 81, No. 1, pp. 151-153.

Iikura, H. et al. Cloning of a Gene Encoding a Putative Xylanase with a Cellulose-Binding Domain from *Humicola grisea*. Bioscience Biotechnology and Biochemistry, 1997, vol. 61, No. 9, pp. 1593-1595.

Janeckova et al. Ceska Mykologie (1977), vol. 331, No. 4, pp. 206-213 (Abstract).

Jeenes et al., "Heterologous Protein Production by Filamentous Fungi," Biotechnology & Genetic Engineering Reviews, vol. 9, pp. 327-367 (1991).

Johnstone et al. Cloning an *Aspergillus nidulans* developmental gene by transformation. EMBO J., 1985, vol. 4, pp. 1307-1311.

Joo et al., "A high-throughput digital imaging screen for the discovery and directed evolution of oxygenases," Chemistry & Biology, vol. 6, pp. 699-706 (1999).

Judelson et al., "Transformation of the Oomycete Pathogen, *Phytophthora infestans*," Molecular Plant-Microbe Interactions, vol. 4, No. 6, pp. 602-607 (1991).

Kauppinen et al. Molecular Cloning and Characterization of a Rhamnogalacturonan Acetylesterase from *Aspergillus aculeatus*. J. Biol Chem, 1995, vol. 270, p. 27172-27178.

Kormelink F.J.M. et al. Mode of Action of the Xylan-Degrading Enzymes from *Aspergillus awamori* on Alkali-Extractable Cereal Arabinoxylans. Carbohydr. Res, 1993, vol. 249, pp. 355-367.

Kormelink et al. Purification and Characterization of Three Endo-(1,4)-B-xylanases and one B-xylosidase from *Aspergillus awamori*. J. Biotechnol. 1993, vol. 27, pp. 249-265.

Kotake et al. Molecular cloning and expression in *Escherichia coli* of a Trichoderma viride endo-B-(1-6)-galactanase gene. Biochem J.., 2004, vol. 377, pp. 749-755.

Kramer et al. Insect Chitinases: Molecular Biology and Potential Uses as Biopesticides. Insect Biochem Mol Biol., 1997, vol. 27, p. 887.

Kruszewska, "Heterologous expression of genes in filamentous fungi," Acta Biochimica Polonica, vol. 46, No. 1, pp. 181-195 (1999).

Kuchner et al., "Directed evolution of enzyme catalysts," Trends in Microbiology, vol. 15, pp. 523-530 (1997).

Liou et al., "Transformation of a Leu- Mutant of *Rhizopus niveus* with the leuA Gene of Mucor circinelloides," Biosci. Biotech. Biochem., vol. 56, No. 9, pp. 1503-1504 (1992).

Mandels, M. et al. Induction of Cellulase in *Trichoderma viride* as Influenced by Carbon Sources and Metals. J. Bacteriol., 1957, vol. 73, pp. 269-278.

Mantyla et al. Production in *Trichoderma reesei* xylanases of three xylanases from *Chaetomium thermophilum*: a recombinant thermoxylanase for biobleaching of kraft pulp. Appl. Microbiol. Biotechnol., 2007, vol. 76, pp. 377-386.

Maras et al., "Filamentous fungi as production organisms for glycoproteins of bio-medical interest," Glycoconjugate Journal, vol. 16, pp. 99-107 (1999).

Martinez, D. et al. Genome Sequencing and Analysis of the Biomass-Degrading Fungus *Trichoderma reesei* syn. *Hypocrea Jecorina*), Nature Biotechnol., 2008, vol. 26, pp. 553-560.

May et al., "Inverting enantioselectivity by directed evolution of hydantoinase for improved production of L-methionine," Nature Biotechnology, vol. 18, pp. 317-320 (2000).

(56) References Cited

OTHER PUBLICATIONS

Meynial-Salles et al. In vitro glycosylation of proteins: An enzymatic approach. J. Biotechnol., 1996, vol. 46, pp. 1-14.
Mielenz. Ethanol Production from Biomass: Technology and Commercialization Status. Current Opinion in Microbiology, 2001, vol. 4, pp. 324-329.
Miyazaki et al., "Directed Evolution Study of Temperature Adaptation in a Psychrophilic Enzyme," J. Mol. Biol., vol. 297, pp. 1015-1026 (2000).
Munoz-Rivas et al., "Transformation of the basidiomycete, *Schizophyllum commune*," Mol. Gen. Gent., vol. 205, pp. 103-106 (1986).
Oberson, J. et al. Comparative investigation of cellulose-degrading enzyme systems produced by different strains of *Myceliophthora thermophila* (Apinis) v. Oorschot. Enzyme Microb. Technol. 1992, vol. 14, pp. 303-312.
Pages et al. ARhamnogalacturonan Lyase in the *Clostridium cellulolyticum* Cellulosome. J. Bacteriol. vol. 185, pp. 4727-4733 (2003).
Peberdy, "Extracellular Proteins in Fungi: A Cytological and Molecular Perspective," Acta Microbiologica et Immunologica Hungarica, vol. 46, pp. 165-174 (1999).
Qureshi, M.S.A. et al. Cellulolytic Activity of Some Thermophilic and Thermotolerant Fungi of Pakistan, Viologia, vol. 26, Nos. 1-2, 1980, pp. 201-217.
Reese, E.T. et al. Beta-D-1,3 Glucanases in Fungi. Can. J. Microbiol. 1959, vol. 5, pp. 173-185.
Ridder, R. et al. 1992. Sequence Analysis of the Gene Coding for Glyceraldehyde-3-Phosphate Dehydrogenase GPD of *Podospora-anserina* use of Homologous Regulatory Sequences to Improve Transformation Efficiency. Current Genetics, vol. 21, No. 3, pp. 207-213.
Roller et al. Biotechnology in the Production and Modification of Biopolymers for Foods. Critical Reviews in Biotechnology, 1992, vol. 12, No. 3, pp. 261-277.
Ruiz-Roldan, M.C. et al. *Fusarium Oxysporum* f.s.p. lycopersici. Family F xylanase (XYL3). Accession No. o59937, Aug. 1, 1998.
Sakamoto et al. Molecular characterization of a *Penicillium chrysogenum* exo-1,5-a-L-arbinanase that is structurally distinct from other arabinan-degrading enzymes. FEBS Lett. 2004, vol. 506, pp. 199-204.
Saloheimo et al. cDNA cloning of a *Trichoderma reesei* cellulose and demonstration of endoglucanase activity by expression in yeast. Eur. J. Biochem, 1997, vol. 249, p. 584-591.
Seffernick, et al. 2001. Melamine deaminase and atrazine chloroydrolase: 98 percent identical but functionally different. Journal of Bacteriology, vol. 183, No. 8, pp. 2405-2410.
Sheehan et al. Enzymes, energy and the Environment: A Strategic Perspective on the U.S. Department of Energy's Research and Development Activities for Bioethanol. Biotechnology Progress, 1999, vol. 15, pp. 817-827.
Sheppard, P.O. et al. 1994. The Use of Conserved Cellulse Family-Specific Sequences to Clone Cellulase Homologue cDNAs from *Fusarium oxysporum*, XP002154884, Abstract.
Sheppard, P.O. et al. The Use of Conserved Cellulse Family-Specific Sequences to Clone Cellulase Homologue cDNAs from *Fusarium oxysporum*. Gene, 1994, vol. 150, pp. 163-167.
Shin et al. A comparison of the pectate lyase genes, pel-1 and pel-2, of *Colletotrichum gloeosporioides* f.sp. malvae and the relationship between their expression in culture and during necrotrophic infection. Gene, 2000, vol. 243, pp. 139-150.
Sorensen et al. Efficiencies of Designed Enzyme Combinations in Releasing Arabinose and Xylose from Wheat Arabinoxylan in an Industrial Ethanol Fermentation Residue. Enzyme Microb. Technol., 2005, vol. 36, pp. 773-784.
Sørensen et al. A Novel GH43 alpha-L-arabinofuranosidase from Humicola insolens: Mode of Action and Synergy with GH51 alpha-L-arabinofuranosidases on wheat arabinoxylan. Appl. Microbiol. Biotechnol. 2006, vol. 73, pp. 850-861.
Sørensen et al. Enzymatic Hydrolysis of Wheat Arabinoxylan by a Recombinant "Minimal" Enzyme Cocktail Containing B-Xylosidase and Novel Endo-1,4-B-Xylanase and a-L-Arabinofuranosidase Activities. Biotechnol. Progr., 2007, vol. 23, pp. 100-107.
Takami et al. Complete genome sequence of the alkaliphilic bacterium *Bacillus halodurans* and genomic sequence comparison with *Bacillus subtilis*. Nucleic Acid Res, 2000, vol. 28, pp. 4317-4331.
Takishima, S. et al. Cloning, Sequencing, and Expression of the Cellulase Genes of *Humicola grisea* Var. Thermoida. Accession No. D63515, Aug. 21, 1995.
Takashima, S. et al. Cloning, Sequencing, and Expression of the Cellulase Genes of *Humicola grisea* Var. Thermoidea. Journal of Biotechnology, 1996, vol. 50, pp. 137-147.
Unkles, S.E. et al. The development of a homologous transformation system for *Aspergillus oryzae* based on the nitrate assimilation pathway: A convenient and general selection system for filamentous fungal transformation. Mol. Gen. Genet., 1989, vol. 218, pp. 99-104.
Uzcategui et al. The 1,4-b-d-glucan glucanohydrolases from *Phanerochaete chrysosporium*. Re-assessment of their significance in cellulose degradation mechanisms. Journal of Biotechnology, 1991, vol. 21, pp. 143-160.
Van De Rhee et al., "Transformation of the cultivated mushroom, *Agaricus bisporus*, to hygromycin B resistance," Mol. Gen. Genet., vol. 250, pp. 252-258 (1996).
Van Den Broek L.A.M. et al. Cloning and Characterization of Arabinoxylan Arabinofuranosidase-D3 (AXHd3) from *Bifidobacterium adolescentis* DSM 20083. Appl. Microbiol. Biotechnol, 2005, vol. 67, pp. 641-647.
Van Laere, D.M.J. et al. A New Arabinofuranohydrolase from *Bifidobacterium adolescentis* Able to Remove Arabinosyl Residues from Double-Substitutes Xylose Units in Arabinoxylan. Appl. Microbiol. Biotechnol, 1997, vol. 47, pp. 231-235.
Van Oorschot, A Revision of *Chrysosporium* and Allied Genera. Studies in Mycology, 1980, No. 20, pp. 1-3, 8-9 and 32-35.
Van Zeijl et al., "An improved colony-PCR method for filamentous fungi for amplification of PCR-fragments of several kilobases," Journal of Biotechnology, vol. 59, pp. 221-224.
Verdoes et al., "characterization of an efficient gene cloning strategy for *Aspergillus niger* based on an autonomously replicating plasmid: cloning of the nicB gene of *A. niger*," Gene, vol. 146, pp. 159-165 (1994).
Viikari et al. Use of Cellulases in Pulp and Paper Applications. In Carbohydrates from *Trichoderma Reesei* and Other Microorganisms. Structure, Biochemistry, Genetics, and Applications. Claessens, M. et al. eds. The Royal Society of Chemistry, 1998, pp. 245-254.
Xu et al. Humicola insolens cellobiose dehydrogenase: cloning, redox chemistry, and "logic gate"-like dual functionality. Enzyme Microb. Technol., 2001, vol. 28, p. 744-753.
Yano et al. Cloning and Expression of an a-1,3-Glucanase Gene from *Bacillus circulans* KA-304: The Enzyme Participates in Protoplast Formation of *Schizophyllum commune*. Biosci Biotechnol. Biochem., 2006, vol. 70, pp. 1754-1763.
Office Action, dated May 27, 2010, for U.S. Appl. No. 12/047,709, filed Mar. 13, 2008, entitled "Transformation System in the Field of Filamentous Fungal Hosts.".
Food and Drug Administration. Agency Response Letter GRAS Notice No. GRN 000292, dated Sep. 29, 2009, from Mitchell A. Cheesman, Acting Director, to Richard H. Jundzil, Dyadic International (USC), Inc. (hyper text transfer protocol://www.fda.gov).
Notice of Allowance and Fee(s) Due, dated Oct. 28, 2010, for U.S. Appl. No. 10/257,629, filed Apr. 11, 2003, entitled "Novel Expression-Regulating Sequences and Expression Products in the Field of Filamentous Fungi."
Notice of Allowance and Fee(s) Due, dated Dec. 1, 2010, for U.S. Appl. No. 11/833,133, filed Aug. 2, 2007, entitled "Novel Fungal Enzymes."
Bukhtojarov et al., "Cellulase Complex of the Fungus *Chrysosporium lucknowense*: Isolation and characterization of Endoglucanases and Cellobiohydrolases", Biochemistry (Moscow), vol. 69, No. 5, 2006, pp. 542-551.

(56) References Cited

OTHER PUBLICATIONS

Canevascini et al., "Fractionation and identification of cellulases and other extracellular enzymes produced by Sporotrichum (*Chrysosporium*) thermophile during growth on cellulose or cellobiose", Canadian Journal of Microbiology, vol. 29, 1983, pp. 1071-1080.

Chose, "Measurement of Cellulase Activities", Pure and Applied Chemistry, vol. 59, No. 2, 1987, pp. 257-268.

Gusakov et al., "Design of Highly Efficient Cellulase Mixtures for Enzymatic Hydrolyss of Cellulose", Biotechnology and Bioengineering, vol. 97, No. 5, Aug. 1, 2007, pp. 1028-1038.

Loginova et al, "*Myceliophthora thermophila*, A Thermophilic Fungus Decomposing Cellulose", Microbiology, 1983, pp. 605-608. (Russian language document with English language Abstract).

Oberson et al, "Comparative investigation of cellulose-degrading enzyme systems produced by different strains of *Myceliophthora thermophila* (Apinis) v. Oorschot", Enzyme Microbiology Technology, vol. 14, Apr. 1992, pp. 303-312.

Visser et al., "Development of a mature fungal technology and production platform for industrial enzymes based on a *Myceliophthora thermophila* isolate, previously known as *Chrysosporium lucknowense* C1", Industrial Biotechnology, Jun. 2011, pp. 214-223.

* cited by examiner

FIGURE 8

```
Translation of Contig 2370 14521-20840 cbh2(1-6360)
1          ctcagattctaggggtagggcgggagcagaggcgaaaattgggttgtagaatatgaggag
61         ctagggttgttaaactcaaagaacttcttgctcttgttcttagtcttctctcctgggaaa
121        agggggttttttccgaaagcggcgctatacgaagccagaggctactttccttgctttggat
181        ggcccttgtccaccgttcttgtttcccgtttgtcaattgcgacgttgccggcaacctagg
241        tcctaataattaggtagatatttcggtagaggtagtttaattatgcttcagtagagaaat
301        cgttgtctccacgtctcgcaaccttgcgaaacttcgccacattgaagatagcattgtctg
361        agttgattttaaccctttccagagacgatataatagtgcaagtttctttgatcggaatca
421        tcgacattcggattttcccttaattatatgaagtattcggcccacggaaccgggccccga
481        gcaggttgaaccgcgcaaaacctcaaccgagtcacctcgcgtccatgtttgtcatggaat
541        caggctccgaatcccgtcagatcagtcagttctggtggctatggacgcgggagttacggc
601        cagtcgtcccgttgttctggggggttgatcaacaggaggaagagatctgagatcgaacta
661        cacccattgatttatcgacgcataatcaagtttaataaaaaccaaacagcgtgtttggtg
721        ctaccaccgaatgcgagatccgggctagcccgcggaaggatgatggccacagatctagcg
781        tcatgtatgattattacctatgcatctatcttcgtatctgcctcgggttggcaacacctg
841        accgagagacgactcgacaaccctgacacttggcaaaagacatttcggttgacagcgggag
901        aactccagcgaggaagtcgcccagagatgcggatgagaagacaacgccgagacgtgccgg
961        cgttggctctccacgaatcggagccgactcttccgtttggccaatctccgggataaatcc
1021       cagcggcgggtcacgtcacgtttcatggggaggcgcggacagccatcccagccaggccat
1081       ggaagagaacaattcttgggggtagcgaccgagccaaaggggggggggggaagcgggag
1141       gggaagaagtggtattagagcacgcaccggaaaacgcatttgggcccttgccaacaaaca
1201       ccacaccccgcgtcctgggagcaagacatccaggatgcaaccccagtaggggatgccaaga
1261       agcatctacggcaccatctgccggcgcctcgcctgttagagtcccggcacccgccaatgg
1321       ggccgtgctgggccctgcccggcaatgctggcgcagcggcatcaacaacattgctcgggg
1381       aggggcccgatttttattgattagcaaaaaaacaattaaattacccttccattccagcaga
1441       gcttctcctccacgcggcggcgggaccgcttgtggacggcggtacactacaaccgcgggg
1501       ctccagtctccgtgctgggcgtgcagatcacgaccccggaagagaaatgatcgcggtctga
1561       cgccgggtacggagtactgagccgccaaccacagccgatggaccgtgatatctcaatgcg
1621       ttcaagcaacacagcaacaccctggacgagtctctcctcccctaccaccccctcccccc
1681       tgccctggccgcgaacggggcgcgtacccccagatttctactccgtactgacaccccaatc
1741       tattcccgctggcgtcgcccagtctgggcggtccggccaagactctcggtgcacgatac
1801       cgcgacgaaatcggattaaccgttggctgatcaattccaagtcaagggagaagtggtatg
1861       gaaagtcggctcagttttccactgcccccgacaggcaggttccggatctggacagcagtc
1921       ttccgaatcttttggcagagactcatgataatataaaaaggcaaatgaggcggcgccttgg
1981       acaggtccattctcccaccgctcaaccagcctccaattcctcagaagtctgttgctctct
2041       cgcagtcgcagtcaagATGAAGCAGTACCTCCAGTACCTCGCGGCGACCCTGCCCCTGGT
                           M  K  Q  Y  L  Q  Y  L  A  A  T  L  P  L  V
2101       GGGCCTGGCCACGGCCCAGCAGGCGGGTAACCTGCAGACCGAGACTCACCCCAAGCTCAC
           G  L  A  T  A  Q  Q  A  G  N  L  Q  T  E  T  H  P  K  L  T
2161       TTGGTCGAAGTGCACGGCCCCGGGATCCTGCCAACAGGTCAACGGCGAGGTCGTCATCGA
           W  S  K  C  T  A  P  G  S  C  Q  Q  V  N  G  E  V  V  I  D
2221       CTCCAACTGGCGCTGGGTGCACGACGAGAACGCGCAGAACTGCTACGACGGCAACCAGTG
           S  N  W  R  W  V  H  D  E  N  A  Q  N  C  Y  D  G  N  Q  W
2281       GACCAACGCTTGCAGCTCTGCCACCGACTGCGCCGAGAATTGCGCGCTCGAGGGTGCCGA
           T  N  A  C  S  S  A  T  D  C  A  E  N  C  A  L  E  G  A  D
2341       CTACCAGGGCACCTATGGCGCCTCGACCAGCGGCAATGCCCTGACGCTCACCTTCGTCAC
           Y  Q  G  T  Y  G  A  S  T  S  G  N  A  L  T  L  T  F  V  T
2401       TAAGCACGAGTACGGCACCAACATTGGTTCGCGCCTCTACCTCATGAACGGCGCGAACAA
           K  H  E  Y  G  T  N  I  G  S  R  L  Y  L  M  N  G  A  N  K
2461       GTACCAGATGTTCACCCTCAAGGGCAACGAGCTGGCCTTCGACGTCGACCTCTCGGCCGT
           Y  Q  M  F  T  L  K  G  N  E  L  A  F  D  V  D  L  S  A  V
2521       CGAGTGCGGCCTCAACAGCGCCCTCTACTTCGTGGCCATGGAGGAGGATGGCGGTGTGTC
           E  C  G  L  N  S  A  L  Y  F  V  A  M  E  E  D  G  G  V  S
2581       GAGCTACCCGACCAACACGGCCGGTGCTAAGTTCGGCACTGGGgtaagttcaacgacccg
           S  Y  P  T  N  T  A  G  A  K  F  G  T  G
2641       agacgggtgcccttattatctgctgcgaaaacggacggtccccttttgctaactaccctc
2701       ctccaaacagTACTGCGACGCCCAATGCGCACGCGACCTCAAGTTCGTCGGCGGCAAGGG
                           Y  C  D  A  Q  C  A  R  D  L  K  F  V  G  G  K  G
2761       CAACATCGAGGGCTGGAAGCCGTCCACCAACGATGCCAATGCCGGTGTCGGTCCTTATGG
           N  I  E  G  W  K  P  S  T  N  D  A  N  A  G  V  G  P  Y  G
2821       CGGGTGCTGCGCTGAGATCGACGTCTGgtaagttttgttgcctgggcagcaatggtatat
           G  C  C  A  E  I  D  V  W
2881       tagctcgagtggttcccgtcgttgctgaccctctcttaccagGGAGTCGAACAAGTATGC
                                                       E  S  N  K  Y  A
2941       TTTCGCTTTCACCCCGCACGGTTGCGAGAACCCTAAATACCACGTCTGCGAGACCACCAA
           F  A  F  T  P  H  G  C  E  N  P  K  Y  H  V  C  E  T  T  N
```

(FIGURE 8, continued)

```
3001    CTGCGGTGGCACCTACTCCGAGGACCGCTTCGCTGGTGACTGCGATGCCAACGGCTGCGA
         C  G  G  T  Y  S  E  D  R  F  A  G  D  C  D  A  N  G  C  D
3061    CTACAACCCCTACCGCATGGGCAACCAGGACTTCTACGGTCCCGGCTTGACGGTCGATAC
         Y  N  P  Y  R  M  G  N  Q  D  F  Y  G  P  G  L  T  V  D  T
3121    CAGCAAGAAGTTCACgtgagtacaccgtgcttgaagcccctcccccccccccccaaaa
         S  K  K  F  T
3181    aaaaaagaaaaaagaagtcaaatgattgatgctaaccaaatcaaataacagCGTCGTCA
                                                             V  V
3241    GCCAGTTCGAGGAGAACAAGCTCACCCAGTTCTTCGTCCAGGACGGCAAGAAGATTGAGA
         S  Q  F  E  E  N  K  L  T  Q  F  F  V  Q  D  G  K  K  I  E
3301    TCCCCGGCCCCAAGGTCGAGGGCATCGATGCGGACAGCGCCGCTATCACCCCGTGAGCTGT
         I  P  G  P  K  V  E  G  I  D  A  D  S  A  A  I  T  P  E  L
3361    GCAGTGCCCTGTTCAAGGCCTTCGATGACCGTGACCGCTTCTCGGAGGTTGGCGGCTTCG
         C  S  A  L  F  K  A  F  D  D  R  D  R  F  S  E  V  G  G  F
3421    ATGCCATCAACACGGCCCTCAGCACTCCCATGGTCCTCGTCATGTCCATCTGGGATGATg
         D  A  I  N  T  A  L  S  P  M  V  L  V  M  S  I  W  D  D 3481    tacgttacctaaccccccccccccttttttttcccgcttctctcccgaaactgccacta
3541    cttatatacgtcccgcgtccatgatgcttacctttctccttccagCACTACGCCAATAT
                                                        H  Y  A  N  M
3601    GCTCTGGCTCGACTCGAGCTACCCCCCTGAGAAGGCTGGCCAGCCTGGCGGTGACCGTGG
         L  W  L  D  S  S  Y  P  P  E  K  A  G  Q  P  G  G  D  R  G
3661    CCCGTGTCCTCAGGACTCTGGCGTCCCGGCCGACGTTGAGGCTCAGTACCCTAATGCGTG
         P  C  P  Q  D  S  G  V  P  A  D  V  E  A  Q  Y  P  N  A  *
3721    agtcgaaaccgtaaaatgtcgggcaaaaaaaagatcgctcaagctaacgaaataatatga
3781    ttagCAAGGTCATCTGGTCCAACATCCGCTTCGGCCCCATCGGCTCGACTGTCAACGTCT
            K  V  I  W  S  N  I  R  F  G  P  I  G  S  T  V  N  V
3841    AAactgcaacctgaccgggccctttctctccaccccaccctctcaagttctctctggt
3901    ggagccctcgtgtccttcttttcctaggttcgcgaacctttgagcttgtgtatcgtaggg
3961    tcattgtgtacatacacaaaaacttaacatctgctaccaagatcttggcgctttgccagg
4021    tcttctcaaacctcgaagcactgagcctttgtcctccgagtgaagtaggatgactattta
4081    cgttgcaagactacgcggtaaagggacggagcagacctgccacagatattcgtttggtt
4141    gcttgatttatagcagagtccgaacgtagacatggcccctgaaggtgccaaccctagata
4201    gccagaagccttgttttacgaaaggggtggtcaaccaacggtgctcctcgctcagcgaatc
4261    tacccgcacgcaatgtatcgtaagaatgtgaactaaagggaacgacgaggcatagggaaa
4321    cgtcaatgtggcttgaataacagagttaaatacctaatagaagaaattagcatgccaaga
4381    ttgagccagcaacacatggtagaatagccagcaaaggacgcttgttcgcttgatctcgaa
4441    ccgtccaacctgattcgaaggaggagggaaaagttgaagaataccggcaataattactcg
4501    aggttcctatgccctgcagagtctaattaatattaaaggcaccaccgcatgattccgca
4561    attataagcataataagctcgcgggccccacacgtgccttcaccctcccatgtgtataca
4621    atctgtacctcgttattgtcgaatcgctattccgatagcgaaggtctggcactcatcaga
4801    taccgtgacatcgattgagatttggccgggccaccggtagtaagcgatgagttggtcatc
4681    aattatcaacaatgcgctcaatcagcgataatcagcctatcaaccgcgaaatcatacgcg
4741    catcaacgaattgtccatcatgcacgtagcttgtcggcagtgccgcataccctccagagc
4861    atcatagccgggatagaaagctcgctttcagccgtcccagagtccgagatgcaggtagca
4921    agccttcaagaccagttatatgtgacccgggtaaaatacttggtgagatgcaatgggcgt
4981    agcttcgggcacttataagctttactagatattatctcaaggtttcttttttgaactcctc
5041    ctagacatttactataaactaccgagcttcaatgctagacgcctccttctgttaaatag
5101    tcttttccttctaagagcatctgccttttttcccttaggcttagaggatagggcccctcc
5161    atcttgctgcgacggccttagccttggggagtaattattggtatccgcgtacctgtttcc
5221    cagacagccgaagtttcgacgacaaagtaattattgcgacaataccaccgccatatgcta
5281    ttccgagtggggtgagccccgaaaacatcgcttaccgcatcgccatcccagacgacagagg
5341    gcgactttgatgtcttgctccagatcgccgcacctaacacggtgggatgggctggtatcg
5401    tatgggacggcatcatggtcaacaacccctgacgggtgttgggccaatggaaacacca
5461    ccgttgtctcgagccggatcgcaaggtaagccgaagaggacaaatgacgatgagactttc
5521    tttcttttttatttttatttttttttaaatttctttttttaagcgtaatgaaaagagctaca
5581    tatctgtggttcgttcctcaatttcagcgacctctccaccgaagcatcgtcaaataagaa
5641    gttgtcggaaacaaagggtgtcagaagctatagagcttctaaggatattagccacataca
5701    tgccatagctgtataaggctatttaacgctttggccagctcctttgtctataaatattag
5761    tcgttttgtctcctttgtagataattttaacaaggcactcttttcctttatatagccacc
5821    tactatagactgctttcaacgctcccggaagcttattactacgttcggcagttataagcc
5881    tggcgccttgactactcctctgccgacgtatctttaatattagtagtagcttcttctatt
5941    acgaactctcttaccctgctttaatacgctttcgacgacgtgtctattatatctaagatc
6001    ctagtcgagacttctatatgccttactaggcctagttcttagaacttgtagtatattaaa
6061    ctatagttataggctaaatttgctagtatatagagatttgttaaccttaatagtaattat
6121    aaactagatctagaagttttatagtgcctaacctataaataagctagagataaccttatt
6181    ttagcttcctaggagtaattcctagaaggagtattacctttaatatctatagatttgata
6241    ccttctaatatagctatcatagctaaatttatataattataagattccttttataaaaat
```

(FIGURE 8, continued)

```
6301      attatatatactatagatattagtaagtagataggatagctataatactagctagtatat
```

FIGURE 9

SEQ ID NOs: 3 and 4   cbh4 gene encoding CBH IIb

| | |
|---|---|
| 1 | ccgcaagtgaatatgtaattactcaatggaagttctcgaaacggagtccagaaatgatgt |
| 61 | ggttctgtgggaatgcggcaagaggcgacgttgccgtgaatgcgtgaacattcccgcctc |
| 121 | ttcttcttctcgtcttcttccttcttcttctttcgggtcgcggatggttgacggccagcg |
| 181 | tgcgcacggctgcgtgttatcgagcgtcggtacgtctagccaacatcccgtagacacgac |
| 241 | gaccaagcgtcttgagaatgcaacaacgtctcggaacctggcacgcatcttccgccgcag |
| 301 | gtcggcagacgccgcctgggcaataccaccctgtccaggccctttccccgcaggcagag |
| 361 | ccgcgctcttcctttcatggttattcaggaacgtggcttccgagattctcgcctgttctc |
| 421 | ccccagtcaacctgccgaccgtaacccggttccaccaccgcggactgtccgcaaaacctg |
| 481 | gttcgcccgagattaatatgctatttccggactaagtgcacaacacacaagcacccttc |
| 541 | cgcctcgcgctctagaatctgctttctaacccggttctcgggcccttcccttccgcgacg |
| 601 | cctccgctctccttaccaggcaccatccgcaataggtaaggtagccaaccgttttggagc |
| 661 | gtgattctgccaaggaccgcatccttgcattcgccatctggtcaaggacccctctttccc |
| 721 | gctccattctggtggctctatcgggacggcgttcccatggctctccaggagagtgatgt |
| 781 | gcgagtctggagagccggggttggcgtcacgatgctgcccacctagggccggccagcccg |
| 841 | gcactgcgctcccgttgatccgtctatccccgtcaagagcaccagccccggcgctcgtga |
| 901 | attttcgacttgttcgacttgctacaggtgataaagaggatgcacgccgccctcgatcgg |
| 961 | cctgtgtggtttctctccctcgtgccaaaccactcccacctcccgccccgagatagttgc |
| 1021 | ttgtttcgctccgtgagagggacacacaccaATGGCCAAGAAGCTTTTCATCACCGCCGC |
| |                              M  A  K  K  L  F  I  T  A  A |
| 1081 | GCTTGCGGCTGCCGTGTTGGCGGCCCCCGTCATTGAGGAGCGCCAGAACTGCGGCGCTGT |
| 361 |   L  A  A  A  V  L  A  A  P  V  I  E  E  R  Q  N  C  G  A  V |
| 1141 | gtggtaagaaagcccggtccgagtctcccatgattttctcgtcgagtaatggcataaggg |
| 1201 | ccaccccttcgactgaccgtgagaatcgatcaaatccagGACTCAATGCGGCGGTAACGG |
| |                                        T  Q  C  G  G  N  G |
| 1261 | GTGGCAAGGTCCCACATGCTGCGCCTCGGGCTCGACCTGCGTTGCGCAGAACGAGTGGTA |
| |   W  Q  G  P  T  C  C  A  S  G  S  T  C  V  A  Q  N  E  W  Y |

FIGURE 9 (CONT'D)

SEQ ID NOs: 3 and 4 cbh4 gene encoding CBH IIb

```
1321    CTCTCAGTGCCTGCCCAACAGCCAGGTGACGAGTTCCACCACTCCGTCGTCGACTTCCAC
         S  Q  C  L  P  N  S  Q  V  T  S  S  T  T  P  S  S  T  S  T

1381    CTCGCAGCGCAGCACCAGCACCTCCAGCAGCACCACCAGGAGCGGCAGCTCCTCCTCCTC
         S  Q  R  S  T  S  T  S  S  S  T  T  R  S  G  S  S  S  S  S

1441    CTCCACCACGCCCCCGCCCGTCTCCAGCCCCGTGACCAGCATTCCCGGCGGTGCGACCTC
         S  T  T  P  P  P  V  S  S  P  V  T  S  I  P  G  G  A  T  S

1501    CACGGCGAGCTACTCTGGCAACCCCTTCTCGGGCGTCCGGCTCTTCGCCAACGACTACTA
         T  A  S  Y  S  G  N  P  F  S  G  V  R  L  F  A  N  D  Y  Y

1561    CAGGTCCGAGGTCCACAATCTCGCCATTCCTAGCATGACTGGTACTCTGGCGGCCAAGGC
         R  S  E  V  H  N  L  A  I  P  S  M  T  G  T  L  A  A  K  A

1621    TTCCGCCGTCGCCGAAGTCCCTAGCTTCCAGTGGCTCGACCGGAACGTCACCATCGACAC
         S  A  V  A  E  V  P  S  F  Q  W  L  D  R  N  V  T  I  D  T

1681    CCTGATGGTCCAGACTCTGTCCCAGGTCCGGGCTCTCAATAAGGCCGGTGCCAATCCTCC
         L  M  V  Q  T  L  S  Q  V  R  A  L  N  K  A  G  A  N  P  P

1741    CTATGCTGgtgagttacatggcgacttgccttctcgtcccctacctttcttgacgggatc
         Y  A 1801    ggttacctgacctggaggcaaaacaacaacagCCCAACTCGTCGTCTACGACCTCCCCGA
                                          A  Q  L  V  V  Y  D  L  P  D 1861    CCGTGACTGTGCCGCCGCTGCGTCCAACGGCGAGTTTTCGATTGCAAACGGCGGCGCCGC
         R  D  C  A  A  A  A  S  N  G  E  F  S  I  A  N  G  G  A  A

1921    CAACTACAGGAGCTACATCGACGCTATCCGCAAGCACATCATTGAGTACTCGGACATCCG
```

FIGURE 9 (CONT'D)

SEQ ID NOs: 3 and 4   cbh4 gene encoding CBH IIb

```
             N  Y  R  S  Y  I  D  A  I  R  K  H  I  I  E  Y  S  D  I  R

1981   GATCATCCTGGTTATCGAGCCCGACTCGATGGCCAACATGGTGACCAACATGAACGTGGC
         I  I  L  V  I  E  P  D  S  M  A  N  M  V  T  N  M  N  V  A

2041   CAAGTGCAGCAACGCCGCGTCGACGTACCACGAGTTGACCGTGTACGCGCTCAAGCAGCT
         K  C  S  N  A  A  S  T  Y  H  E  L  T  V  Y  A  L  K  Q  L

2101   GAACCTGCCCAACGTCGCCATGTATCTCGACGCCGGCCACGCCGGCTGGCTCGGCTGGCC
         N  L  P  N  V  A  M  Y  L  D  A  G  H  A  G  W  L  G  W  P

2161   CGCCAACATCCAGCCCGCCGCCGAGCTGTTTGCCGGCATCTACAATGATGCCGGCAAGCC
         A  N  I  Q  P  A  A  E  L  F  A  G  I  Y  N  D  A  G  K  P

2221   GGCTGCCGTCCGCGGCCTGGCCACTAACGTCGCCAACTACAACGCCTGGAGCATCGCTTC
         A  A  V  R  G  L  A  T  N  V  A  N  Y  N  A  W  S  I  A  S

2281   GGCCCCGTCGTACACGTCGCCTAACCCTAACTACGACGAGAAGCACTACATCGAGGCCTT
         A  P  S  Y  T  S  P  N  P  N  Y  D  E  K  H  Y  I  E  A  F

2341   CAGCCCGCTCTTGAACTCGGCCGGCTTCCCCGCACGCTTCATTGTCGACACTGGCCGCAA
         S  P  L  L  N  S  A  G  F  P  A  R  F  I  V  D  T  G  R  N

2401   CGGCAAACAACCTACCGgtatgtttttttttcttttgtctctgtccccccttttctccc
         G  K  Q  P  T 2461   ccttcagttggcgtccacaaggtctcttagtcctgcttcatctgtgaccaacctccccc 2521   ccccggcaccgcccacaaccgtttgactctatactcttgggaatgggcgccgaaactgac 2581   cgttccacagGCCAACAACAGTGGGGTGACTGGTGCAATGTCAAGGGCACCGGCTTTGGC
```

FIGURE 9 (CONT'D)

SEQ ID NOs: 3 and 4    cbh4 gene encoding CBH IIb

```
                          S  Q  Q  W  G  D  W  C  N  V  K  G  T  G  F  G

2641    GTGCGCCCGACGGCCAACACGGGCCACGAGCTGGTCGATGCCTTTGTCTGGGTCAAGCCC
         V  R  P  T  A  N  T  G  H  E  L  V  D  A  F  V  W  V  K  P

2701    GGCGGCGAGTCCGACGGCACAAGCGACACCAGCGCCGCCCGCTACGACTACCACTGCGGC
         G  G  E  S  D  G  T  S  D  T  S  A  A  R  Y  D  Y  H  C  G

2761    CTGTCCGATGCCCTGCAGCCTGCCCCCGAGGCTGGACAGTGGTTCCAGGCCTACTTCGAG
         L  S  D  A  L  Q  P  A  P  E  A  G  Q  W  F  Q  A  Y  F  E

2821    CAGCTGCTCACCAACGCCAACCCGCCCTTCTAAacctcgtcataaagagagagagatggc
         Q  L  L  T  N  A  N  P  P  F  *

2881    gggcatgggcctgattgggttcattgaccatgcggctcttctgggggtacatattttacc
2941    tacctacctataaataaggcggcctatcgggctctcgcttcgtttattaggtacttgttc
3001    ttgtacatactttgttttatacatacagcagttagcatccactattcgtttcgacaaagcg
3061    gaactttccagaaaaaaaaggttgtacataattagtctttaggcttcgattctttgtgc
3121    ctttcttttggtaaaaaaaaaattttttttgaggcatgattacctaggtacgttcgtc
3181    gttgtattggtccccctgcattttggcgcgagagcagctcagccccttgcaaatccctca
3241    acgggcgttcaattccctccactcgggtcttcagcgagaccagccgtccagagtatccca
3301    gcgtgtagttgccccacgaaccagtcgtcctcgtaagcctcgtcaaagtgtccaagagca
3361    gtatagaagcaacgacctccgtcaaaagtctggcaccatgcgatcgggtggtcctccccg
3421    tgcgccccgccctcgtaggacttctcatccacgccaaggagcacgtgcaggccgtcggac
3481    gtcgcccgcgggtgcgccttgaagttgtaccattcgtccttccagacgcgctccagctgc
3541    gcctgcttgggttcctgcggttcctgcggttcctgcgctggccggtcggcgccgccgtct
3601    tggtcacacgcccgcagcgacatgactgggtgtttcgggtcgagcagcttgacgagcccg
3661    acctggggttccgggtggttgtcgaacacggcgccaatgaggtggccgtaccattcggat
3721    gactgcatggcgaagctggcgcagtgtaccgccacgatcccgccgcccgcctggacgaaa
3781    ccccgcagggcgcccagctgcgcgccgtccaggaactcgcccgagcactgcaggaggacg
3841    atgacgcgatacgccgagagggagccggggctgaacacggcgggatcctcgctgtcgtcc
```

FIGURE 10

SEQ ID NOs: 5 and 6    cbh1 gene encoding CBH Ia

```
                                          ATGTACGCCAAGTTCGCGACC  1800
                                          M  Y  A  K  F  A  T

CTCGCCGCCCTTGTGGCTGGCGCCGCTGCTCAGAACGCCTGCACTCTGACCGCTGAGAAC    1860
 L  A  A  L  V  A  G  A  A  A  Q  N  A  C  T  L  T  A  E  N

CACCCCTCGCTGACGTGGTCCAAGTGCACGTCTGGCGGCAGCTGCACCAGCGTCCAGGGT    1920
 H  P  S  L  T  W  S  K  C  T  S  G  G  S  C  T  S  V  Q  G

TCCATCACCATCGACGCCAACTGGCGGTGGACTCACCGGACCGATAGCGCCACCAACTGC    1980
 S  I  T  I  D  A  N  W  R  W  T  H  R  T  D  S  A  T  N  C

TACGAGGGCAACAAGTGGGATACTTCGTACTGCAGCGATGGTCCTTCTTGCGCCTCCAAG    2040
 Y  E  G  N  K  W  D  T  S  Y  C  S  D  G  P  S  C  A  S  K

TGCTGCATCGACGGCGCTGACTACTCGAGCACCTATGGCATCACCACGAGCGGTAACTCC    2100
 C  C  I  D  G  A  D  Y  S  S  T  Y  G  I  T  T  S  G  N  S

CTGAACCTCAAGTTCGTCACCAAGGGCCAGTACTCGACCAACATCGGCTCGCGTACCTAC    2160
 L  N  L  K  F  V  T  K  G  Q  Y  S  T  N  I  G  S  R  T  Y

CTGATGGAGAGCGACACCAAGTACCAGAgtaagttcctctcgcacccggccgccgggaga    2220
 L  M  E  S  D  T  K  Y  Q  M tgatggcgcccagcccgctgacgcgaatgacacaGTGTTCCAGCTCCTCGGCAACGAGTT    2280
                                    F  Q  L  L  G  N  E  F CACCTTCGATGTCGACGTCTCCAACCTCGGCTGCGGCCTCAATGGCGCCCTCTACTTCGT    2340
 T  F  D  V  D  V  S  N  L  G  C  G  L  N  G  A  L  Y  F  V GTCCATGGATGCCGATGGTGGCATGTCCAAGTACTCGGGCAACAAGGCAGGTGCCAAGTA    2400
 S  M  D  A  D  G  G  M  S  K  Y  S  G  N  K  A  G  A  K  Y CGGTACCGGCTACTGTGATTCTCAGTGCCCCCGCGACCTCAAGTTCATCAACGGCGAGGC    2460
 G  T  G  Y  C  D  S  Q  C  P  R  D  L  K  F  I  N  G  E  A CAACGTAGAGAACTGGCAGAGCTCGACCAACGATGCCAACGCCGGCACGGGCAAGTACGG    2520
 N  V  E  N  W  Q  S  S  T  N  D  A  N  A  G  T  G  K  Y  G CAGCTGCTGCTCCGAGATGGACGTCTGGGAGGCCAACAACATGGCCGCCGCCTTCACTCC    2580
 S  C  C  S  E  M  D  V  W  E  A  N  N  M  A  A  A  F  T  P CCACCCTTGCNCCGTGATCGGCCAGTCGCGCTGCGAGGGCGACTCGTGCGGCGGTACCTA    2640
 H  P  C  ?  V  I  G  Q  S  R  C  E  G  D  S  C  G  G  T  Y CAGCACCGACCGCTATGCCGGCATCTGCGACCCCGACGGATGCGACTTCAACTCGTACCG    2700
 S  T  D  R  Y  A  G  I  C  D  P  D  G  C  D  F  N  S  Y  R CCAGGGCAACAAGACCTTCTACGGCAAGGGCATGACGGTCGACACGACCAAGAAGATCAC    2760
 Q  G  N  K  T  F  Y  G  K  G  M  T  V  D  T  T  K  K  I  T
```

FIGURE 10 (CONT'D)

SEQ ID NOs: 5 and 6   cbh1 gene encoding CBH Ia

```
GGTCGTCACCCAGTTCCTCAAGAACTCGGCCGGCGAGCTCTCCGAGATCAAGCGGTTCTA    2820
 V  V  T  Q  F  L  K  N  S  A  G  E  L  S  E  I  K  R  F  Y

CGTCCAGAACGGCAAGGTCATCCCCAACTCCGAGTCCACCATCCCGGGCGTCGAGGGCAA    2880
 V  Q  N  G  K  V  I  P  N  S  E  S  T  I  P  G  V  E  G  N

CTCCATCACCCAGGACTGGTGCGACCGCCAGAAGGCCGCCTTCGGCGACGTGACCGACTT    2940
 S  I  T  Q  D  W  C  D  R  Q  K  A  A  F  G  D  V  T  D  ?

NCAGGACAAGGGCGGCATGGTCCAGATGGGCAAGGCCCTCGCGGGGCCCATGGTCCTCGT    3000
 Q  D  K  G  G  M  V  Q  M  G  K  A  L  A  G  P  M  V  L  V

CATGTCCATCTGGGACGACCACGCCGTCAACATGCTCTGGCTCGACTCCACCTGGCCCAT    3060
 M  S  I  W  D  D  H  A  V  N  M  L  W  L  D  S  T  W  P  I

CGACGGCGCCGGCAAGCCGGGCGCCGAGCGCGGTGCCTGCCCCACCACCTCGGGCGTCCC    3120
 D  G  A  G  K  P  G  A  E  R  G  A  C  P  T  T  S  G  V  P

CGCTGAGGTCGAGGCCGAGGCCCCCAACTCCAACGTCATCTTCTCCAACATCCGCTTCGG    3180
 A  E  V  E  A  E  A  P  N  S  N  V  I  F  S  N  I  R  F  G

CCCCATCGGCTCCACCGTCTCCGGCCTGCCCGACGGCGGCAGCGGCAACCCCAACCCGCC    3240
 P  I  G  S  T  V  S  G  L  P  D  G  G  S  G  N  P  N  P  P

CGTCAGCTCGTCCACCCCGGTCCCCTCCTCGTCCACCACATCCTCCGGTTCCTCCGGCCC    3300
 V  S  S  S  T  P  V  P  S  S  S  T  T  S  S  G  S  S  G  P

GACTGGCGGCACGGGTGTCGCTAAGCACTATGAGCAATGCGGAGGAATCGGGTTCACTGG    3360
 T  G  G  T  G  V  A  K  H  Y  E  Q  C  G  G  I  G  F  T  G

CCCTACCCAGTGCGAGAGCCCCTACACTTGCACCAAGCTGAATGACTGGTACTCGCAGTG    3420
 P  T  Q  C  E  S  P  Y  T  C  T  K  L  N  D  W  Y  S  Q  C

CCTGTAA
 L  *
```

FIGURE 11

SEQ ID NOs: 7 and 8 eg6 gene encoding CBHIIa

| | | | | | | |
|---|---|---|---|---|---|---|
| ggatccacac | ctaccatacc | ggatagtatg | ctacccaagt | gacatagggt | tggtaaagta | 60 |
| atacgagaac | tcagagagca | ctgcccatat | ggctcgccaa | tgacctcaag | tgccaggtca | 120 |
| gctttgcgag | acagacctga | gcgcgtcgga | tgtgtgacat | ggaacgcgcc | ggatcgcctt | 180 |
| gttgattaat | tatagggaag | tagcgaggaa | ggtttcagca | attgacgtga | gcgtacatta | 240 |
| aaagctgtat | gatttcagga | agacgagcca | tggaccaggt | ttcaaggctg | aatggcttga | 300 |
| cgacttaagc | accgaacgag | gaatgaaaga | atgaaaagtg | ggggatcatt | ctggcccctc | 360 |
| ctcgtatgtc | gagtgttaaa | gaaggcggtt | ctacggagga | cctaaagagc | tccaatttgc | 420 |
| tctgttgagc | ttaagccaca | tatctcaaga | tgaatacatg | tcaggcatag | tcaccctgat | 480 |
| cttgttcatc | agtccacaca | cttttcagtt | cagcatgttg | attcctcatc | catatcactt | 540 |
| tccattacta | tctctttatg | tccttggtca | agactccaag | gaaccgatag | gtgagcatcg | 600 |
| gtgaggctcc | ctcaaggtac | caaagtagcc | atcatcaccg | aggtctggga | atggcgccgt | 660 |
| gcccgatctg | agtcctccaa | ctccacggta | cgacgacagc | acgtcacatt | gacgcaccac | 720 |
| ggttgaacaa | gcagagaggg | acacgtcttg | ctacgcgaat | cctggcactg | gatggagacg | 780 |
| cgtgtgagca | ggtttccgga | accatgacgg | cctggtccgg | cttctcgaac | aaagaagtgg | 840 |
| aacacaaaaa | gaaccgaaac | ggaaacgcag | gcacggcatc | gacgaccgga | ttgtcccacg | 900 |
| gggacctcgg | ccagtcaagc | gttgccctgg | ccgtcagctc | cctggcgacg | gggattcagc | 960 |
| acatctcacg | ttataggcga | cctcatcccc | cttccgtctt | gtgcggtcgt | tgctccgtgc | 1020 |
| cgagtaccca | ggcgtgccgg | ggcctttagc | cggggcggaa | tcagagtcaa | gatgcggccg | 1080 |
| aattggacgg | cagacgaagt | ttcgtagagg | gtcatgatcg | gcactgacga | cacccacccc | 1140 |
| tgcgtgatcc | cgtggccctg | ggctgggaat | tgccggctaa | taatctacgg | cttaatagat | 1200 |
| atgcactttg | cacgcggtgc | agataaataa | gctgtggttt | caaacactgg | cctccgtact | 1260 |
| ttacccacca | actgccgctt | agcgccggga | cctgagtctt | gggagtgcgc | ggagcggcag | 1320 |
| ccacctcggg | ttagcgtaca | cacgacggct | gcatgcgggg | atgccgcgtg | catggcttca | 1380 |
| tagtgtacga | cagaccgtca | agtccaaatc | tgggtgatgc | ttgatgagat | gacagcgagc | 1440 |
| cccgtcggcg | gcaccccggc | tatgcatcgc | gaattgacaa | cactctcagc | tctattgcga | 1500 |
| cccatcggat | aaaagaagaa | gaaaaaaatg | gaccttgagt | acgggcgtca | gaaaccaaaa | 1560 |
| aaaaactccg | gaaccaaata | tgtcgggcat | ggccggggtg | aacgaccgct | actccccgtt | 1620 |
| cccttcttcg | caaacagaac | gctacagagg | gttttctggt | ttgtcaaaga | gttcggaggt | 1680 |
| cctctgctcc | gcgaatgcgt | ggtgaaccca | ccagcagcca | ttgttcttgc | atgcgtggcg | 1740 |
| gaccgttagc | cgctgatcga | catggcgagc | ttcccacctc | agacctggag | cagacggttg | 1800 |
| cgaggagcaa | ggggctgccc | tcccctgac | ggtcggaccc | caatgacttc | cccaaacggg | 1860 |
| gacatcgagg | gtcgtgcatg | atggtggaaa | gtagttgcag | tatgggaagt | accccgggtt | 1920 |
| gccaggaacc | gttgttcggc | ccccacatt | ttctctctgc | catgtcaact | gtgtgtcgtt | 1980 |
| cgagagttcc | tggctccggc | ccccgtcca | attccctaac | gggaccgcgg | ggcatcgcct | 2040 |

FIGURE 11 (CONT'D)

SEQ ID NOs: 7 and 8   eg6 gene encoding CBHIIa

```
gtaactaact tccaaatgaa gccggatatg agggagggag attggatctg gcaagccagc    2100
cattcgctgc gatcggcact cgtccgtcag ccccgcagtc catatcccca aaggcaactg    2160
ctcggcgcgg ctcaagtctt cttcggaacg tccagcccga aggcgcgcgc cagcaccggc    2220
cctatgttcc tgattgcgat cctcgatctc cagagacggg tcacctcgcc tcgaggacgg    2280
tgcagggca tcggcttcgc ttcctagagc tccgggctgt gtgtggtcaa ggggagaagg     2340
cggcggcgcc aaggtgcgtc tcggcgcact cacccatcgc ctttaccccc ctccccccca    2400
gtatataaaa gatggccatc gtctcctcgt ctgcttggga agaaaggatc tctcgaccat    2460
gcaccacagc ctagctctaa cccagcttgt cgtgtgttgt tgcccagc atg aag ttc     2517
                                                    Met Lys Phe
                                                     1
gtg cag tcc gcc acc ctg gcg ttc gcc gcc acg gcc ctc gct gcg ccc      2565
Val Gln Ser Ala Thr Leu Ala Phe Ala Ala Thr Ala Leu Ala Ala Pro
     5                  10                 15
tcg cgc acg act ccc cag aag ccc cgc cag gcc tcg gcg ggc tgc gcg      2613
Ser Arg Thr Thr Pro Gln Lys Pro Arg Gln Ala Ser Ala Gly Cys Ala
20                  25                  30                  35
tcg gcc gtg acg ctc gat gcc agc acc aac gtg ttc cag cag tac acg      2661
Ser Ala Val Thr Leu Asp Ala Ser Thr Asn Val Phe Gln Gln Tyr Thr
             40                  45                  50
ctg cac ccc aac aac ttc tac cgt gcc gag gtc gag gct gcc gcc gag      2709
Leu His Pro Asn Asn Phe Tyr Arg Ala Glu Val Glu Ala Ala Ala Glu
                 55                  60                  65
gcc atc tcc gac tcg gcg ctg gcc gag aag gcc cgc aag gtc gcc gac      2757
Ala Ile Ser Asp Ser Ala Leu Ala Glu Lys Ala Arg Lys Val Ala Asp
                     70                  75                  80
gtc ggt acc ttc ctg tgg ctc gac acc atc gag aac att ggc cgg ctg      2805
Val Gly Thr Phe Leu Trp Leu Asp Thr Ile Glu Asn Ile Gly Arg Leu
     85                  90                  95
gag ccc gcg ctc gag gac gtg ccc tgc gag aac atc gtg ggt ctc gtc      2853
Glu Pro Ala Leu Glu Asp Val Pro Cys Glu Asn Ile Val Gly Leu Val
100                 105                 110                 115
atc tac gac ctc ccg ggc cgt gac tgc gcg gcc aag gcc tcc aac ggc      2901
Ile Tyr Asp Leu Pro Gly Arg Asp Cys Ala Ala Lys Ala Ser Asn Gly
                 120                 125                 130
```

FIGURE 11 (CONT'D)

SEQ ID NOs: 7 and 8  eg6 gene encoding CBHIIa

```
gag ctc aag gtc ggc gag ctc gac agg tac aag acc gag tac atc gac a        2950
Glu Leu Lys Val Gly Glu Leu Asp Arg Tyr Lys Thr Glu Tyr Ile Asp
            135                 140                 145
gtgagttaac cctttgtggc cccttctttt cccccgagag agcgtctggt tgagtggggt        3010
tgtgagagag aaaatggggc gagcttaaag actgacgtgt tggctcgcag ag atc           3065
                                                        Lys Ile gcc gag atc ctc aag gcc cac tcc aac acg gcc ttc gcc ctc gtc atc          3113
Ala Glu Ile Leu Lys Ala His Ser Asn Thr Ala Phe Ala Leu Val Ile
150                 155                 160                 165
gag ccc gac tcg ctc ccc aac ctg gtc acc aat agc gac ctg cag acg          3161
Glu Pro Asp Ser Leu Pro Asn Leu Val Thr Asn Ser Asp Leu Gln Thr
            170                 175                 180
tgc cag cag agc gct tcc ggc tac cgc gag ggt gtc gcc tat gcc ctc          3209
Cys Gln Gln Ser Ala Ser Gly Tyr Arg Glu Gly Val Ala Tyr Ala Leu
                185                 190                 195
aag cag ctc aac ctc ccc aac gtg gtc atg tac atc gat gcc ggc cac          3257
Lys Gln Leu Asn Leu Pro Asn Val Val Met Tyr Ile Asp Ala Gly His
            200                 205                 210
ggt ggc tgg ctc ggc tgg gac gcc aac ctc aag ccc ggc gcc cag gag          3305
Gly Gly Trp Leu Gly Trp Asp Ala Asn Leu Lys Pro Gly Ala Gln Glu
            215                 220                 225
ctc gcc agc gtc tac aag tct gct ggt tcg ccc tcg caa gtc cgc ggt          3353
Leu Ala Ser Val Tyr Lys Ser Ala Gly Ser Pro Ser Gln Val Arg Gly
230                 235                 240                 245
atc tcc acc aac gtg gct ggt tgg aac gcc tg  gtaagacact ctatgtcccc       3405
Ile Ser Thr Asn Val Ala Gly Trp Asn Ala Trp
            250                 255
ctcgtcggtc aatggcgagc ggaatggcgt gaaatgcatg gtgctgacct tgatcttttt       3465
cccccttccta tag g gac cag gag ccc ggt gag ttc tcg gac gcc tcg gat       3515
                  Asp Gln Glu Pro Gly Glu Phe Ser Asp Ala Ser Asp
                              260                 265
gcc cag tac aac aag tgc cag aac gag aag atc tac atc aac acc ttt          3563
Ala Gln Tyr Asn Lys Cys Gln Asn Glu Lys Ile Tyr Ile Asn Thr Phe
270                 275                 280
```

FIGURE 11 (CONT'D)

SEQ ID NOs: 7 and 8   eg6 gene encoding CBHIIa

```
ggc gct gag ctc aag tct gcc ggc atg ccc aac cac gcc atc atc gac      3611
Gly Ala Glu Leu Lys Ser Ala Gly Met Pro Asn His Ala Ile Ile Asp
285                 290                 295                 300
act ggc cgc aac ggt gtc acc ggt ctc cgc gac gag tgg ggt gac tgg      3659
Thr Gly Arg Asn Gly Val Thr Gly Leu Arg Asp Glu Trp Gly Asp Trp
                305                 310                 315
tgc aac gtc aac ggc gcc ggc ttc ggt gtg cgc ccg act gcc aac act      3707
Cys Asn Val Asn Gly Ala Gly Phe Gly Val Arg Pro Thr Ala Asn Thr
            320                 325                 330
ggc gac gag ctc gcc gac gcc ttc gtg tgg gtc aag ccc ggt ggc gag      3755
Gly Asp Glu Leu Ala Asp Ala Phe Val Trp Val Lys Pro Gly Gly Glu
        335                 340                 345
tcc gac ggc acc agc gac tcg tcg gcg gcg cgc tac gac agc ttc tgc      3803
Ser Asp Gly Thr Ser Asp Ser Ser Ala Ala Arg Tyr Asp Ser Phe Cys
    350                 355                 360
ggc aag ccc gac gcc ttc aag ccc agc ccc gag gcc ggt acc tgg aac      3851
Gly Lys Pro Asp Ala Phe Lys Pro Ser Pro Glu Ala Gly Thr Trp Asn
365                 370                 375                 380
cag gcc tac ttc gag atg ctc ctc aag aac gcc aac ccg tcc ttc          3896
Gln Ala Tyr Phe Glu Met Leu Leu Lys Asn Ala Asn Pro Ser Phe
                385                 390                 395
taagctcctc gacggcttct tgctgtcagt cgctctgacg gtggtgtgct ggtggtgccc    3956
ctgctcctgc tgctgctgct ccgcggggag gggaggcaac gaaaatgaag tcctgcttca    4016
aaacaaaaca gaaacaagcg aggcgcggtg caatggtcgt gcgttcgtct tttttcatgt    4076
tcccttctag tgtagtagtt tgatagtcgt acataagggg tttcagaacc gtctctctgt    4136
ctcggtcttt ttgcgagttg ttgcgactcg tgattatggc ctttgttgct cgttgcggca    4196
gagtagaacc acagcgtgtt ggggtagcag cttgctccgt aggacgtagg gaaacaacct    4256
gagactctgg aattgcagtc agcctgcgtc gcccctctag gaaacgaagg ggagaaccag    4316
tagtggctgc agcttacaaa cgcgagcatg gtgaacatct ccgagaaaag ggagggatcc    4376
```

FIGURE 12

SEQ ID NOs: 9 and 10   eg2 gene encoding EGII

| | |
|---|---|
| 1 | tgctgctctgatgtgctgatgcacagcttccctcgcgattgccggcaggatctccaacc |
| 61 | ctctggatcggagcagacgatcagcgggcacaatggccagcttgccagcgttcaactcca |
| 121 | agttgacccgcttttatcacgcccaagctggacatgcacaggcttggcttctcgtgttcc |
| 181 | tacgatctgcacagtaggtttgactgctgatcttcgctttcctgtgcgcctcccctcc |
| 241 | ctcacgggtaccttatccttgcctgtaaccccgcgttatgtcaaacttgagtttgaccaa |
| 301 | tgctagcgcaaaagtacctacatagtactatgtaataaggtaggtacatacatcagtagg |
| 361 | cgtttatctagtaaattttggcttttttgaaactcaattgctcctctcctcgcctccacct |
| 421 | ctgcttggcaattgacaaccctggctgtgcctagaggtagcatcgacgatcaatcaaatc |
| 481 | taaagtattcgagattgacctttctgctctaattatattaattatccgcacaatgctgta |
| 541 | gtcattgactctcctttcaagttgccttctcgtttatgtatgtacaatgggcggtcatgc |
| 601 | ttcatgccaacagatggttctatcggaacaatgtttgactttctggtcgccccgtcgaac |
| 661 | tgttttgatttcgcacgggaagtgttcttaccaaagctaagtcgactcgtggagcttcgt |
| 721 | aacggccagtgatcgttgatcgcttttggaggagttgcgatggagcgagaccggctacga |
| 781 | gcacgttcgcaaaggcagcacgatagacgaccctccgtggcgccattcgggagatgcaca |
| 841 | tgacataagcatatcaatactcacctgaactcatcggccgatgcctcgcaggtagttaca |
| 901 | agacatatttgtgtgggtatattatcccaacccgtacctttgtcgcgtcatttcggtatg |
| 961 | tgctgatgcctacttagggagcaaagacgcctctcctcacctgcgggttacttacttact |
| 1021 | gtgcagcatggccttatgttctcccgggtcttgcttgcgcgaatgaacaaaaacgcccga |
| 1081 | agaaagccgcttcttcgagttgtgtctacccgaacataagaggttattgtcgcagaccg |
| 1141 | ccagcaaatgtcaacaacccacccacggcgttccagaaccttcgaaatatcatctagttt |
| 1201 | aagtttaaatgacggcccgagtcccagccgagattcccatattggccgataccagcgttc |
| 1261 | ccttgtttttccaaggttgtctcgtcaactggcgcatctgcctacaacgagatataatta |
| 1321 | ccgttttcttttgcaaaagggcatgcatggatgtatattatttatgcctgcagaacgaga |
| 1381 | agcaatcatggtgtaggttttgtgcggtatggagctaataatattgaacggatctctggt |
| 1441 | ccgtcctaaatcgttgaaacgctaggccaggaggacctgctcgacttggcgaacggaga |
| 1501 | tttccaggatgaaaggtcggaacatgtccatccgcggccagcctgaacacttttgctcgt |
| 1561 | ttccggaccatcgacccacgaaaacagtgcggttgctggcacagtcagcactcacgatgg |
| 1621 | cgatggtccagcccgttcccgcccgatgcccacttgcagcgcaactctccttcattcggc |
| 1681 | ggcccggcggtgtctggcctattagtacgatttggataccggcttggtcgccgccgcgg |
| 1741 | ttttcttggccgatacgggaatctcggtggtcccaactccacctgggcacgctctggtg |
| 1801 | ccaacatggaacttcgggatgccgctccgggcacagtcaagcgcttttaaaatacgacttt |
| 1861 | accccacaagaatcgaggcgtaacccggaattagggacacctggacggcgcaaccctgg |
| 1921 | accgaagggcctcgctaaccgggttcctggagccgcatgcgcggctgcccgcttcccgc |
| 1981 | tcttgagatgacacttcttttcagcgagggatggtcgggcagggaaatgatgtattataa |

FIGURE 12 (CONT'D)

SEQ ID NOs: 9 and 10  eg2 gene encoding EGII

```
2041       gaagcgagccgattccgaaggactcgaccccctctctcgccctgtgtccgccagctaatt
2101       acagcactccttctcgacttgaaacgcccgagATGAAGTCCTCCATCCTCGCCAGCGTCT
700                                         M  K  S  S  I  L  A  S  V 2161       TCGCCACGGGCGCCGTGGCTCAAAGTGGTCCGTGGCAGCAATGTGGTGGCATCGGATGGC
720         F  A  T  G  A  V  A  Q  S  G  P  W  Q  Q  C  G  G  I  G  W 2221       AAGGATCGACCGACTGTGTGTCGGGTTACCACTGCGTCTACCAGAATGATTGGTACAGCC
740         Q  G  S  T  D  C  V  S  G  Y  H  C  V  Y  Q  N  D  W  Y  S 2281       AGTGCGTGCCTGGCGCGGCGTCGACAACGCTCCAGACATCTACCACGTCCAGGCCCACCG
760         Q  C  V  P  G  A  A  S  T  T  L  Q  T  S  T  T  S  R  P  T 2341       CCACCAGCACCGCCCCTCCGTCGTCCACCACCTCGCCTAGCAAGGGCAAGCTCAAGTGGC
780         A  T  S  T  A  P  P  S  S  T  T  S  P  S  K  G  K  L  K  W 2401       TCGGCAGCAACGAGTCGGGCGCCGAGTTCGGGGAGGGCAACTACCCCGGCCTCTGGGGAA
800         L  G  S  N  E  S  G  A  E  F  G  E  G  N  Y  P  G  L  W  G 2461       AGCACTTCATCTTCCCGTCGACTTCGGCGATTCAGgtacgggccaataataatatattat
820         K  H  F  I  F  P  S  T  S  A  I  Q
2521       tatagcaggcaggagggagcaggagaagaagggaggggcaggtggccaacaatcggaaga
2581       agaccgggaggcactgaccgttgattcctttgtgtaatagACGCTCATCAATGATGGATA
861                                                 T  L  I  N  D  G  Y 2641       CAACATCTTCCGGATCGACTTCTCGATGGAGCGTCTGGTGCCCAACCAGTTGACGTCGTC
881         N  I  F  R  I  D  F  S  M  E  R  L  V  P  N  Q  L  T  S  S 2701       CTTCGACGAGGGCTACCTCCGCAACCTGACCGAGGTGGTCAACTTCGTGACGAACGCGGG
901         F  D  E  G  Y  L  R  N  L  T  E  V  V  N  F  V  T  N  A  G 2761       CAAGTACGCCGTCCTGGACCCGCACAACTACGGCCGGTACTACGGCAACGTCATCACGGA
921         K  Y  A  V  L  D  P  H  N  Y  G  R  Y  Y  G  N  V  I  T  D

2821       CACGAACGCGTTCCGGACCTTCTGGACCAACCTGGCCAAGCAGTTCGCCTCCAACTCGCT
```

FIGURE 12 (CONT'D)

SEQ ID NOs: 9 and 10  eg2 gene encoding EGII

```
941          T  N  A  R  T  F  W  T  N  L  A  K  Q  F  A  S  N  S  L

2881    CGTCATCTTCGACACCAACAACGAGTACAACACGATGGACCAGACCCTGGTGCTCAACCT
961          V  I  F  D  T  N  N  E  Y  N  T  M  D  Q  T  L  V  L  N  L

2941    CAACCAGGCCGCCATCGACGGCATCCGGGCCGCCGGCGCGACCTCGCAGTACATCTTCGT
981          N  Q  A  A  I  D  G  I  R  A  A  G  A  T  S  Q  Y  I  F  V

3001    CGAGGGCAACGCGTGGAGCGGGGCCTGGAGCTGGAACACGACCAACACCAACATGGCCGC
1001         E  G  N  A  W  S  G  A  W  S  W  N  T  T  N  T  N  M  A  A

3061    CCTGACGGACCCGCAGAACAAGATCGTGTACGAGATGCACCAGTACCTCGACTCGGACAG
1021         L  T  D  P  Q  N  K  I  V  Y  E  M  H  Q  Y  L  D  S  D  S

3121    CTCGGGCACCCACGCCGAGTGCGTCAGCAGCAACATCGGCGCCCAGCGCGTCGTCGGAGC
1041         S  G  T  H  A  E  C  V  S  S  N  I  G  A  Q  R  V  V  G  A

3181    CACCCAGTGGCTCCGCGCCAACGGCAAGCTCGGCGTCCTCGGCGAGTTCGCCGGCGGCGC
1061         T  Q  W  L  R  A  N  G  K  L  G  V  L  G  E  F  A  G  G  A

3241    CAACGCCGTCTGCCAGCAGGCCGTCACCGGCCTCCTCGACCACCTCCAGGACAACAGCGA
1081         N  A  V  C  Q  Q  A  V  T  G  L  L  D  H  L  Q  D  N  S  E

3301    GGTCTGGCTGGGTGCCCTCTGGTGGGCCGCCGGTCCCTGGTGGGGCGACTACATGTACTC
1101         V  W  L  G  A  L  W  W  A  A  G  P  W  W  G  D  Y  M  Y  S

3361    GTTCGgtaagtttctcccttgttcttggcttttcccccagtaagggagtcaggcaacat
1121         F
3421    gcccaagaccggctcggcttcgcttcaaggcgttcgttgtacacactgaagagttccaac
3481    ttccaaccctgttcgtgtcctccgatcagcttcgacggggtgaagggggaagggatttgg
3541    gagtgaggtggaggtcaaaaggagggatatccccagatctccacaaacggccctgagcca
3601    acaacagcctctggggtcaaaatgggcgccaaccatacggtcattcactcaggacacctg
3661    ctaacgcgtctctttttttgtttccagAGCCTCCTTCGGGCACCGGCTATGTCAACTAC
1221                                 E  P  P  S  G  T  G  Y  V  N  Y
3721    AACTCGATCCTAAAGAAGTACTTGCCGTAAgggcatgcagcaaggtcgagcgagcatta
```

FIGURE 12 (CONT'D)

SEQ ID NOs: 9 and 10   eg2 gene encoding EGII

```
1241    N  S  I  L  K  K  Y  L  P  *
3781    ttcagggccatctgcttgtgtcggcaggcatcacgtcaacccatcgaatcggacagcgga
3841    atgctccgagatgccatacactaagtctggtgatgacgtgagaatgctggccctggtcgg
3901    gggttaccgccaacaaaaagcacccggacgctgccgcgcccggataccatggtttcatgt
3961    acatattggttctttgctttcttacggggggggggggggggggggggctctgcagcgttgc
4021    tgagcgattcgtttccaagtatatactttgtctggaattgaattttgagtgacattgacc
4081    caatcaaccagctcggtgtgctcacctcccgttaccccccctcttctcccctgctcggc
4141    ttggctttcctctccggtgtggagcacggccacggcggtcccaatccatataagatcgat
4201    ggtatactatggtatacactagcttgggaataaactaatccatacgctaactaatggacg
4261    gattatcctaagggtcaccggctcaccgttggatataacacctaggatacgggagagctg
4321    atagaaagggatgtactccgtattgtactgtacaatacaaagtacagatagcacacgaag
4381    tacggtaggtggtcccgcctagtccggaccaacaatagaacatgcgttcctggggacctg
4441    caggaaagaaggggggggggttgccaagacgcccggggttcaaagaaagccccgggccg
4501    ccgatgagatgagacggacgccggcccaaggagaggccggtggtcgatcctgcaaatgcc
4561    agcaaaaaaatccataccataatccagtcaactttcgtcacactcctgtgaaacgagct
4621    ggagggactgctggaaaggttttgcaggttaatcactgtatgtggagcatgccgtaccta
4681    ctgtgcttcgttaacagatagagttccagttgaacacacaaagttctgccccgcctgcca
4741    gacgtgaaaagaagctcctccggggggagctttaggcaactgggagggctctctcccaggt
4801    tcatggtgtctgctcttcttcaaattttatgctgccacccatttgacagaggtgtgca
4861    caccgttgccaggtcttgccatccggcaaaaagcagaaaagtcgacccatcgcctaagaa
4921    aggcggtcggaaggggatcggatgctcattgcggcttagcgtctgcccattctgacgctg
4981    cccattgttttgtgtcgcattcgtcttcggatgtcggatcaagagtcccggattttttcc
5041    cctgtgcttccagcctaatctgagcgggagctggctcggtttcgagtggagttgccttgt
5101    tggtggagcagcaaccagccaattcactcccccgcattttcgcggccgcccaggcatccc
5161    cggcatgcgtttgggcggtaactactccgtactgggtaggtgaaattggttctcccgtc
5221    gcaggaggctcgtgctcggtcaggggagaacaaagtccaactgctccttcctggcaacaa
5281    tgagaggggttctattgccaacgttgcacgaaaggagcagccacaaaacccaaaagcag
5341    gttaccttactgtacctgagcttgaacgtcgcgtagcattggagctctcgtctaccggcg
5401    gcgtcacactccattggcaggtcaaggcagtcagtggcagcgacccaacaacgtcaatgc
5461    ttgttaccccagaattaccccgggctgcaacactgcaggggccgccgccgatgttgatca
5521    ccggttgattacttctcggcccgcaaccgggagatgagaagcagaactttgttctccttt
5581    caaaaaggacctgacttgcggggaacgcactgccggcagtggagtggatgcacgctagtt
5641    atatgtttcccgccatccccagtccgcccgtcgcgtccgtgaggctcagtttggcttccc
5701    gtgccgccgacaaacgagcggtgcataattacatttcgctccatgtaccgtgcaccctcc
5761    ccgttcgcgaccgtagta
```

FIGURE 13

SEQ ID NOs: 11 and 12  bgl1 gene encoding BGL

```
   1    ccggcctccagttccaggagcttggctctgccgacatactgtgtacactaggaattctct
  61    tatgcggggtgtgcgcggggaaatgttggggaactcgagttgggtcatgtggacaagacc
 121    aatgggagctgacatcattgtgcgacccgttaaaccggaagctacaacaacattctggat
 181    tctacactagtggaagaggtaagtaattgacgacaagcaagaagcattgccatgttctgc
 241    gaaggatgcgggtgttttgcatgagcaggaagctgtggcttttttagtgctcctttgtgc
 301    tcgccgggcgcgcagaacactaccgaaacgcaggggactgcgtgcctctggggtcgaatg
 361    ccgatccccatcttcacattccaccatcgtgttctgttaacgaagccggagcggcggga
 421    actcgaagctccactacgtatggatacttgggaccgtacggagtgtgttggtacggatgc
 481    ctgcacaagtgttgtgcttcctacgaagacgccaacccacataatacacaaaagctgttg
 541    taagtcgagttacctcaggcacgttcgggcaactcgggcaacctgacgagatttccccgc
 601    cattccgccaagaggccggcgcctgccctgattaggcagctcttggaacaatactatgta
 661    gaatggaagctccatccatagtcagctccattggcggtcccagtgatctcgatggctgga
 721    tggctgctctgtacggtacatacatagtaagttctcgccttgagagcccaattcgctgca
 781    atagcatctttccccgcagtgcgccggccgccctgggtcccgctccacaatgaccttgct
 841    tctggagcttctcgacgaacagatcggcccgtttcttctccacaccaatccgaaccagtc
 901    gggagcatggctgcggatgcgacgcagccttccttcgcgctgtacaaacagctccgggaa
 961    cgtcgactggtatgtacggactacagtaagtacactacgagtgcacatactgacgaatac
1021    cggcctcagaggaacctggcaggaccctaccccacacgaaaccacagcgagaaagcgcaa
1081    tggatcagtaactactgcgaagtaaccgtggtcccgggcaaaggatctgagggccgatcg
1141    ctcgtggggctgcgaggcgagggagagcaaacaagccagtcctcccgcgaacctggaaaa
1201    tcacttataaacacacgtcaccggcgccggggtgcgcgccatgtgtcacctccaggctcc
1261    tcccgggcgatgatctctgccggtgccatcaatcatctcggttcgccgcagctgcttctt
1321    tctgtgcagtgaacgctctcaaactgcaacgacgctgtccgacatgaaggctgctgcgct
1381    ttcctgcctcttcggcagtacccttgccgttgcaggcgccattgaatcgagaaaggtatg
1441    gacgggctttcgtcaaagactcgctccccgatcaacttccccttcatccagaccaccc
1501    aaccctcccagtcctgcttcgagcacgatctcttcgggcagcacccccacccacatccact
1561    cagattagcggcgacaccgttgactgttgcaatccgcaatcgacATGCAACTTCCAGCCG
                                                   M   Q   L   P   A
1621    CAGCCCAATGGCTGCTCACGCTTCCCGCGAAAGCCTCACTTGCTGACAATCATCGTCAGG
         A   A   Q   W   L   L   T   L   P   A   K   A   S   L   A   D   N   H   R   Q
1681    TTCACCAGAAGCCCCTCGCGAGATCTGAACCTTTTTACCCGTCGCCATGGATGAATCCCA
         V   H   Q   K   P   L   A   R   S   E   P   F   Y   P   S   P   W   M   N   P
1741    ACGCCGACGGCTGGGCGGAGGCCTATGCCCAGGCCAAGTCCTTTGTCTCCCAAATGACTC
         N   A   D   G   W   A   E   A   Y   A   Q   A   K   S   F   V   S   Q   M   T
```

FIGURE 13 (CONT'D)

SEQ ID NOs: 11 and 12   bgl1 gene encoding BGL

```
1801      TGCTAGAGAAGGTCAACTTGACCACGGGAGTCGGgtaagttttgtcattttgtccaggta
           L   L   E   K   V   N   L   T   T   G   V   G
                                                                    C1 Bgl1 236 for
1861      acatgcaaatggttctgctaacaataacttaccgtagCTGGGGGGCTGAGCAGTGCGTCG
                                                  W   G   A   E   Q   C   V
1921      GCCAAGTGGGCGCGATCCCTCGCCTTGGACTTCGCAGTCTGTGCATGCATGACTCCCCTC
           G   Q   V   G   A   I   P   R   L   G   L   R   S   L   C   M   H   D   S   P
1981      TCGGCATCCGAGGAGCCGACTACAACTCAGCGTTCCCCTCTGGCCAGACCGTTGCTGCTA
           L   G   I   R   G   A   D   Y   N   S   A   F   P   S   G   Q   T   V   A   A
2041      CCTGGGATCGCGGTCTGATGTACCGTCGCGGCTACGCAATGGGCCAGGAGGCCAAAGGCA
           T   W   D   R   G   L   M   Y   R   R   G   Y   A   M   G   Q   E   A   K   G
2101      AGGGCATCAATGTCCTTCTCGGACCAGTCGCCGGCCCCCTTGGCCGCATGCCCGAGGGCG
           K   G   I   N   V   L   L   G   P   V   A   G   P   L   G   R   M   P   E   G
2161      GTCGTAACTGGGAAGGCTTCGCTCCGGATCCCGTCCTTACCGGCATCGGCATGTCCGAGA
           G   R   N   W   E   G   F   A   P   D   P   V   L   T   G   I   G   M   S   E
                                                                          C1BglI 682 rev
2221      CGATCAAGGGCATTCAGGATGCTGGCGTCATCGCTTGTGCGAAGCACTTTATTGGAAACG
           T   I   K   G   I   Q   D   A   G   V   I   A   C   A   K   H   F   I   G   N
2281      AGCAGGgtgagtagtcaaagacgggccgtctcggacccgcggcttcaagctgctgactct
           E   Q
2341         gctgcagAGCACTTCAGACAGGTGCCAGAAGCCCAGGGATACGGTTACAACATCAGCGAA
                     E   H   F   R   Q   V   P   E   A   Q   G   Y   G   Y   N   I   S   E
2401      ACCCTCTCCTCCAACATTGACGACAAGACCATGCACGAGCTCTACCTTTGGCCGTTTGCC
           T   L   S   S   N   I   D   D   K   T   M   H   E   L   Y   L   W   P   F   A
2461      GATGCCGTCCGGGCCGGCGTCGGCTCTGTCATGTGCTCGTACCAGCAGGTCAACAACTCG
           D   A   V   R   A   G   V   G   S   V   M   C   S   Y   Q   Q   V   N   N   S
2521      TACGCCTGCCAGAACTCGAAGCTGCTGAACGACCTCCTCAAGAACGAGCTTGGGTTTCAG
           Y   A   C   Q   N   S   K   L   L   N   D   L   L   K   N   E   L   G   F   Q
2581      GGCTTCGTCATGAGCGACTGGCAGGCACAGCACACTGGCGCAGCAAGCGCCGTGGCTGGT
           G   F   V   M   S   D   W   Q   A   Q   H   T   G   A   A   S   A   V   A   G
2641      CTCGATATGTCCATGCCGGGCGACACCCAGTTCAACACTGGCGTCAGTTTCTGGGGCGCC
           L   D   M   S   M   P   G   D   T   Q   F   N   T   G   V   S   F   W   G   A
2701      AATCTCACCCTCGCCGTCCTCAACGGCACAGTCCCTGCCTACCGTCTCGACGACATGGCC
           N   L   T   L   A   V   L   N   G   T   V   P   A   Y   R   L   D   D   M   A
```

FIGURE 13 (CONT'D)

SEQ ID NOs: 11 and 12    bgl1 gene encoding BGL

```
2761    ATGCGCATCATGGCCGCCCTCTTCAAGGTCACCAAGACCACCCACCTGGAACCCATCAAC
         M   R   I   M   A   A   L   F   K   V   T   K   T   T   H   L   E   P   I   N
2821    TTCTCCTTCTGGACCGACGACACTTATGGCCCGATCCACTGGGCCGCCAAGCATGGCTAC
         F   S   F   W   T   D   D   T   Y   G   P   I   H   W   A   A   K   H   G   Y
2881    CAGAAGATTAATTCCCACGTTGACGTCCGCGCCGACCACGGCAACCTCATCCGGGAGATT
         Q   K   I   N   S   H   V   D   V   R   A   D   H   G   N   L   I   R   E   I
2941    GCCGCCAAGGGTACGGTGCTGCTGAAGAATACCGGCTCTCTACCCCTGAACAAGCCAAAG
         A   A   K   G   T   V   L   L   K   N   T   G   S   L   P   L   N   K   P   K
3001    TTCGTGGCCGTCATCGGCGAGGATGCTGGGTCGAGCCCCAACGGGCCCAACGGCTGCAGC
         F   V   A   V   I   G   E   D   A   G   S   S   P   N   G   P   N   G   C   S
3061    GACCGCGGCTGTAACGAAGGCACGCTCGCCATGGGCTGGGGATCCGGCACAGCCAACTAT
         D   R   G   C   N   E   G   T   L   A   M   G   W   G   S   G   T   A   N   Y
3121    CCGTACCTCGTTTCCCCCGACGCCGCGCTCCAGGCCCGGGCCATCCAGGACGGCACGAGG
         P   Y   L   V   S   P   D   A   A   L   Q   A   R   A   I   Q   D   G   T   R
3181    TACGAGAGCGTCCTGTCCAACTACGCCGAGGAAAAGACAAAGGCTCTGGTCTCGCAGGCC
         Y   E   S   V   L   S   N   Y   A   E   E   K   T   K   A   L   V   S   Q   A
3241    AATGCAACCGCCATCGTCTTCGTCAATGCCGACTCAGGCGAGGGCTACATCAACGTGGAC
         N   A   T   A   I   V   F   V   N   A   D   S   G   E   G   Y   I   N   V   D
3301    GGTAACGAGGGCGACCGTAAGAACCTGACTCTCTGGAACAACGGTGATACTCTGGTCAAG
         G   N   E   G   D   R   K   N   L   T   L   W   N   N   G   D   T   L   V   K
3361    AACGTCTCGAGCTGGTGCAGCAACACCATCGTCGTCATCCACTCGGTCGGCCCGGTCCTC
         N   V   S   S   W   C   S   N   T   I   V   V   I   H   S   V   G   P   V   L
3421    CTGACCGATTGGTACGACAACCCCAACATCACGGCCATTCTCTGGGCTGGTCTTCCGGGC
         L   T   D   W   Y   D   N   P   N   I   T   A   I   L   W   A   G   L   P   G
3481    CAGGAGTCGGGCAACTCCATCACCGACGTGCTTTACGGCAAGGTCAACCCCGCCGCCCGC
         Q   E   S   G   N   S   I   T   D   V   L   Y   G   K   V   N   P   A   A   R
3541    TCGCCCTTCACTTGGGGCAAGACCCGCGAAAGCTATGGCGCGGACGTCCTGTACAAGCCG
         S   P   F   T   W   G   K   T   R   E   S   Y   G   A   D   V   L   Y   K   P
3601    AATAATGGCAATGGTGCGCCCCAACAGGACTTCACCGAGGGCGTCTTCATCGACTACCGC
         N   N   G   N   G   A   P   Q   Q   D   F   T   E   G   V   F   I   D   Y   R
3661    TACTTCGACAAGGTTGACGATGACTCGGTCATCTACGAGTTCGGCCACGGCCTGAGCTAC
         Y   F   D   K   V   D   D   D   S   V   I   Y   E   F   G   H   G   L   S   Y
3721    ACCACCTTCGAGTACAGCAACATCCGCGTCGTCAAGTCCAACGTCAGCGAGTACCGGCCC
         T   T   F   E   Y   S   N   I   R   V   V   K   S   N   V   S   E   Y   R   P
3781    ACGACGGGCACCACGGCCCAGGCCCCGACGTTTGGCAACTTCTCCACCGACCTCGAGGAC
```

FIGURE 13 (CONT'D)

SEQ ID NOs: 11 and 12    bgl1 gene encoding BGL

```
                T  T  G  T  T  A  Q  A  P  T  F  G  N  F  S  T  D  L  E  D
3841  TATCTCTTCCCCAAGGACGAGTTCCCCTACATCTACCAGTACATCTACCCGTACCTCAAC
       Y  L  F  P  K  D  E  F  P  Y  I  Y  Q  Y  I  Y  P  Y  L  N
3901  ACGACCGACCCCCGGAGGGCCTCGGCCGATCCCCACTACGGCCAGACCGCCGAGGAGTTC
       T  T  D  P  R  R  A  S  A  D  P  H  Y  G  Q  T  A  E  E  F
3961  CTCCCGCCCCACGCCACCGATGACGACCCCCAGCCGCTCCTCCGGTCCTCGGGCGGAAAC
       L  P  P  H  A  T  D  D  D  P  Q  P  L  L  R  S  S  G  G  N
4021  TCCCCCGGCGGCAACCGCCAGCTGTACGACATTGTCTACACAATCACGGCCGACATCACG
       S  P  G  G  N  R  Q  L  Y  D  I  V  Y  T  I  T  A  D  I  T
4081  AATACGGGCTCCGTTGTAGGCGAGGAGGTACCGCAGCTCTACGTCTCGCTGGGCGGTCCC
       N  T  G  S  V  V  G  E  E  V  P  Q  L  Y  V  S  L  G  G  P
4141  GAGGATCCCAAGGTGCAGCTGCGCGACTTTGACAGGATGCGGATCGAACCCGGCGAGACG
       E  D  P  K  V  Q  L  R  D  F  D  R  M  R  I  E  P  G  E  T
4201  AGGCAGTTCACCGGCCGCCTGACGCGCAGAGATCTGAGCAACTGGGACGTCACGGTGCAG
       R  Q  F  T  G  R  L  T  R  R  D  L  S  N  W  D  V  T  V  Q
4261  GACTGGGTCATCAGCAGGTATCCCAAGACGGCATATGTTGGGAGGAGCAGCCGGAAGTTG
       D  W  V  I  S  R  Y  P  K  T  A  Y  V  G  R  S  S  R  K  L
4321  GATCTCAAGATTGAGCTTCCTTGAATGAGTTTCATCAGGGGCTGCAGAGGGATGGTAACA
       D  L  K  I  E  L  P  *
4381  CGTTCTTAATCAGAAGTATGATGGAGAAAAGCACTTGGCAAGTTCCGGTGAGCAAAAAGA
4441  AGGCACTTATTAAGTGTAGGGCGGTGTTCTATGTTTAATAGGTGCTATGTTTACATATAA
4501  TTAGTATATAATGATTTAATAATTATGTTTAGCAGTTGCTAATGTCGTAAATTTCGGCGT
4561  GTGATGACTGCTACAACACTGGTTCTGTCTTCTAGTCGCCATTGTTAATTATGAAGGTTA
4621  TTGTCTACAATTTCTAATACCTTATGGATGATTGCCCAGCTGGTTTCAAACTCGTTACGC
4681  GCAAATGGTACGATTGAGGTATTATTCATTGTAAGTACCTCCGTACAGCGTCCCCAACTA
4741  TTTCCATTCACGAGATGCCTCGCTTTTCGGTGCTTTCGGAACAGGGCTGGCAGCGGATCA
4801  TGGCGCGATCAAAACATGGCGAGCAGCTGTCCAGGACGGAGGACAGGTTGGGGACTGATG
4861  CCTCCCGGACGCATTAAGGTCAGAAGATAGACACGTTTTACACAGCGTTGAGACCGACAA
4921  GCCACATTAGGCAGCGCCGGTTGCACCACCGCCGTCACGGGCAACGGTTCAATCAATCGA
4981  CAACAGTGGAAGACAAAGTACTGAAGATCAGGTATTAATAGTGTGAGAGAGAAACAGACG
5041  GTGGAACTAGGGTGCTAATATTTCTCTTGATTTCGGTGTCCATGGTAGTACAGAACACAA
5101  GAAAAGAAGGAGGAGTGAGCGGAGAAGGAGGAGGGGGAAGCCAGAAAAAGAACATGAA
5161  AAAGCATACACATTGGAGTCGGTCAGTCGGTTGATTGGTTTGGTAGAGAGCGAAAAAGCA
5221  AGCGTCACCTGTAGGATTCGAACCTACGCTCCCGAAGGAACTGCCTAAGAACGCTAAGCA
```

FIGURE 13 (CONT'D)

SEQ ID NOs: 11 and 12    bgl1 gene encoding BGL

```
5281       AGGTTAGCAGGGCAGCGCGTTAACCACTCCGCCAAAGTGACTGTCGTTGATCATGGTCGA
5341       ATTCAAGTAGCTTATAGGAGTTCAACCAGATCACAAATGCATAGGTGCTCGTAGAACGGT
5401       CTAAGTATGAGTTGATTATAAGCAACCGAATGGCTCTCAGCGGCAACACCGTAGCTGAAG
5461       TAACAAAACGCACCTTTGGTTACTTTCTGACTATAAAAATGGGATATTTGGAAATGACCA
5521       CCCGATAAGGTGTCAAATTCTAAATGACTGTCTGGGTGTGAAGATGTTACTGTGGTTCCA
5581       CCACGAACCAGTTTTAGTATCCGCATGCTTCAGTCTCTGCGCCTCGACAGGCGGAGGGTG
5641       TGTGTTAGATCAGAATCGATGTGACGCTGTGACCGCGAGGCTCTCGAGCCTAGGTGCGGT
5701       AGTTCTGTTCAAAAAGAAGTGTGTGGCCGGGTTTGGGCGCCCTTATAGCCTACCATCCTG
5761       GCTGTGGTTCCCGAGCGGGAGCCGGTTCTCCGTTTTGGTTCCGATAAAGTGTCATATCTG
5821       CCTCCCGGTTTCGCATCTAATTTCTGACTTCGTTCGGGACCTCTGGAGACGTAGGGATAG
5881       GTATGGGATATGCCCGGCATTTCGTAAATGTCCATAGTCTCTTTCGGGACGAGGCGGCAA
5941       GCTCTCAGAGCTATCTAAGCTTAACCAACCCCTGATCCTTAACCCTCCCAGACCACACCT
6001       CCTGGGAGAATAAACCGGGCTCCAAGATCGAAATCGAAATCAGTGCGCGAACTTGAAATC
```

FIGURE 14

SEQ ID NOs: 13 and 14   eg5 gene encoding EGV

```
atg cat ctc tcc gcc acc acc ggg ttc ctc gcc ctc ccg gcc ctg gcc      48
Met His Leu Ser Ala Thr Thr Gly Phe Leu Ala Leu Pro Ala Leu Ala
1               5                   10                  15 ctg gcc cag ctc tcg ggc agc ggc cag acg acc cgg tac tgg gac tgc      96
Leu Ala Gln Leu Ser Gly Ser Gly Gln Thr Thr Arg Tyr Trp Asp Cys
                20                  25                  30 tgc aag ccg agc tgc gcc tgg ccc ggc aag ggc ccc tcg tct ccg gtg     144
Cys Lys Pro Ser Cys Ala Trp Pro Gly Lys Gly Pro Ser Ser Pro Val
            35                  40                  45 cag gcc tgc gac aag aac gac aac ccg ctc aac gac ggc ggc tcc acc     192
Gln Ala Cys Asp Lys Asn Asp Asn Pro Leu Asn Asp Gly Gly Ser Thr
        50                  55                  60 cgg tcc ggc tgc gac gcg ggc ggc agc gcc tac atg tgc tcc tcc cag     240
Arg Ser Gly Cys Asp Ala Gly Gly Ser Ala Tyr Met Cys Ser Ser Gln
65                  70                  75                  80 agc ccc tgg gcc gtc agc gac gag ctg tcg tac ggc tgg gcg gcc gtc     288
Ser Pro Trp Ala Val Ser Asp Glu Leu Ser Tyr Gly Trp Ala Ala Val
                85                  90                  95 aag ctc gcc ggc agc tcc gag tcg cag tgg tgc tgc gcc tgc tac gag     336
Lys Leu Ala Gly Ser Ser Glu Ser Gln Trp Cys Cys Ala Cys Tyr Glu
                100                 105                 110 ctg acc ttc acc agc ggg ccg gtc gcg ggc aag aag atg att gtg cag     384
Leu Thr Phe Thr Ser Gly Pro Val Ala Gly Lys Lys Met Ile Val Gln
            115                 120                 125
```

FIGURE 14 (CONT'D)

SEQ ID NOs: 13 and 14   eg5 gene encoding EGV

```
gcg acc aac acc ggt ggc gac ctg ggc gac aac cac ttt gac ctg gcc      432
Ala Thr Asn Thr Gly Gly Asp Leu Gly Asp Asn His Phe Asp Leu Ala
        130                 135                 140 gtgagttgcc tccccttctc cccggaccgc tcagattaga tgagattaga ctttgctcgt    492
aaatcggtcc aagattccct tgactgacca acaaacatca tacgggcag atc ccc ggt    550
                                                    Ile Pro Gly
                                                        145 ggc ggt gtc ggt att ttc aac g gtaagctggt gccccggac ccctccccgg        602
Gly Gly Val Gly Ile Phe Asn
        150 acccctcccc cttttcctcc agcgagccga gttgggatcg ccgagatcga gaactcacac    662 aacttctctc tcgacag cc tgc acc gac cag tac ggc gct ccc ccg aac        711
                    Ala Cys Thr Asp Gln Tyr Gly Ala Pro Pro Asn
                                        160                 165 ggc tgg ggc gac cgc tac ggc ggc atc cat tcc aag gaa gag tgc gaa      759
Gly Trp Gly Asp Arg Tyr Gly Gly Ile His Ser Lys Glu Glu Cys Glu
                170                 175                 180 tcc ttc ccg gag gcc ctc aag ccc ggc tgc aac tgg cgc ttc gac tg       806
Ser Phe Pro Glu Ala Leu Lys Pro Gly Cys Asn Trp Arg Phe Asp Trp
        185                 190                 195 gtacgttgct ttgacatacc ggaacccaat tcctccaacc ccccccttt tctccccca     866 ctccgggggt agtcggaatg tcgcgactga ccctatttca g g ttc caa aac gcc      920
                                               Phe Gln Asn Ala
                                                       200
```

FIGURE 14 (CONT'D)

SEQ ID NOs: 13 and 14   eg5 gene encoding EGV

```
gac aac ccg tcg gtc acc ttc cag gag gtg gcc tgc ccg tcg gag ctc      968
Asp Asn Pro Ser Val Thr Phe Gln Glu Val Ala Cys Pro Ser Glu Leu
            205                 210                 215 acg tcc aag agc ggc tgc tcc cgt taa                                  995
Thr Ser Lys Ser Gly Cys Ser Arg
            220                 225
```

FIGURE 15

SEQ ID NOs: 15 and 16   eg7 encoding EG VI

| | |
|---|---|
| 1 | GCGCTTCCGGCCTGGGCGAGTAAAATGACGGAAGCCgggccccgtccgactgcgtttgtc |
| 61 | ccaactcggaagcaggcatcgttttttgggcgggaggaagcgttgcaacacgcactatcg |
| 121 | ccaaggtggactcggcgcaatctggaggttcggcccgcggaggacggaatccgggctgaa |
| 181 | tctgcgcaaaggctgaccctgcgatggtgggaaaatgtaaatatgtgaagttataggcat |
| 241 | ataggactcagcgatgacatggaaattgcagaggcatgtgggatttcagcgtttggcatg |
| 301 | cattggtcggatctctcgccttgtctgatgtgatcccgccggaggtgtttcggtctctgg |
| 361 | ggaagggaccccccctggcccccacctgccccgcatcatgcctcgccacgactcccgcg |
| 421 | cgccgaggaagaacttcgggtctttgtgacgggagattccactgagtgagcattggccaa |
| 481 | ccaagcacacaattactccgtacatacacagtacttctgactccgtaaagtaaaccgtgt |
| 541 | gtttcaaagatcggtaatccgtaacaggtactccgtatctaaggtaaatttaccctgtgc |
| 601 | acggagcagaacctgaacttcttccccctcttactcgagtagtcaccctactccaacca |
| 661 | gcggcttttcaactcgcaaagtcttgtttataacagtgcatatacctgcatttcgtatct |
| 721 | cgctagtgtaaagacgaccacacgcggacaaagaaagaaaaatccaattgcccgatggct |
| 781 | cttagtttgaggacagcagcgaaggactacactgcgccgtagtgaccaggccaagaaacg |
| 841 | cgaatcgtatattaacggcaaatcaaaatggattatatgccatttcgcttccgggttgcg |
| 901 | tgctcgtccgaagtctggtgccgatcgattgcgaaccccggaatcgcgggatgattcct |
| 961 | acagccgccgaaagggggggggggaggggggtctggacgggacgtgcataacttcgaa |
| 1021 | tttctagaatattgcggattgggttcccttcagccctgcgagcgcgccccttctggaac |
| 1081 | cgcacccttcaccggttccacacacagaggacatgggtggaaatgtgtacctgacggttg |
| 1141 | cccctttgggacagtggagaggcggatgttcggataaccatccggagccgcagtgtcgac |
| 1201 | caagatcttggcttaccatcgacaccaacatgcggactcgtccctcagtcatggagcctt |
| 1261 | ggctcgcggagcctccgttcgaagcggctatcccgtcctgccagcggaggatctcgtacc |
| 1321 | gcttccgcgaactgtgaatgtcctgggtataagagcatggcgcgaccttgtctcgtcagg |
| 1381 | aacggggaggaggagggcttggttagggtcgcgttcgtttggagattgctgagctctgag |
| 1441 | ccttcggtccttggatccctgcggtccccggtctcctctctctctctctctctctctctc |
| 1501 | tctctctcttcttcccacgctcgttcgacagacgcctcccttcttcgctctcctttccc |
| 1561 | tcgcacgtagcacactaatagtgcaccATGCGCGTCTCTAGTTTGGTCGCGGCCCTTGCT |
| |                              M   R   V   S   S   L   V   A   A   L   A |
| 1621 | ACCGGTGGTCTTGTCGCCGCCACGCCTAAGCCCAAGGGGTCGTCGCCCCCTGGGGCCGTG |
| |    T   G   G   L   V   A   A   T   P   K   P   K   G   S   S   P   P   G   A   V |
| 1681 | GACGCGAACCCTTTCAAGGGCAAGACGCAGTTCGTCAACCCGGCATGGGCGGCCAAGCTG |
| |    D   A   N   P   F   K   G   K   T   Q   F   V   N   P   A   W   A   A   K   L |

FIGURE 15 (CONT'D)

SEQ ID NOs: 15 and 16   eg7 encoding EG VI

```
1741    GAACAGACCAAAAAGGCGTTCCTGGCCAGGAACGACACCGTCAATGCCGCCAAGACGGAG
         E  Q  T  K  K  A  F  L  A  R  N  D  T  V  N  A  A  K  T  E

1801    AAGGTCCAGCAGACCAGCTCGTTCGTCTGGGTCTCGAGGATCGCCGAGCTCTCCAACATC
         K  V  Q  Q  T  S  S  F  V  W  V  S  R  I  A  E  L  S  N  I

1861    GACGACGCCATCGCGGCTGCCCGCAAGGCGCAGAAGAAGACGGGCAGGAGGCAGATCGTC
         D  D  A  I  A  A  A  R  K  A  Q  K  K  T  G  R  R  Q  I  V

1921    GGCCTGGTGCTCTACAACCTTCCGGACCGCGACTGCAGCGCGGGCGAGAGCGCGGGCGAG
         G  L  V  L  Y  N  L  P  D  R  D  C  S  A  G  E  S  A  G  E

1981    CTCAGCAGCGACAAGAACGGGCTCGAGATCTACAAGACTGAGTTCGTCAAGCCCTTCGCC
         L  S  S  D  K  N  G  L  E  I  Y  K  T  E  F  V  K  P  F  A

2041    GACAAGGTGGCGGCCGCAAAGGACCTCGACTTCGCCATCGTCCTGGAGCCCGACTCGCTG
         D  K  V  A  A  A  K  D  L  D  F  A  I  V  L  E  P  D  S  L

2101    GCCAACCTGGTCACCAACCTGGGCATCGAGTTCTGCGCCAACGCCGCCCCCGTCTACCGC
         A  N  L  V  T  N  L  G  I  E  F  C  A  N  A  A  P  V  Y  R

2161    GAGGGCATCGCCTATGCCATCTCCAGCCTTCAGCAGCCAAACGTGCACTTGTACATCGAT
         E  G  I  A  Y  A  I  S  S  L  Q  Q  P  N  V  H  L  Y  I  D

2221    GCTGCCCACGGCGGCTGGCTCGGCTGGGACGACAACCTGCCGCTGGCCGCCAAGGAGTTT
         A  A  H  G  G  W  L  G  W  D  D  N  L  P  L  A  A  K  E  F

2281    GCCGAGGTGGTCAAGCTTGCCGGCGAGGGCAAGAAGATCCGCGGCTTCGTCACCAACGTG
         A  E  V  V  K  L  A  G  E  G  K  K  I  R  G  F  V  T  N  V

2341    TCCAACTACAACCCCTTCCACGCCGTCGTGCGCGAGAACTTTACCGAGTGGAGCAACTCG
         S  N  Y  N  P  F  H  A  V  V  R  E  N  F  T  E  W  S  N  S

2401    TGGGACGAGTCTCACTACGCCTCCTCGCTCACACCGTTCCTCGAGAAAGAGGGGCTGCCG
         W  D  E  S  H  Y  A  S  S  L  T  P  F  L  E  K  E  G  L  P
```

FIGURE 15 (CONT'D)

SEQ ID NOs: 15 and 16   eg7 encoding EG VI

```
2461    GCACGCTTCATCGTCGACCAGGGTCGCGTTGCCCTCCCGGGAGCCCGCAAGGAGTGgtga
         A  R  F  I  V  D  Q  G  R  V  A  L  P  G  A  R  K  E  W 2521    gtttcgaccagattgaccctcgacccatgcgaccgagattgctgacgattgaattgcgtg 2581    tcccgtcccccagGGGTGAATGGTGCAACGTGGCACCCGCCGGATTTGGCCCCGCGCCCA
                      G  E  W  C  N  V  A  P  A  G  F  G  P  A  P 2641    CGACCAGGGTCAACAACACCGTCGTCGATGCTCTCGTCTGGGTCAAGCCTGGCGGCGAGA
         T  T  R  V  N  N  T  V  V  D  A  L  V  W  V  K  P  G  G  E 2701    GCGACGGCGAGTGTGGCTTGGCTGGCGCCCCAAGGCCGGCCAGTGGTTCGACGAGTACG
         S  D  G  E  C  G  L  A  G  A  P  K  A  G  Q  W  F  D  E  Y 2761    CCCAGATGCTGGTCGAGAATGCCCACCCGTCTGTCGTCCACAAGTGGTAGataatttg
         A  Q  M  L  V  E  N  A  H  P  S  V  V  H  K  W  *

2821    gagtccgagaagggtcccagatagacttttgttttaaaacaaaatgcaaggtgtcgacag
2881    atactggcttaacattaaccaagcaccatgaacatgacttgtcaacatattgatacattc
2941    cgctgctttcccatacgtgctctcaggtctcagggatcaaatggataggtcggtaatgca
3001    aaacgatccattggatatccagaagagagaaaaaaaaaggacatgcatgccttgtctgt
3061    catcatgaggaaacaaaggaaaaacaaacgatcgtcgtgttccaacaagctttccaagac
3121    cacaagacccatccaccaacacaaccaaacgacaagcaatacgatggaccgccgttgttc
3181    catctctcaagagctgactaaacgaacagtcgttgaaatcatcctacatgagtacgccgc
3241    accacctgttatcgtgtaaaccaaatcgcctgttaaagtgcatcatctcttaggtatgat
3301    cgtaagttccggtcacggtcacggatcagggatggttctcaattcgtgtgtcgcgtagcc
3361    gccgccgtatctggacaagacttcttgtattgctccgaaaccgcttttgccgcccctaata
3421    atctgtagccttcttacctggtggtgccttgaaagacgcggcaggcaacacttcgcaggt
3481    ctgtggcgcaccagcaccaggctgtggtgatgccccggaaccggtcgtcgacttgctcgc
3541    ggtgtcctcggctggtgggatgggggtgatgagggcttggagggtgttgttgcgcccgc
3601    aacatccggctccggctccggaccgtccacagacattggacctgcgagcatgactcgtgc
3661    cttcagccagaccaaagccatgccatcatcgcctctgccgacgctgttgagcgggaggct
3721    gatgttctcagccagaactgcgggctgtacggccatgaccatgggctgttcggtctggcc
3781    gtcttgcggcggtttctccctgccagcttgttgtgcgcggtgcctgcgagattcgacttc
```

FIGURE 15 (CONT'D)

SEQ ID NOs: 15 and 16   eg7 encoding EG VI

```
3841        gacctgggcgtggcagagggtgacgagggacgttgacgccttgatctccttgctccccat
3901        gtccttccacccgtacaggcggacgggtgccatacgcgtccacagcctgcacgagaacct
3961        cagggcgtcgtcaatgagttctgtcaacttgctctccagcctctctatgccgcgagcatc
4021        ctgatcctggagcagaaaccgtgccgagcctccgaggaaacgctccttcagcttccgcgc
4081        gtagtttaggcgtgattcaacaaacgtccggcgggactcgttgttgcccgcagcagcgac
4141        gtccttgatgctgaagccgccgtcggcgaacaggcgcatcatctgggccc
```

FIGURE 16

SEQ ID NOs: 17 and 18     xyl2 gene encoding Xyl II

```
1        cgcggccccgtctttgaacgcttgagaagcgcacggtgaagaaccatcaactccgattcc
61       gctcctcatcctcccacgaagccgattgaaatagccacagcggctatgtacggattactc
121      tgctccgtttgcacatccatacacagcgctattttaaaagttcaggacggccaagcccg
181      gttcttggaacggacgacccggattccgaaagctccagcgctcaatgcggtcagtcgtgg
241      cgctgatcctgctgatctgctgatctcataaacccgcaacttcaacttttcactttgaag
301      cgtatacacgcagcgcctctttcaccggcgcattcatactcgcaaattaaccgctaatat
361      cctcgcacttggataatgtgtagccgacacggaggaggggggttgggggggggttggggg
421      gagacatgatggtctgcccaacggatattattattttgttgttttgtataattactgcgg
481      caacattctcaaagggccgtgcctcgcggcgggaaagcccatgacagagaattggacag
541      ctccaagctcgcgatatactctaacaacggcgtgactcggcaatgaaggcctgccgctcg
601      agtgataggggcgaagtaaaacggacgttacatgcggcacttagccggctgatgccggaga
661      atacgggattcaacgatacaatcacacgatgcgacacacctcggcgacttggcgctctat
721      ggaagaaggctgggttaaagctggcgtagattttgcgcgtcttggtttcttaaccgggtt
781      atttctatttctcatatgccgcgagcgaatgcggggtgcagagcgcccgggagtcgatgg
841      tcctatcagacaagagcctggccccggaacctgggataatagaagccaaattaagccatg
901      ggagtatcgtccggggtaggaaccgcacgggcaactagaggaggaagaatttggtataa
961      agggaggacggcggaacaggcttgatggacatgaatcagaagacgacactgggcaactaa
1021     acagcttgcagcagagttttgtgccttgcataggccctcgatatcATGGTCTCGTTCACT
                                                    M  V  S  F  T
1081     CTCCTCCTCACGGTCATCGCCGCTGCGGTGACGACGGCCAGCCCTCTCGAGGTGGTCAAG
361        L  L  L  T  V  I  A  A  A  V  T  T  A  S  P  L  E  V  V  K 1141     CGCGGCATCCAGCCGGGCACGGGCACCCACGAGGGGTACTTCTACTCGTTCTGGACCGAC
381        R  G  I  Q  P  G  T  G  T  H  E  G  Y  F  Y  S  F  W  T  D
1201     GGCCGTGGCTCGGTCGACTTCAACCCCGGGCCCCGCGGCTCGTACAGCGTCACCTGGAAC
401        G  R  G  S  V  D  F  N  P  G  P  R  G  S  Y  S  V  T  W  N
1261     AACGTCAACAACTGGGTTGGCGGCAAGGGCTGGAACCCGGGCCCGCCGCGCAAGATTGCG
421        N  V  N  N  W  V  G  G  K  G  W  N  P  G  P  P  R  K  I  A
1321     TACAACGGCACCTGGAACAACTACAACGTGAACAGCTgtgcgttgtcctcctctttctcc
441        Y  N  G  T  W  N  N  Y  N  V  N  S
1381     Ctttcgcttgttttccttgatgattgggatccatttaaaagagaaggaaaaaaaaaaca
 C1 xyl10 423 for
1441     aaggaaaatagaagataactaacgccaagctctggcagACCTCGCCCTGTACGGCTGGAC
           Y  L  A  L  Y  G  W  T
```

FIGURE 16 (CONT'D)

SEQ ID NOs: 17 and 18    xyl2 gene encoding Xyl II

```
1501  TCGCAACCCGCTGGTCGAGTATTACATCGTGGAGGCATACGGCACGTACAACCCCTCGTC
 501    R   N   P   L   V   E   Y   Y   I   V   E   A   Y   G   T   Y   N   P   S   S
1561  GGGCACGGCGCGGCTGGGCACCATCGAGGACGACGGCGGCGTGTACGACATCTACAAGAC
 521    G   T   A   R   L   G   T   I   E   D   D   G   G   V   Y   D   I   Y   K   T
1621  GACGCGGTACAACCAGCCGTCCATCGAGGGGACCTCCACCTTCGACCAGTACTGGTCCGT
 541    T   R   Y   N   Q   P   S   I   E   G   T   S   T   F   D   Q   Y   W   S   V
1681  CCGCCGCCAGAAGCGCGTCGGCGGCACTATCGACACGGGCAAGCACTTTGACGAGTGGAA
 561    R   R   Q   K   R   V   G   G   T   I   D   T   G   K   H   F   D   E   W   K
                                                                C1 Xyl10 722 rev
1741  GCGCCAGGGCAACCTCCAGCTCGGCACCTGGAACTACATGATCATGGCCACCGAGGGCTA
 581    R   Q   G   N   L   Q   L   G   T   W   N   Y   M   I   M   A   T   E   G   Y
1801  CCAGAGCTCTGGTTCGGCCACTATCGAGGTCCGGGAGGCCTAAgaagccaggcgccttt
 601    Q   S   S   G   S   A   T   I   E   V   R   E   A   *
1861  cttttgttttgcaggagggggtagagggggggggggagggaaaacgaaaagtagcaggt
1921  ggttttatgccggcagccgtgggccattcgagtgcaacctgtatctctctctctcccaag
1981  tctccgggctccttctcagagaacttcaatatgtctggggacaaaccaccttgtgaaata
2041  caacggtaattatctaagtttgagtgccctatcgtatgcttctgaaaatttcctgctcct
2101  tgatacaagtcggtttgagcccgagccaatgagactgtgtcgattgatagaggccctgaag
2161  gatcaagcgcgatgcaacaattaagcatgactacgtgcctagctgcagataaatggaagc
2221  cactcaccaaggtcaacccgcatactggcacgtaagaaccttccgtgtacaaggcccaa
2281  ccgactcacatatctatctgcttgggttttgggatgcggtttttttacccacaaaacaaat
2341  ttgatacaatgctctgctgtgcccgggttgctgagaccaagccgtaatcagcgggcaggg
2401  aatcgagtaggtcacgcctgttgcttggtctagaacaaactaatattaaaaagccttgtg
2461  ctcggcacacatacagaactcgacctgaggcatgttcttggaaggcggctagccagtcaa
2521  gtctggcaccaggccttggtctcgtcgaggataccgagggcgaggaggatgaggaagacc
2581  tctttctcgcctcagatctcttaggggacgaagaagacaacgccggagccacacaataat
2641  taggtctcatatcagacgtttcggcctggccgagctaatatgtctaattatgcccatcag
2701  ccgtatgtcgaggcaggttgcaccgatacgctcgccgcgccgcctcattcatctccgact
2761  gggcacaatgtcgccatctcggccgtcaaggtggtgcaagatacctattatgcaagcaga
2821  ggatcagatggcgggccgatacgagcggctgctccggcttgcgagaaagccgcttcgcag
2881  caaggtatcgtggcaggccgccattttcggttgggtattctttgtcttgtttgcttcgta
2941  attatgtcctggctggcattgtgggaagggcgaacctcttgatttccgatgggggtcga
```

CONSTRUCTION OF HIGHLY EFFICIENT CELLULASE COMPOSITIONS FOR ENZYMATIC HYDROLYSIS OF CELLULOSE

This application is a continuation U.S. patent application Ser. No. 11/487,547, filed on Jul. 13, 2006 (now U.S. Pat. No. 7,883,872) which is a continuation-in-part of U.S. patent application Ser. No. 10/394,568, filed Mar. 21, 2003 (now U.S. Pat. No. 7,399,627), which is a continuation of U.S. patent application Ser. No. 09/548,938 (now U.S. Pat. No. 6,573,086), filed Apr. 13, 2000, which is a continuation-in-part of International Application No. PCT/NL99/00618, filed Oct. 6, 1999, which is a continuation-in-part of International Application No. PCT/EP98/06496, filed Oct. 6, 1998. U.S. patent application Ser. No. 11/487,547, filed on Jul. 13, 2006 (now U.S. Pat. No. 7,883,872) is also a continuation-in-part application of U.S. patent application Ser. No. 09/284,152, filed on Apr. 8, 1999 (now U.S. Pat. No. 7,892,812) which claims priority under 35 U.S.C. §371 national stage filing under International Application No. PCT/US97/17669, filed on Sep. 30, 1997. U.S. patent application Ser. No. 09/284,152, filed on Apr. 8, 1999 (now U.S. Pat. No. 7,892,812) is also a continuation-in-part of Ser. No. 08/731,170 filed Oct. 10, 1996 (now U.S. Pat. No. 5,811,381). All prior applications to which priority is claimed are hereby incorporated by reference in their entirety.

FIELD OF THE INVENTION

This invention relates to compositions and methods for producing bioenergy or other value-added products from lignocellulosic biomass or cellulosic materials. In particular, the invention provides enzyme compositions capable of converting a variety of cellulosic substrates or lignocellulosic biomass into a fermentable sugar. The invention also provides methods for using such enzyme compositions.

INTRODUCTION

Bioconversion of renewable lignocellulosic biomass to a fermentable sugar that is subsequently fermented to produce alcohol (e.g., ethanol) as an alternative to liquid fuels has attracted an intensive attention of researchers since 1970s, when the oil crisis broke out because of decreasing the output of petroleum by OPEC (Bungay H. R., "Energy: the biomass options". NY: Wiley; 1981; Olsson L, Hahn-Hägerdal B. "Fermentation of lignocellulosic hydrolysates for ethanol production", *Enzyme Microb Technol* 1996; 18:312-31; Zaldivar J, Nielsen J, Olsson L. "Fuel ethanol production from lignocellulose: a challenge for metabolic engineering and process integration", *Appl Microbiol Biotechnol* 2001; 56:17-34; Galbe M, Zacchi G., "A review of the production of ethanol from softwood", *Appl Microbiol Biotechnol* 2002; 59:618-28). Ethanol has been widely used as a 10% blend to gasoline in the USA or as a neat fuel for vehicles in Brazil in the last two decades. The importance of fuel bioethanol will increase in parallel with skyrocketing prices for oil and gradual depletion of its sources. Additionally, fermentable sugars are being used to produce plastics, polymers and other biobased products and this industry is expected to grow substantially therefore increasing the demand for abundant low cost fermentable sugars which can be used as a feed stock in lieu of petroleum based feedstocks (e.g. see article "The Rise Of Industrial Biotech" published in Forbes Jul. 24, 2006)

The major polysaccharides comprising different lignocellulosic residues, which may be considered as a potential renewable feedstock, are cellulose and hemicelluloses (xylans). The enzymatic hydrolysis of these polysaccharides to soluble sugars, for example glucose, xylose, arabinose, galactose, mannose, and other hexoses and pentoses occurs under the action of different enzymes acting in concert. Endo-1,4-β-glucanases (EG) and exo-cellobiohydrolases (CBH) catalyze the hydrolysis of insoluble cellulose to cellooligosaccharides (cellobiose as a main product), while β-glucosidases (BGL) convert the oligosaccharides to glucose. Xylanases together with other accessory enzymes (non-limiting examples of which include α-L-arabinofuranosidases, feruloyl and acetylxylan esterases, glucuronidases, and β-xylosidases) catalyze the hydrolysis of hemicelluloses.

Regardless of the type of cellulosic feedstock, the cost and hydrolytic efficiency of enzymes are major factors that restrict the commercialization of the biomass bioconversion processes. The production costs of microbially produced enzymes are tightly connected with a productivity of the enzyme-producing strain and the final activity yield in the fermentation broth. The hydrolytic efficiency of a multienzyme complex in the process of lignocellulose saccharification depends both on properties of individual enzymes, the synergies between them, and their ratio in the multienzyme cocktail.

*Chrysosporium* lucknowense is a fungus that is known to produce a wide variety of cellulases, hemicellulases, and possibly other accessory enzymes. *C. lucknowense* also secrets at least five different endoglucanases, the EG II (51 kDa, Ce15A) being the most active. Moreover, *C. lucknowense* mutant strains (including UV18-25) have been developed to produce enzymes for textile, pulp and paper, detergent and other applications, but not for the enzymatic saccharification of cellulose; these strains can also be used for a high-level production of homologous and heterologous proteins. The best *C. lucknowense* mutant strains secrete at least 50-80 gl$^{-1}$ of extracellular protein in low viscosity fermentations. The full fungal genome of the *C. lucknowense* has been sequenced in 2005 (see http://www.dyadic-group.com/wt/dyad/pr_1115654417), and now the genome annotation is being carried out.

The crude *C. lucknowense* multienzyme complex demonstrates modest results in cellulose saccharification, with only a fraction of the cellulose being converted to glucose under the conditions tested. Two cellobiohydrolases of *C. lucknowense*, belonging to families 7 and 6 of glycoside hydrolases: CBH Ia (Ce17A) and CBH IIa (Ce16A), have been previously isolated and studied. CBH Ia was previously referred to as CBH I, 70(60) kD protein in U.S. Pat. No. 6,573,086. CBH Ia exists in the culture broth as a full size enzyme (observed molecular mass 65 kDa, SDS-PAGE data), consisting of a core catalytic domain and cellulose-binding module (CBM) connected by a flexible peptide linker, and its truncated form (52 kDa), representing the enzyme catalytic domain. CBH I (Ce17A) of *C. lucknowense* appears to be slightly less effective in hydrolysis of crystalline cellulose but more thermostable than the CBH I of *T. reesei*. CBH IIa was previously thought to be an endoglucanase and has been referred to as 43 kD Endo and EG6. See, e.g., U.S. Pat. No. 6,573,086. CBH IIa (43 kDa) has no CBM, i.e. its molecule contains only the catalytic domain.

In spite of the continued research of the last few decades to understand enzymatic lignocellulosic biomass degradation and cellulase production, it remains desirable to discover or to engineer new highly active cellulases and hemicellulases. It would also be highly desirable to construct highly efficient enzyme compositions capable of performing rapid and efficient biodegradation of lignocellulosic materials.

SUMMARY OF THE INVENTION

This invention provides several newly identified and isolated enzymes from *C. lucknowense*. The new enzymes include two new cellobiohydrolases (CBH Ib and IIb, or Ce17B and Ce16B), an endoglucanase (EG VI), (not to be confused with CBH IIa, which was previously referred to as EG 6)a β-glucosidase (BGL), and a xylanase (Xyl II). The CBH IIb has a high activity against Avicel and cotton and displayed a pronounced synergism with other *C. lucknowense* cellulases. Using these new enzymes, this invention provides highly effective enzyme compositions for cellulose hydrolysis.

One object of this invention is to provide an enzyme formulation that includes at least one isolated cellobiohydrolase obtained from *C. lucknowense*. The isolated cellobiohydrolase may be either CBH Ib and IIb. The enzyme formulation may optionally contain an endoglucanase and/or a β-glucosidase. Furthermore, the enzyme formulation may optionally contain a hemicellulase.

Another object of this invention is to provide a method for producing glucose from cellulose. The method includes producing an enzyme formulation that contains at least one isolated cellobiohydrolase obtained from *C. lucknowense*, which can be CBH Ib or IIb. Optionally, the enzyme formulation may contain an endoglucanase and/or a β-glucosidase. The enzyme formulation is applied to cellulose to form glucose.

Yet another aspect of this invention is to provide a method of producing ethanol. The method includes providing an enzyme formulation that contains at least one isolated cellobiohydrolase obtained from *C. lucknowense*, which can be CBH Ib or IIb. The enzyme formulation optionally may contain an endoglucanase and/or a β-glucosidase. Furthermore, the enzyme formulation may optionally contain a hemicellulase. The method further includes applying the enzyme formulation to cellulose to produce glucose and subsequently fermenting the glucose to produce ethanol.

This invention also provides a method of producing energy from ethanol. The method includes providing an enzyme formulation that contains at least one isolated cellobiohydrolase obtained from *C. lucknowense*, which can be CBH Ib or IIb. The enzyme formulation optionally may contain an endoglucanase and/or a β-glucosidase. Furthermore, the enzyme formulation may optionally contain a hemicellulase. The method further includes applying the enzyme formulation to cellulose to produce glucose, fermenting the glucose to produce ethanol, and combusting said ethanol to produce energy.

Another aspect of this invention is to provide a mutant *Chrysosporium lucknowense* strain capable of expressing at least one cellobiohydrolase and at least one endo-1,4-β-glucanase at higher levels than the corresponding non-mutant strain under the same conditions. The cellobiohydrolase is selected from the group consisting of CBH Ia, CBH IIa, CBH Ib, and CBH IIb; and the endo-1,4-β-glucanase is selected from the group consisting of EG II, EG V, and EG VI.

Yet another aspect of this invention is to provide proteins exhibiting at least 65% amino acid identity as determined by the BLAST algorithm with the CBH Ib, CBH IIb, EG VI, BGL, and Xyl II amino acid sequences of SEQ ID NOs. 2, 4, 16, 12, and 18, respectively, or a part thereof having at least 20 contiguous amino acids. This invention also contemplates the corresponding nucleic acid sequences that encode such a protein.

One aspect of this invention provides an enzyme formulation comprising at least one enzyme selected from the group consisting of CBH Ib, CBH IIb, EG II, EG VI, BGL, and Xyl II.

Another aspect of this invention provides a method of producing fermentable sugars from lignocellulosic material. The method comprises (a) providing an enzyme formulation comprising at least one enzyme selected from the group consisting of CBH Ib, CBH IIb, EG II, EG VI, BGL, and Xyl II; and (b) applying the enzyme formulation to lignocellulosic material to produce fermentable sugars.

The invention also provides a method of producing a fermentation product or a starting material for a fermentation product from a fermentable sugar. This method comprises comprises (a) providing an enzyme formulation, wherein the enzyme formulation contains at least one enzyme selected from the group consisting of CBH Ib, CBH IIb, EG II, EG VI, BGL, and Xyl II; (b) applying the enzyme formulation to lignocellulosic material to produce a fermentable sugar; and (c) fermenting said fermentable sugar to produce a fermentation product.

In another aspect, the invention provides a method of producing energy from a fermentable sugar. The method comprises (a) providing an enzyme formulation, wherein the enzyme formulation comprises at least one enzyme selected from the group consisting of CBH Ib, CBH IIb, EG II, EG VI, BGL, and Xyl II; (b) applying the enzyme formulation to lignocellulosic material to produce a fermentable sugar; (c) fermenting the fermentable sugar to produce a combustible fermentation product; and (d) combusting said combustible fermentation product to produce energy.

One object of the invention is provide a mutant *Chrysosporium lucknowense* strain capable of expressing at least one cellobiohydrolase and at least one endo-1,4-β-glucanase at higher levels than the corresponding non-mutant strain under the same conditions. The cellobiohydrolase is selected from the group consisting of CBH Ia, CBH Ib, CBH IIa and CBH IIb; and the endo-1,4-β-glucanase is selected from the group consisting of EG II, EG V, and EG VI.

The invention also provides a protein exhibiting at least 65% amino acid identity as determined by the BLAST algorithm with the CBH Ib, IIb, EG VI, BGL, Xyl II amino acid sequences as defined herein or a part thereof having at least 20 contiguous amino acids.

Another aspect of this invention provides a nucleic acid sequence having at least 80% homology with the nucleic acid sequence encoding CBH Ib, CBH IIb, EG II, EG VI, BGL, or Xyl II, as defined herein.

The invention also provides a method for degrading a lignocellulosic material to fermentable sugars. The method includes contacting the lignocellulosic material with an effective amount of a multi-enzyme product derived from a microorganism, to produce at least one fermentable sugar. At least one enzyme in the multi-enzyme product is selected from the group consisting of CBH Ia, CBH Ib, CBH IIa, CBH IIb, EG II, EG V, EG VI, BGL, and Xyl II.

In another aspect, the invention provides a microorganism or plant capable of expressing one or more of an enzyme selected from the group consisting of CBH Ia, CBH Ib, CBH IIa, CBH IIb, EG II, EG V, EG VI, BGL, and Xyl II.

BRIEF DESCRIPTION OF THE DRAWINGS

FIG. 8: cbh2 gene encoding CBH IB.
FIG. 9: cbh4 gene encoding CBH IIb
FIG. 10: cbh1 gene encoding CBH Ia
FIG. 11: EG6 gene encoding CBH IIa
FIG. 12: eg2 gene encoding EG II
FIG. 13: bgl1 gene encoding BGL
FIG. 14: eg5 gene encoding EGV
FIG. 15: eg7 gene encoding EGVI
FIG. 16: xyl2 gene encoding Xyl II

DETAILED DESCRIPTION OF THE INVENTION

Figure 1:
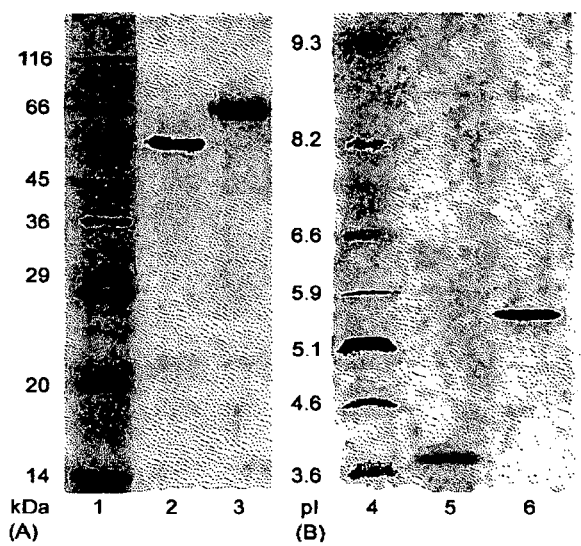
FIG. 1: SDS/PAGE (A) and isoelectrofocusing (B) of purified cellobiohydrolases from *C. lucknowense*. Lanes: 1, markers with different molecular masses; 2 and 5, CBH Ib; 3 and 6, CBH IIb; 4, markers with different pI.

The present invention provides methods and compositions for the conversion of plant biomass to fermentable sugars that can be converted to useful products. The methods include methods for degrading lignocellulosic material using enzyme mixtures to liberate sugars. The compositions of the invention include enzyme combinations that break down lignocellulose. As used herein the terms "biomass" or lignocellulosic material" includes materials containing cellulose and/or hemicellulose. Generally, these materials also contain xylan, lignin, protein, and carbohydrates, such as starch and sugar. Lignocellulose is generally found, for example, in the stems, leaves, hulls, husks, and cobs of plants or leaves, branches, and wood of trees. The process of converting a complex carbohydrate (such as starch, cellulose, or hemicellulose) into fermentable sugars is also referred to herein as "saccharification." Fermentable sugars, as used herein, refers to simple sugars, such as glucose, xylose, arabinose, galactose, mannose, rhamnose, sucrose and fructose.

Biomass can include virgin biomass and/or non-virgin biomass such as agricultural biomass, commercial organics, construction and demolition debris, municipal solid waste, waste paper and yard waste. Common forms of biomass include trees, shrubs and grasses, wheat, wheat straw, sugar cane bagasse, corn, corn husks, corn kernel including fiber from kernels, products and by-products from milling of grains such as corn, wheat and barley (including wet milling and dry milling) as well as municipal solid waste, waste paper and yard waste. The biomass can also be, but is not limited to, herbaceous material, agricultural residues, forestry residues, municipal solid wastes, waste paper, and pulp and paper mill residues. "Agricultural biomass" includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, fruit peels, vines, sugar beet pulp, wheat midlings, oat hulls, and hard and soft woods (not including woods with deleterious materials). In addition, agricultural biomass includes organic waste materials generated from agricultural processes including farming and forestry activities, specifically including forestry wood waste. Agricultural biomass may be any of the aforestated singularly or in any combination or mixture thereof.

The fermentable sugars can be converted to useful value-added fermentation products, non-limiting examples of which include amino acids, vitamins, pharmaceuticals, animal feed supplements, specialty chemicals, chemical feedstocks, plastics, solvents, fuels, or other organic polymers, lactic acid, and ethanol, including fuel ethanol. Specific value-added products that may be produced by the methods of the invention include, but are not limited to, biofuels (including ethanol and butanol); lactic acid; plastics; specialty chemicals; organic acids, including citric acid, succinic acid and maleic acid; solvents; animal feed supplements; pharmaceuticals; vitamins; amino acids, such as lysine, methionine, tryptophan, threonine, and aspartic acid; industrial enzymes, such as proteases, cellulases, amylases, glucanases, lactases, lipases, lyases, oxidoreductases, transferases and xylanases; and chemical feedstocks.

As used herein, a multi-enzyme product can be obtained from or derived from a microbial, plant, or other source or combination thereof, and will contain enzymes capable of degrading lignocellulosic material. Examples of enzymes comprising the multi-enzyme products of the invention include cellulases (such as cellobiohydrolases, endoglucanase, β-glucosidases, hemicellulases (such as xylanases, including endoxylanases, exoxylanase, and β-xylosidase), ligninases, amylases, α-arabinofuranosidases, α-glucuronidases, α-glucuronidases, arabinases, glucuronidases, proteases, esterases (including ferulic acid esterase and acetylxylan esterase), lipases, glucomannanases, and xylogluconases.

In some embodiments, the multi-enzyme product comprises a hemicellulase. Hemicellulose is a complex polymer, and its composition often varies widely from organism to organism, and from one tissue type to another. In general, a main component of hemicellulose is beta-1,4-linked xylose, a five carbon sugar. However, this xylose is often branched as beta-1,3 linkages, and can be substituted with linkages to arabinose, galactose, mannose, glucuronic acid, or by esterification to acetic acid. Hemicellulose can also contain glucan, which is a general term for beta-linked six carbon sugars. Those hemicelluloses include xyloglucan, glucomannan, and galactomannan.

The composition, nature of substitution, and degree of branching of hemicellulose is very different in dicotyledonous plants (dicots, i.e., plant whose seeds have two cotyledons or seed leaves such as lima beans, peanuts, almonds, peas, kidney beans) as compared to monocotyledonous plants (monocots; i.e., plants having a single cotyledon or seed leaf such as corn, wheat, rice, grasses, barley). In dicots, hemicellulose is comprised mainly of xyloglucans that are 1,4-betalinked glucose chains with 1,6-beta-linked xylosyl side chains. In monocots, including most grain crops, the principal components of hemicellulose are heteroxylans. These are primarily comprised of 1,4-beta-linked xylose backbone polymers with 1,3-beta linkages to arabinose, galactose and mannose as well as xylose modified by ester-linked acetic acids. Also present are branched beta glucans comprised of 1,3- and 1,4-beta-linked glucosyl chains. In monocots, cellulose, heteroxylans and beta glucans are present in roughly equal amounts, each comprising about 15-25% of the dry matter of cell walls.

Hemicellulolytic enzymes, i.e. hemicellulases, include includes both exohydrolytic and endohydrolytic enzymes, such as xylanase, β-xylosidase and esterases, which actively cleave hemicellulosic material through hydrolysis. These xylanase and esterase enzymes cleave the xylan and acetyl side chains of xylan and the remaining xylo-oligomers are unsubstituted and can thus be hydrolysed with Pxylosidase only. In addition, several less known side activities have been found in enzyme preparations which hydrolyse hemicellulose. While the multi-enzyme product may contain many types of enzymes, mixtures comprising enzymes that increase or enhance sugar release from biomass are preferred, including hemicellulases. In one embodiment, the hemicullulase is a xylanase, an arabinofuranosidase, an acetyl xylan esterase, a glucuronidase, an endo-galactanase, a mannanase, an endo arabinase, an exo arabinase, an exo-galactanase, a ferulic acid esterase, a galactomannanase, a xylogluconase, or mixtures of any of these. In particular, the enzymes can include glucoamylase, β-xylosidase and/or β-glucosidase. The enzymes of the multi-enzyme product can be provided by a variety of sources. In one embodiment, the enzymes can be produced by growing microorganisms or plants which produce the enzymes naturally or by virtue of being genetically modified to express the enzyme or enzymes. In another embodiment, at least one enzyme of the multi-enzyme product is commercially available.

One embodiment of the present invention relates to an isolated enzyme for catalyzing the conversion of lignocellulosic material to fermentable sugars as described herein, a homologue thereof, and/or a fragment thereof. Also included in the invention are isolated nucleic acid molecules encoding any of such proteins, homologues or fragments thereof. According to the present invention, an isolated protein or polypeptide is a protein that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. An isolated peptide can be produced synthetically (e.g., chemically, such as by peptide synthesis) or recombinantly. An isolated protein can also be provided as a crude fermentation product, or a protein preparation that has been partially purified or purified (e.g., from a microorganism) using protein purification procedures known in the art. In addition, and solely by way of example, a protein referenced as being derived from or from a particular organism, such as a "*Chrysosporium lucknowense* cellulase and/or hemicellulase" refers to a cellulase and/or hemicellulase (generally including a homologue of a naturally occurring cellulose and/or hemicellulase) from a *Chrysosporium lucknowense* microorganism, or to a cellulase and/or hemicellulase that has been otherwise produced from the knowledge of the structure (e.g., sequence), and perhaps the function, of a naturally occurring cellulase and/or hemicellulase from *Chrysosporium lucknowense*. In other words, general reference to a *Chrysosporium lucknowense* cellulase and/or hemicellulase or a cellulase and/or hemicellulase derived from *Chrysosporium lucknowense* includes any cellulase and/or hemicellulase that has substantially similar structure and function of a naturally occurring cellulase and/or hemicellulase from *Chrysosporium lucknowense* or that is a biologically active (i.e., has biological activity) homologue of a naturally occurring cellulase and/or hemicellulase from *Chrysosporium lucknowense* as described in detail herein. As such, a *Chrysosporium lucknowense* cellulase and/or hemicellulase can include purified, partially purified, recombinant, mutated/modified and synthetic proteins. The same description applies to reference to other proteins or peptides described herein and to other microbial sources for such proteins or peptides.

One embodiment of the present invention relates to isolated nucleic acid molecules comprising, consisting essentially of, or consisting of nucleic acid sequences that encode any of the enzymes described herein, including a homologue or fragment of any of such enzymes, as well as nucleic acid sequences that are fully complementary thereto. In accordance with the present invention, an isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Preferably, an isolated nucleic acid molecule of the present invention is produced using recombinant DNA technology (e.g., polymerase chain reaction (PCR) amplification, cloning) or chemical synthesis. A nucleic acid molecule homologue can be produced using a number of methods known to those skilled in the art (see, for example, Sambrook et al., Molecular Cloning: A Laboratory Manual, Cold Spring Harbor Labs Press (1989)). For example, nucleic acid molecules can be modified using a variety of techniques including, but not limited to, classic mutagenesis techniques and recombinant DNA techniques, such as site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, synthesis of oligonucleotide mixtures and ligation of mixture groups to "build" a mixture of nucleic acid molecules and combinations thereof. Nucleic acid molecule homologues can be selected from a mixture of modified nucleic acids by screening for the function of the protein encoded by the nucleic acid and/or by hybridization with a wild-type gene.

Another embodiment of the present invention includes a recombinant nucleic acid molecule comprising a recombinant vector and a nucleic acid sequence encoding protein or peptide having at least one enzymatic activity useful for catalyzing the conversion of lignocellulosic material to fermentable sugars. According to the present invention, a recombinant vector is an engineered (i.e., artificially produced) nucleic acid molecule that is used as a tool for manipulating a nucleic acid sequence of choice and for introducing such a nucleic acid sequence into a host cell. The recombinant vector is therefore suitable for use in cloning, sequencing, and/or otherwise manipulating the nucleic acid sequence of choice, such as by expressing and/or delivering the nucleic acid sequence of choice into a host cell to form a recombinant cell. Such a vector typically contains heterologous nucleic acid sequences, that is nucleic acid sequences that are not naturally found adjacent to nucleic acid sequence to be cloned or delivered, although the vector can also contain regulatory nucleic acid sequences (e.g., promoters, untranslated regions) which are naturally found adjacent to nucleic acid molecules of the present invention or which are useful for expression of the nucleic acid molecules of the present invention (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant organism (e.g., a microbe or a plant). The entire vector can remain in place within a host cell, or under certain conditions, the plasmid DNA can be deleted, leaving behind the nucleic acid molecule of the present invention. The integrated nucleic acid molecule can be under chromosomal promoter control, under native or plasmid promoter control, or under a combination of several promoter controls. Single or multiple copies of the nucleic acid molecule can be integrated into the chromosome. A recombinant vector of the present invention can contain at least one selectable marker.

Typically, a recombinant nucleic acid molecule includes at least one nucleic acid molecule of the present invention operatively linked to one or more expression control sequences. According to the present invention, the phrase "operatively linked" refers to linking a nucleic acid molecule to an expression control sequence (e.g., a transcription control sequence and/or a translation control sequence) in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences.

Suitable transcription control sequences include any transcription control sequence that can function in a host cell or organism into which the recombinant nucleic acid molecule is to be introduced.

Enzymes and Nucleic Acids Encoding the Enzymes

As described in the examples, this invention provides several purified enzymes, including two cellobiohydrolases, (CBH Ib, SEQ ID NO. 2; CBH IIb, SEQ ID NO. 4), an endoglucanase (EG VI, SEQ ID NO. 16), a β-glucosidase (BGL, SEQ ID NO. 12), and a xylanase (Xyl II, SEQ ID NO. 18). This invention also contemplates variants of such enzymes, including variants having amino acid sequence with at least 65%, 70%, or 75% amino acid identity with these enzymes, as determined by the conventionally used BLAST algorithm.

Additionally, the invention provides the nucleic acids that encode these sequences, including gene cbh2 (SEQ ID NO. 1, encoding CBH Ib), gene cbh4 (SEQ ID NO. 3, encoding CBH IIb); gene eg7 (SEQ ID NO. 15, encoding EG VI), gene bgl1 (SEQ ID NO. 11, encoding BGL), and gene xyl2 (SEQ ID NO. 17, encoding Xyl II). This invention also contemplates variants of these nucleic acids, including variants that have at least 80%, 85% or 90% homology with these nucleic acids.

As described herein, the newly identified and isolated enzymes according to the invention can be used in conjunction with at least one other enzyme that promotes saccharification of cellulosic materials. In preferred embodiments, this additional enzyme is derived from *C. lucknowense*. For example, the enzyme may be CBH Ia (SEQ ID NO. 6), CBH IIa (SEQ ID NO. 8), EG II (SEQ ID NO. 10) or EG V (SEQ ID NO. 14). Note however, that in certain preferred embodiments, CBH Ia, CBH IIa EG II, and EG V may be obtained by genetically modifying a microorganism or plant to express cbh1 (SEQ ID NO. 5, encoding CBH Ia), EG6 (SEQ ID NO. 7, encoding CBH IIa), eg2 (SEQ ID NO. 9, encoding EG II), and/or EG5 (SEQ ID NO. 13, encoding EG V). One particularly useful combination for saccharification is CBH Ia, CBH Ib, CBH IIb, EG II, EG V, BGL, and Xyl II.

In certain embodiments, the polynucleotides and polypeptides of the invention are evolved using molecular evolution techniques to create and to identify novel variants with desired structural, functional, and/or physical characteristics. Molecular evolution techniques can be "DNA Shuffling", or "sexual PCR" (WPC, Stemmer, PNAS, 91:10747, (1994)), also referred to as "directed molecular evolution", "exon-shuffling", "directed enzyme evolution", "in vitro evolution" and "artificial evolution". Such reference terms are known in the art and are encompassed by the invention. Characteristics such as activity, the protein's enzyme kinetics, the protein's $K_i$, $K_{cat}$, $K_m$, $V_{max}$, $K_d$, thermostability, pH optimum, and the like can be modified. In certain embodiments, the polynucleotides and/or polypeptides of the invention may be evolved to confer properties that are advantageous for in situ enzymatic saccharification and fermentation. For example, enzymes may be evolved to perform optimally in an environment which is suitable for fermentation of sugars. In one example, the enzymes are evolved to have maximum activity in an environment with elevated temperature and high ambient alcohol content, such as an environment where an organism such as yeast is fermenting sugars. In this way, saccharification of lignocellulose and fermentation occurs in a single process step. In another example, the enzymes are evolved to resist harsh chemical or thermal environments, such as those that may be experienced during lignocellulosic pretreatments, as described herein. In these embodiments, it is not necessary to chemically or thermally pretreat the lignocellulose prior to adding enzymes. Rather, the treatment and enzymatic saccharification can be performed simultaneously. Of course, this invention also contemplates processes involving multiple steps to produce sugars from lignocellulose, such as those where evolved enzymes first saccharify lignocellulose, which is subsequently fermented by an organism, such as yeast, for example.

In other embodiments, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the invention.

Expression of Enzymes

The microorganisms useful in the present invention and/or as a source of enzymes useful in the present invention include any microorganism producing an enzyme capable of degrading lignocellulosic material, including bacteria, yeast, and filamentous fungi. For simplicity and convenience, filamentous fungal microorganisms will be discussed herein; however, one skilled in the art will recognize that other microorganisms will be useful in the present invention. Filamentous fungi have been widely used in industry for the production of proteins. These fungi are uniquely adapted for the production and secretion of proteins owing to their biological niche as microbial scavengers. In environments rich in biological polymers, such as forest floors, the fungi compete by secreting enzymes that degrade those polymers, producing monomers that can be readily utilized as nutrients for growth. The natural ability of fungi to produce proteins has been widely exploited, mainly for the production of industrial enzymes. Levels of protein production in natural isolates can be increased in improved strains by orders-of-magnitude; production yields of tens of grams of protein per liter of fermentation culture are commonplace.

Fungal strains, including, but not limited to, various species of *Talaromyces, Aspergillus, Trichoderma, Neurospora, Penicillium, Fusarium, Humicola, Myceliophthora, Corynascus, Chaetomium, Tolypocladium, Thielavia, Acremonium, Sporotrichum, Thermoascus*, and *Chrysosporium*, are contemplated in the present invention. These are a few of many possible genera of fungi that will be useful sources of enzymes and/or would be suitable as host organisms for producing such enzymes mixtures. Such fungi can be obtained, for instance from various depositories such as the American Type Culture Collection (ATCC), the All Russian Collection of Microorganisms of the Russian Academy of Sciences (VKM), and Centraalbureau voor Schimmelcultures.

Mutant Strains of *C. lucknowense*

Particular strains of *Chrysosporium* express proteins in extremely large amounts and natural expression regulating sequences from these strains are of particular interest. These strains have been designated as *Chrysosporium* strain C1, strain UV13-6, strain NG7C-19 and strain UV18-25. They have been deposited in accordance with the Budapest Treaty with the All Russian Collection (VKM) depository institute in Moscow. The wild type C1 strain was deposited in accordance with the Budapest Treaty with the number VKM F-3500 D, deposit date Aug. 29, 1996, C1 UV13-6 mutant was deposited with number VKM F-3632 D, and deposit date Feb. 9, 1998, C1 NG7c-19 mutant was deposited with number VKM F-3633 D and deposit date Feb. 9, 1998 and C1 UV18-25 mutant was deposited with number VKM F-3631 D and deposit date Feb. 9, 1998.

Preferably an expression-regulating region enabling high expression in the selected host is applied. This can also be a high expression-regulating region derived from a heterologous host, such as are well known in the art. Specific examples of proteins known to be expressed in large quantities and thus providing suitable expression regulating sequences for the invention are without being limited thereto hydrophobin, protease, amylase, xylanase, pectinase, esterase, beta-galactosidase, cellulase (e.g. endo-glucanase, cellobiohydrolase) and polygalacturonase. The high production has been ascertained in both solid state and submerged fermentation conditions. Assays for assessing the presence or production of such proteins are well known in the art.

Heterologous expression-regulating sequences also work efficiently in *Chrysosporium* as native *Chrysosporium* sequences. This allows well known constructs and vectors to be used in transformation of *Chrysosporium* as well as offering numerous other possibilities for constructing vectors enabling good rates of expression in this novel expression and secretion host. As extremely high expression rates for cellulase have been ascertained for *Chrysosporium* strains, the expression regulating regions of such proteins are particularly preferred.

A nucleic acid construct comprising a nucleic acid expression regulatory region from *Chrysosporium lucknowense* or a derivative thereof forms a separate embodiment of the invention as does the mutant *Chrysosporium* strain comprising such regions operably linked to a gene encoding a polypeptide to be expressed. In preferred embodiments, such a nucleic acid construct will be an expression regulatory region from *Chrysosporium* associated with cellobiohydrolase, endoglucanase, β-glucosidase, and/or xylanase expression.

The invention also covers genetically engineered *Chrysosporium* strains wherein the sequence that is introduced can be of *Chrysosporium* origin. Such a strain can, however, be distinguished from natively occurring strains by virtue of for example heterologous sequences being present in the nucleic acid sequence used to transform or transfect the *Chrysosporium*, by virtue of the fact that multiple copies of the sequence encoding the polypeptide of interest are present or by virtue of the fact that these are expressed in an amount exceeding that of the non-engineered strain under identical conditions or by virtue of the fact that expression occurs under normally non-expressing conditions. The latter can be the case if an inducible promoter regulates the sequence of interest contrary to the non-recombinant situation or if another factor induces the expression than is the case in the non-engineered strain. The invention as defined in the preceding embodiments is not intended to cover naturally occurring *Chrysosporium* strains. The invention is directed at strains derived through engineering either using classical genetic technologies or genetic engineering methodologies.

A method of production of a recombinant microorganism or plant is also part of the subject invention. The method comprises stably introducing a nucleic acid sequence encoding a heterologous or homologous polypeptide into a microbial strain or plant, the nucleic acid sequence being operably linked to an expression regulating region. Such procedures are for transforming filamentous fungi have been previous reported. In one preferred embodiment, the mutant *Chrysosporium lucknowense* is derived from UV18-25 (Acc. No. VKM F-3631 D) that has been engineered to overexpress the Xyl II gene.

Genetically Modified Organisms

As used herein, a genetically modified microorganism can include a genetically modified bacterium, yeast, fungus, or other microbe. Such a genetically modified microorganism has a genome which is modified (i.e., mutated or changed) from its normal (i.e., wild-type or naturally occurring) form such that a desired result is achieved (e.g., increased or modified activity and/or production of a least one enzyme or a multi-enzyme product for conversion of lignocellulosic material to fermentable sugars). Genetic modification of a microorganism can be accomplished by using classical strain development and/or molecular genetic techniques. Such techniques known in the art and are generally disclosed for microorganisms, for example, in Sambrook et al., 1989, Molecular Cloning: A Laboratory Manual, Cold Spring Harbor Labs Press. The reference Sambrook et al., ibid., is incorporated by reference herein in its entirety. A genetically modified microorganism can include a microorganism in which nucleic acid molecules have been inserted, deleted or modified (i.e., mutated; e.g., by insertion, deletion, substitution, and/or inversion of nucleotides), in such a manner that such modifications provide the desired effect within the microorganism.

In one aspect of the invention, a genetically modified microorganism can endogenously contain and express an enzyme or a multi-enzyme product for the conversion of lignocellulosic material to fermentable sugars, and the genetic modification can be a genetic modification of one or more of such endogenous enzymes, whereby the modification has some effect on the ability of the microorganism to convert lignocellulosic material to fermentable sugars.

In another aspect of the invention, a genetically modified microorganism can endogenously contain and express an enzyme or a multi-enzyme product for the conversion of lignocellulosic material to fermentable sugars, and the genetic modification can be an introduction of at least one exogenous nucleic acid sequence (e.g., a recombinant nucleic acid molecule), wherein the exogenous nucleic acid sequence encodes at least one additional enzyme useful for the conversion of lignocellulosic material to fermentable sugars and/or a protein that improves the efficiency of the enzyme or multi-enzyme product for the conversion of lignocellulosic material to fermentable sugars. In this aspect of the invention, the microorganism can also have at least one modification to a gene or genes comprising its endogenous enzyme(s) for the conversion of lignocellulosic material to fermentable sugars.

In yet another aspect of the invention, the genetically modified microorganism does not necessarily endogenously (naturally) contain an enzyme or a multi-enzyme product for the conversion of lignocellulosic material to fermentable sugars, but is genetically modified to introduce at least one recombinant nucleic acid molecule encoding at least one enzyme, a multiplicity of enzymes, or a multi-enzyme product for the conversion of lignocellulosic material to fermentable sugars. Such a microorganism can be used in a method of the invention, or as a production microorganism for crude fermentation products, partially purified recombinant enzymes, and/or purified recombinant enzymes, any of which can then be used in a method of the present invention.

Genetically Modified Plants

The invention also contemplates genetically modified plants comprising such genes. The plants may be used for production of the enzymes, or as the lignocellulosic material used as a substrate in the methods of the invention. Methods to generate recombinant plants are known in the art. For instance, numerous methods for plant transformation have been developed, including biological and physical transformation protocols. See, for example, Miki et al., "Procedures for Introducing Foreign DNA into Plants" in Methods in Plant Molecular Biology and Biotechnology, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in Methods in Plant Molecular Biology and Biotechnology, Glick, B. R. and Thompson, J. E. Eds. (CRC Press, Inc., Boca Raton, 1993) pp. 89-119.

In certain embodiments of the invention, genetically modified plants that express the enzymes of this invention are obtained by introducing an expression vector into plants based on the natural transformation system of *Agrobacterium*. See, for example, Horsch et al., Science, 227:1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant. Sci. 10:1 (1991). Descriptions of *Agrobacterium* vector systems and methods for *Agrobacterium*-mediated gene transfer are provided by numerous references, including Gruber et al., supra, Miki et al., supra, Moloney et al., Plant Cell Reports 8:238 (1989), and U.S. Pat. Nos. 4,940,838 and 5,464,763, hereby incorporated by reference in their entirety.

In other embodiments, genetically modified plants are obtained by microprojectile-mediated transformation wherein DNA is carried on the surface of microprojectiles. The expression vector is introduced into plant tissues with a biolistic device that accelerates the microprojectiles to speeds sufficient to penetrate plant cell walls and membranes. Sanford et al., Part. Sci. Technol. 5:27 (1987), Sanford, J. C., Trends Biotech. 6:299 (1988), Sanford, J. C., Physiol. Plant 79:206 (1990), Klein et al., Biotechnology 10:268 (1992).

Another method for physical delivery of DNA to plants contemplated by this invention is sonication of target cells. Zhang et al., Bio Technology 9:996 (1991). Alternatively, liposome or spheroplast fusion have been used to introduce expression vectors into plants. Deshayes et al., EMBO J., 4:2731 (1985), Christou et al., Proc Natl. Acad. Sci. USA 84:3962 (1987). Direct uptake of DNA into protoplasts using CaCh precipitation, polyvinyl alcohol or poly-L-ornithine have also been reported. Hain et al., Mol. Gen. Genet. 199:161 (1985) and Draper et al., Plant Cell Physiol. 23:451 (1982). Electroporation of protoplasts and whole cells and tissues have also been described. Donn et al., In Abstracts of VIIth International Congress on Plant Cell and Tissue Culture IAPTC, A2-38, p. 53 (1990); D'Halluin et al., Plant Cell 4:1495-1505 (1992) and Spencer et al., Plant Mol. Biol. 24:51-61 (1994).

Methods of Using the Enzymes and Mutant Strains of *C. lucknowense*

This invention also provides methods of enzymatic saccharification of cellulosic materials. Any cellulose containing material can be treated by the enzymes of this invention, non-limiting examples of which include orchard prunings, chaparral, mill waste, urban wood waste, yard waste, municipal waste, logging waste, forest thinnings, short-rotation woody crops, industrial waste, wheat straw, oat straw, rice straw, barley straw, rye straw, flax straw, sugar cane, corn stover, corn stalks, corn cobs, corn husks, prairie grass, gamagrass, foxtail; sugar beet pulp, citrus fruit pulp, seed hulls, cellulosic animal wastes, lawn clippings, cotton, and seaweed.

In certain preferred embodiments, the lignocellulosic materials are pretreated before being exposed to the enzymes or enzyme mixtures of the invention. Generally speaking, the pretreatment can be any procedure that makes the subsequent enzymatic saccharification of the lignocellulosic materials more efficient (i.e., either less time-consuming or less costly). For example, the lignocellulosic material may be pretreated by methods including, but not limited to, exposure to acids, bases, solvents, heat, peroxides, ozone, or some combination thereof prior to enzymatic saccharafication. These pretreatments can also be combined with other forms of processing, such as mechanical shredding, grinding, milling, or rapid depressurization (e.g. steam explosion).

Generally, enzymatic saccharification according to the invention involves using CBH Ia, CBH IIb, EG VI, BGL, Xyl II, or mixtures thereof. One or more of these enzymes may be further combined with other enzymes capable of promoting enzymatic saccharification, which may be derived from *C. lucknowense*, a mutant strain, or another organism. For example, in one embodiment, the enzymatic saccharification involves an enzyme mixture comprising CBH Ia, CBH Ib, CBH IIb, EG II, EG V, BGL, and Xyl II. In other preferred embodiments, the enzymatic mixture contains a cellobiohydrolase, which may be CBH Ia, CBH Ib, CBH IIa, CBH IIb, and mixtures thereof, with a β-glucosidase such as BGL.

In certain embodiments, the enzyme compositions are artificial enzyme compositions that contain purified forms of CBH Ia, CBH Ib, CBH IIb, EG II, EG VI, BGL, or Xyl II. The purified forms of these enzymes may be used alone on mixed together. In certain preferred embodiments, the selected purified enzymes are present in higher relative amounts than would be the case for the enzyme secretions of the wild type *C. lucknowense*.

In certain embodiments, the invention provides a mutant strain of *C. lucknowense* that is capable of expressing CBH Ia, CBH Ib, CBH IIa, CBH IIb, EG II, EG V, EG VI, BGL, or Xyl II, or mixtures thereof in proportions higher than found in the enzyme secretions of the wild-type organism. The secreted enzymes of such a mutant strain of *C. lucknowense* may serve as a raw source from which purified forms of CBH Ia, CBH Ib, CBH IIa, CBH IIb, EG II, EG V, EG VI, BGL, or Xyl II, can be produced. Alternatively, the secreted enzymes of such a mutant strain may also be applied directly to the cellulosic materials to be saccharified. In particularly preferred embodiments, the cellulosic materials are exposed directly to the mutant strain of *C. lucknowense* in an environment conducive to the proliferation of the mutant strain of *C. lucknowense*, such as in a bioreactor. The in situ secretions of CBIa, CBH Ib, CBH IIa, CBH IIb, EG II, EG V, EG VI, BGL, or Xyl II, or mixtures thereof by the mutant strain of *C. lucknowense*, in proportions higher than found in the enzyme secretions of the wild-type organism, lead to enhanced in situ saccharification of the cellulosic material.

Following enzymatic treatment by the inventive enzymatic compositions of the invention, the fermentable sugar that is produced can be exposed to microorganisms, either naturally occurring or genetically engineered, that are capable of fermenting the sugar to produce ethanol or some other value-added fermentation product. Preferably, substantially all of the glucose is converted to ethanol, which may be subsequently used as a fuel, solvent, or chemical reactant. In preferred embodiments, the ethanol is used as a fuel for powering transportation vehicles, non-limiting examples of which include cars, trucks, buses, mopeds and motorcycles. Other potential fermentation products from glucose include, but are not limited to, biofuels (including ethanol); lactic acid; plastics; specialty chemicals; organic acids, including citric acid, succinic acid and maleic acid; solvents; animal feed supplements; pharmaceuticals; vitamins; amino acids, such as lysine, methionine, tryptophan, threonine, and aspartic acid; industrial enzymes, such as proteases, cellulases, amylases, glucanases, lactases, lipases, lyases, oxidoreductases, and transferases; and chemical feedstocks.

EXAMPLES

Example 1

Enzyme Isolation

Culture filtrates produced by the *C. lucknowense* mutant strains were used for isolation of individual enzymes. Commercial preparation of NCE-L600 (*C. lucknowense*) were from Dyadic International, Inc., USA.

Highly purified BGL (cellobiase) from *Aspergillus japonicus* was obtained from a commercial preparation, having specific cellobiase activity 50 U $mg^{-1}$ protein (pH 5.0, 40° C.), and was used in the experiments on hydrolysis of insoluble cellulose.

Example 2

Enzyme Purification

The enzyme purification was carried out by chromatography on a Pharmacia FPLC system (Sweden). Cellobiohydrolases and endoglucanases BGL and Xyl II were isolated from a *C. lucknowense* UV18-25 culture filtrate. BGL and Xyl II (xylanase II) were isolated from culture filtrates produced by the *C. lucknowense* UV18ΔCbh1#10 and Xyl2-18 mutant strains, respectively.

In all cases, the first purification stage was anion-exchange chromatography on a Source 15Q column (40 ml volume). The column was equilibrated with 0.02 M Bis-Tris-HCl buffer, pH 6.8. The initial culture filtrate was preliminarily desalted and transferred into the starting buffer by gel-filtration on Acrylex P4 (Reanal, Hungary). The sample (400 mg of protein) was applied to the Source 15Q column, and the elution was carried out with a gradient of 0-1 M NaCl at a flow rate of 10 ml $min^{-1}$.

The first protein fraction after the Source 15Q, eluted at 0.05 M NaCl and having high Avicelase activity, was subjected to hydrophobic interaction chromatography on a Source 15 Isopropyl column (Pharmacia, Sweden). The column was equilibrated with 1.7 M ammonium sulfate in 50 mM Na-acetate buffer, pH 5.0. Proteins were eluted with a reverse linear gradient of 1.7-0 M ammonium sulfate at a flow rate of 4 ml $min^{-1}$. The protein fraction with the highest activity against Avicel (eluting at a salt concentration of 0.30-0.35 M) contained the homogeneous protein with a molecular mass of 70 kDa (CBH IIb, see FIG. 1).

The protein fraction after the Source 15Q, eluted at 0.22 M NaCl and having the activity against Avicel and p-NP-β-D-cellobioside, was further purified by chromatofocusing on a Mono P HR 5/20 column (Pharmacia, Sweden). The column was equilibrated with 0.025 M Na-formate buffer, pH 4.0. Proteins were eluted with a gradient of pH 4.5-3.0 (using Polybuffer 74) at a flow rate of 0.5 $ml^{-1}$. Homogeneous 60 kDa CBH Ib was obtained as a result of chromatofocusing (FIG. 1).

The two newly isolated cellobiohydrolases are homogeneous according to the data of SDS-PAGE and isoelectrofocusing (FIG. 1), their molecular masses were found to be 60 and 70 kDa, pI 3.8 and 5.6, respectively. Peptide mass finger-printing using MALDI-TOF mass spectrometry (data not shown) indicated that these proteins were different from the above-mentioned cellobiohydrolases (Ce16A and Ce17A) as well as from other *C. lucknowense* enzymes previously isolated. Subsequent de novo sequencing of tryptic peptides from the new cellobiohydrolases, using tandem TOF/TOF mass spectrometry (MS/MS), followed by the BLAST search in the SWISS-PROT (UniProtKB) database showed that the 60 kDa and 70 kDa proteins display sequence similarity to cellobiohydrolases from the GH families 7 and 6 (Table 1, see classification into families in http://afmb.cnrs-mrs.fr/CAZY/). So, they were classified as Ce17B (CBH Ib) and Ce16B (CBH IIb), respectively. Thus, the *C. lucknowense* fungus secretes at least four cellobiohydrolases encoded by different genes, two of them belonging to the glycosyl hydrolase family 6 (GH6) and two other enzymes—to the GH7 family (Table 2). The molecules of the CBH Ia (Ce17A) and CBH IIb (Ce16B) represent typical cellulases consisting of a catalytic domain and CBM connected by a flexible peptide linker. The molecules of CBH Ib (Ce17B) and CBH IIa (Ce16A) consist of only the catalytic domains (they lack CBM). It should be noted that the most studied fungus *T. reesei* has only two cellobiohydrolases: I (Ce17A) and II (Ce16A). Other fungi, such as *Humicola insolens*, also secrete two cellobiohydrolases (Ce17A and Ce16A), while *Phanerochaete chrysosporium* produces at least seven different cellobiohydrolases, of which six enzymes belong to the GH7 family. All the enzymes mentioned, except for the *P. chrysosporium* CBH 1-1 (Ce17A), possess CBM.

The BGL was isolated from the protein fraction after the Source 15Q (eluted at 0.10 M NaCl) containing the highest activity against p-NP-β-D-glucopyranoside and cellobiose. The fraction was subjected to hydrophobic interaction chromatography as described above, the homogeneous BGL with a molecular mass of 106 kDa and pI 4.8 was eluted at 1.3 M of ammonium sulfate. The specific activity of the BGL toward p-NP-β-D-glucopyranoside and cellobiose was found to be 11 and 26 U mg$^{-1}$ of protein, respectively (40° C., pH 5.0). Purified BGL had optimum activity at pH 4.0 and retained >50% of activity in the range of pH 2.5-6.5. The temperature optimum was 40° C. After heating for three hours, the enzyme retained 10% activity at 60° C., 64% at 50° C., and 100% at 40° C. The enzyme was highly active against cellobiose, gentiobiose, and laminarobiose as substrates. Weak activity was also observed using sophorose, cellotriose, cellotetraose, cellopentaose, and cellohexaose as substrates. No activity was observed with lactose or tregalose as substrates.

The homogeneous Xyl II (24 kDa, pI 7.9) was obtained after anion-exchange chromatography followed by hydrophobic interaction chromatography as described above and gel-filtration on a Superose 12 HR 10/30 column (Pharmacia, Sweden). Elution at the last chromatographic stage was performed with 0.1 M Na-acetate buffer, pH 5.0, at a flow rate of 0.3 ml min$^{-1}$. The Xyl II had specific xylanase activity of 395 U mg$^{-1}$ of protein (50° C., pH 5.0, birchwood xylan as a substrate). The enzyme had a pH optimum of 6.0 and a temperature optimum of 70° C. Xyl II was highly specific for xylan as substrate, with no activity against carboxymethylcellulose (CMC) or barley β-glucan.

The *C. lucknowense* CBH Ia (65 kDa), CBH IIa (43 kDa), EG II (51 kDa), EG V (25 kDa), EG VI (47 kDa) were purified as described elsewhere (see, Gusakov A V, Sinitsyn A P, Salanovich T N, Bukhtojarov F E, Markov A V, Ustinov B B, van Zeijl C, Punt P, Burlingame R. "Purification, cloning and characterisation of two forms of thermostable and highly active cellobiohydrolase I (Ce17A) produced by the industrial strain of *Chrysosporium lucknowense*" *Enzyme Microb Technol* 2005; 36:57-69; Bukhtojarov F E, Ustinov B B, Salanovich T N, Antonov A I, Gusakov A V, Okunev O N, Sinitsyn A P. "Cellulase complex of the fungus *Chrysosporium lucknowense*: isolation and characterization of endoglucanases and cellobiohydrolases", *Biochemistry* (Moscow) 2004; 69:542-51.

The enzyme purity was characterized by SDS-PAGE and isoelectrofocusing. SDS-PAGE was carried out in 12% gel using a Mini Protean II equipment (Bio-Rad Laboratories, USA). Isoelectrofocusing was performed on a Model 111 Mini IEF Cell (Bio-Rad Laboratories, USA). Staining of protein was carried out with Coomassie Blue.

Example 3

MALDI-TOF and Tandem TOF/TOF Mass Spectrometry of Peptides

The in-gel tryptic digestion of the protein bands after the SDS-PAGE was carried out essentially as described by Smith (Smith B E. Protein sequencing protocols. Totowa: Humana Press; 1997). Trypsin (Promega, modified, 5 µg/mL) in 50 mM NH$_4$HCO$_3$ was used for a protein digestion. The resulting peptides were extracted from a gel with 20% aqueous acetonitrile containing 0.1% trifluoroacetic acid and subjected to MALDI-TOF MS (see, James P. (Ed.) Proteome research: mass spectrometry. Berlin: Springer-Verlag; 2001.) Selected peptides from the mass spectra of the tryptic digests of the CBH Ib and IIb were analyzed by tandem mass spectrometry in order to determine their sequences de novo. Ultraflex TOF/TOF mass spectrometer (Bruker Daltonik Gmbh, Germany) was used in the MS experiments.

Example 4

Enzyme Activity Assays

CMCase activity was measured by assaying reducing sugars released after 5 min of enzyme reaction with 0.5% carboxymethylcellulose (CMC, medium viscosity, Sigma, USA) at pH 5.0 and 50° C. (Sinitsyn A P, Chemoglazov V M, Gusakov A V. "Methods of investigation and properties of cellulolytic enzymes" (in Russian), Biotechnology Series, v. 25. Moscow: VINITI Press; 1990). Enzyme activities against barley β-glucan (Megazyme, Australia) and birchwood xylan (Sigma, USA) were determined in the same way as the CMCase activity, except the incubation time was 10 min. Avicelase activity was determined by analysing reducing sugars released after 60 min of enzyme reaction with 5 mg ml$^{-1}$ Avicel PH 105 (Serva, Germany) at pH 5.0 and 40° C. Reducing sugars were analysed by the Somogyi-Nelson method (Sinitsyn A P, Chernoglazov V M, Gusakov A V, "Methods of investigation and properties of cellulolytic enzymes" (in Russian), *Biotechnology Series*, v. 25. Moscow: VINITI Press; 1990; Somogyi M., "Notes on sugar determination" *J Biol Chem* 1952; 195:19-23. Filter paper activity (FPA) was determined as recommended by Ghose (Ghose T K. "Measurement of cellulase activities", *Pure Appl Chem* 1987; 59:257-68).

Activities against p-NP-β-D-glucopyranoside, p-NP-β-D-cellobioside and p-NP-β-D-lactoside (Sigma, USA) were determined at pH 5.0 and 40° C. as described elsewhere (Gusakov A V, Sinitsyn A P, Salanovich T N, Bukhtojarov F E, Markov A V, Ustinov B B, van Zeijl C, Punt P, Burlingame R. "Purification, cloning and characterisation of two forms of thermostable and highly active cellobiohydrolase I (Ce17A) produced by the industrial strain of *Chrysosporium lucknowense*", *Enzyme Microb Technol* 2005; 36:57-69).

Cellobiase activity was assayed at pH 5.0 and 40° C. by measuring the initial rate of glucose release from 2 mM cellobiose by the glucose oxidase-peroxidase method (Sinitsyn A P, Chernoglazov V M, Gusakov A V, "Methods of investigation and properties of cellulolytic enzymes" (in Russian), *Biotechnology Series*, v. 25. Moscow: VINITI Press; 1990).

All activities were expressed in International Units, i.e. one unit of activity corresponded to the quantity of enzyme hydrolysing one µmol of substrate or releasing one µmol of reducing sugars (in glucose equivalents) per one minute.

Example 5

Enzymatic Hydrolysis of Cellulosic Substrates

The enzymatic hydrolysis of cellulosic substrates was carried out at pH 5.0 under magnetic stirring. Avicel PH 105 (Serva, Germany), cotton pretreated with acetone-ethanol mixture (1:1) for two days in order to remove wax from the surface of cellulose fibres, and Douglas fir wood pretreated by organosolv were used as substrates.

The experiments on progress kinetics of Avicel hydrolysis by purified individual cellobiohydrolases and experiments on synergistic interaction between *C. lucknowense* cellulases (with cotton as a substrate) were carried out at 40° C. The substrate concentration in those experiments was 5 mg ml$^{-1}$. In order to eliminate the effect of product (cellobiose) inhibition on the kinetics and to convert all cellooligosaccharides to glucose, the hydrolysis was carried out in the presence of purified BGL (cellobiase) from *A. japonicus*, which was extra added to the reaction system in excessive quantity (0.5 U ml$^{-1}$).

The experiments on enzymatic saccharification of Avicel, cotton, and pretreated Douglas fir wood by combinations of purified *C. lucknowense* enzymes and crude multienzyme preparations were carried out at 50° C. The concentration of Avicel and pretreated wood in those experiments was 50 mg ml$^{-1}$, while the concentration of cotton was 25 mg ml$^{-1}$.

A typical experiment was carried out in the following way. A weighed amount of dry cellulosic substrate was placed into a 2-ml plastic test tube, then 0.5-1 ml of 0.05 M Na-acetate buffer, containing 1 mM NaN$_3$ to prevent microbial contamination, was added, and the substrate was soaked in the buffer for 1 h. Then, the tube was placed into a thermostated water bath, located on a magnetic stirrer, and suitably diluted enzyme solution in the same buffer was added to the substrate suspension in order to adjust the total volume of the reaction system to 2 ml and to start the hydrolysis. The tube was hermetically closed with a lid, and the hydrolysis was carried out with magnetic stirring. At defined times in the reaction, an aliquot of the suspension (0.05-0.1 ml) was taken, diluted, centrifuged for 3 min at 15000 rpm, and the concentrations of glucose and reducing sugars in the supernatant were determined by the glucose oxidase-peroxidase and Somogyi-Nelson methods. In those cases, when glucose was a single product of the reaction, the degree of substrate conversion (for Avicel and cotton, which represented pure cellulosic substrates) was calculated using the following equation:

$$\text{Conversion (\%)} = \frac{\text{Glucose concentration (mg ml}^{-1}) \times 100\%}{\text{Initial substrate concentration (mg ml}^{-1}) \times 1.11}$$

The kinetic experiments were carried out in duplicates. Protein concentration was the measure of enzyme loading in the reaction system. In the case of purified enzymes, the protein concentration was calculated from the UV absorption at 280 nm using enzyme extinction coefficients predicted by the ProtParam tool (http://www.expasy.ch/tools/protparam-.html). For crude multienzyme preparations, the protein concentration was determined by the Lowry method using bovine serum albumin as a standard.

The CBH Ib and IIb displayed maximum activity at pH 4.7 and 5.0. Both enzymes were stable during 24 h incubation at pH 5.0 and 50° C. Study of the enzyme adsorption on Avicel, carried out at pH 5.0 and 6° C., revealed that only the CBH IIb has CBM. After incubation of the CBH Ib and IIb (1 mg ml$^{-1}$) with Avicel (25 mg ml$^{-1}$) for 30 min on stirring the degree of protein adsorption was 65 and 99%, respectively. It should be noted that the adsorption degree of the catalytic domain of the *C. lucknowense* CBH Ia was 59% under the same conditions, while that for the full size *C. lucknowense* CBH Ia (an enzyme with CBM) was 89%.

The CBH IIb had a high activity against Avicel and very low CMCase activity, while the activity toward synthetic p-nitrophenyl derivatives of disaccharides was completely absent (Table 2). The CBH Ib displayed lower Avicelase activity, but hydrolysed p-NP-β-D-cellobioside and p-NP-β-D-lactoside, which is typical for family 7 cellulases. For a comparison, specific activities of previously isolated *C. lucknowense* cellobiohydrolases (now named as CBH Ia and CBH IIa) are also given in Table 2.

Figure 2:
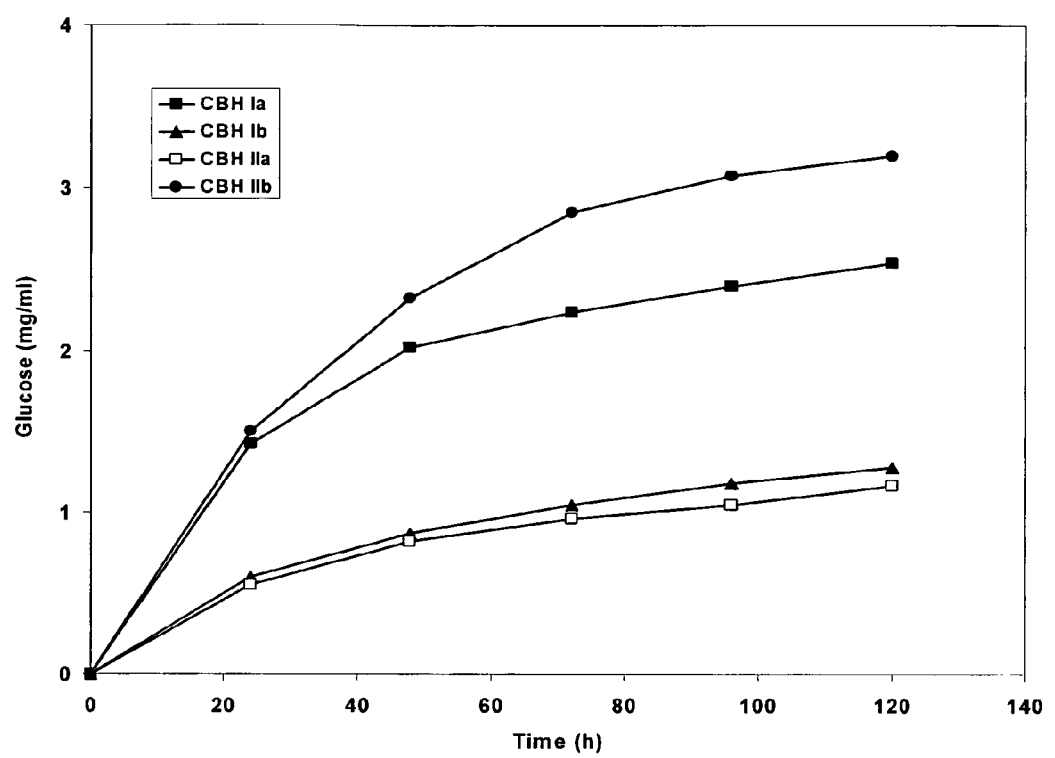
FIG. 2: Progress kinetics of Avicel (5 mg ml$^{-1}$) hydrolysis by purified cellobiohydrolases (0.1 mg ml$^{-1}$) in the presence of purified *A. japonicus* BGL (0.5 U ml$^{-1}$), 40° C., pH 5.0.

FIG. 2 shows the progress kinetics of Avicel hydrolysis by the all purified *C. lucknowense* cellobiohydrolases, where the enzymes were equalized by protein concentration (0.1 mg ml$^{-1}$). In order to eliminate the effect of product (cellobiose) inhibition on the kinetics, the hydrolysis was carried out in the presence of purified BGL (cellobiase) from *A. japonicus*, added to the reaction system in excessive quantity (0.5 U ml$^{-1}$).

The highest hydrolysis rate amongst a few cellobiohydrolases tested, including three other *C. lucknowense* enzymes (CBH Ia, Ib, IIa) was observed in the case of *C. lucknowense* CBH IIb: 3.2 mg ml$^{-1}$ of glucose, i.e. 58% cellulose conversion was achieved after 5 days of hydrolysis (see FIG. 2). The *C. lucknowense* CBH Ia (which has a CBM) was notably less effective (the yield of glucose after 5 days was 2.5 mg ml$^{-1}$, which corresponded to the cellulose conversion degree of 46%, respectively). As expected, the *C. lucknowense* cellobiohydrolases without CBM (CBH Ib and IIa) had the lowest ability to hydrolyse Avicel: only 23 and 21% cellulose conversion was achieved after the same time of reaction.

Both *C. lucknowense* cellobiohydrolases having a CBM (Ia and IIb) displayed a pronounced synergism with three major endoglucanases from the same fungus (EG II, EG V, EG VI) in hydrolysis of cotton as well as a strong synergy with each other (Table 3). In these studies, the concentration of cotton was 5 mg ml$^{-1}$, the CBH concentration was 0.15 mg ml$^{-1}$ in all cases, while the EG concentration was always 0.05 mg ml$^{-1}$. In order to eliminate the effect of product inhibition on the kinetics and to convert the intermediate oligosaccharides to glucose, the hydrolysis was carried out in the presence of purified BGL from *A. japonicus*, added to the reaction system in excessive quantity (0.5 U ml$^{-1}$). The experiments were carried out at pH 5.0 and 40° C. for 140 h.

As seen from Table 3, individual cellobiohydrolases, CBH Ia and CBH IIb, and the individual endoglucanases, did not completely hydrolyze cotton under the conditions tested. The CBH IIb provided the highest glucose yield after 140 h of hydrolysis: 1.18 mg ml$^{-1}$, which corresponded to the substrate conversion degree of 21%. However, when either cellobiohydrolase was incubated with endogluacanase, a pronounced synergism was observed. The highest glucose yields (4.1-4.7 mg ml$^{-1}$) were achieved with combinations of CBH Ia or CBH IIb with EG II, the coefficient of synergism being varied in the range of 2.6-2.8. A strong synergism ($K_{syn}$=2.75) was also observed between CBH Ia and CBH IIb. In fact, the combination of two cellobiohydrolases (1:1 by weight) with BGL provided practically complete conversion (98.6%) of cotton cellulose to glucose after 140 h of hydrolysis.

Figure 3:
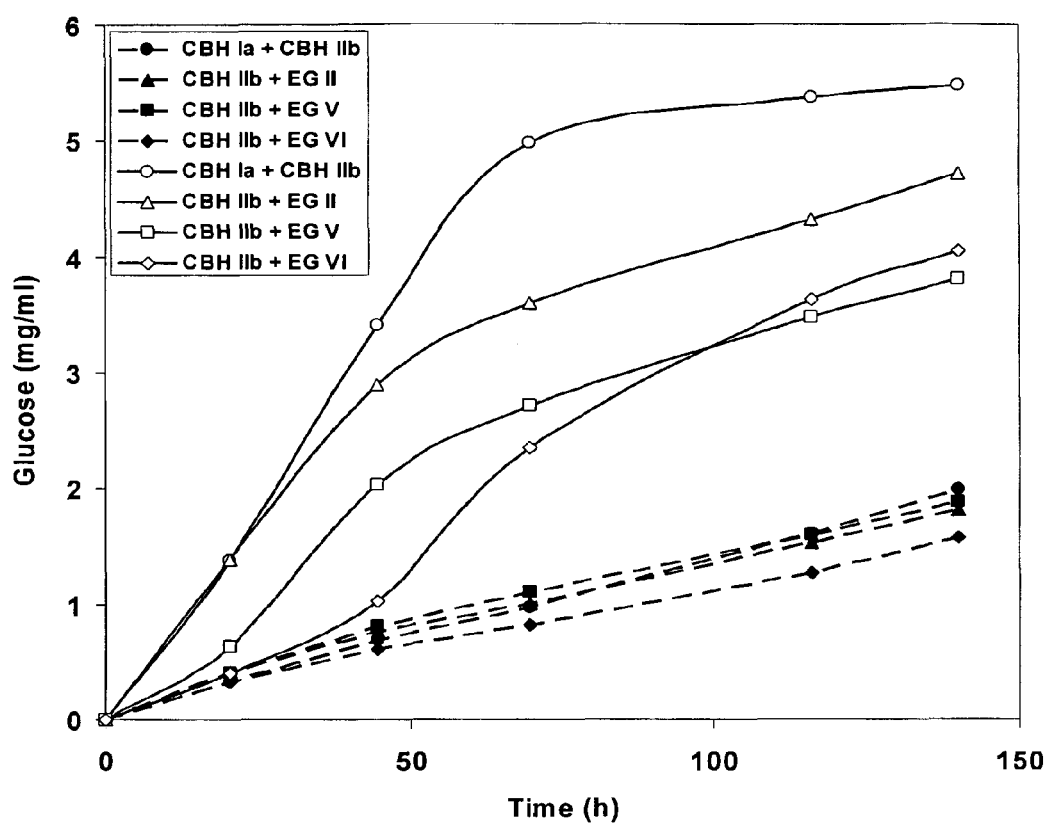
FIG. 3: Synergism between CBH IIb and other *C. lucknowense* purified enzymes during hydrolysis of cotton cellulose (5 mg ml$^{-1}$) in the presence of purified *A. japonicus* BGL (0.5 U ml$^{-1}$), 40° C., pH 5.0. The CBH and EG concentration was 0.15 and 0.05 mg ml$^{-1}$, respectively. Experimental data for the pairs of enzymes are shown with open symbols (continuous curves); the theoretical sums of glucose concentrations obtained under the action of individual enzymes are shown with filled symbols (dotted lines).

As an example, the progress kinetics of cotton hydrolysis by combinations of CBH IIb with other *C. lucknowense* enzymes are shown in FIG. 3, where real experimental data are shown with open symbols (continuous curves) while the theoretical sums of glucose concentrations obtained under the action of individual enzymes are shown with filled symbols (dotted lines). Glucose yields obtained after 140 h of cotton hydrolysis under the action of individual cellobiohydrolases and endoglucanases and their combinations are summarized in Table 3. The coefficient of synergism ($K_{syn}$) was calculated as a ratio of experimental glucose concentration (column 2 of Table 3) to the theoretical sum of glucose concentrations (column 3).

Figure 4:
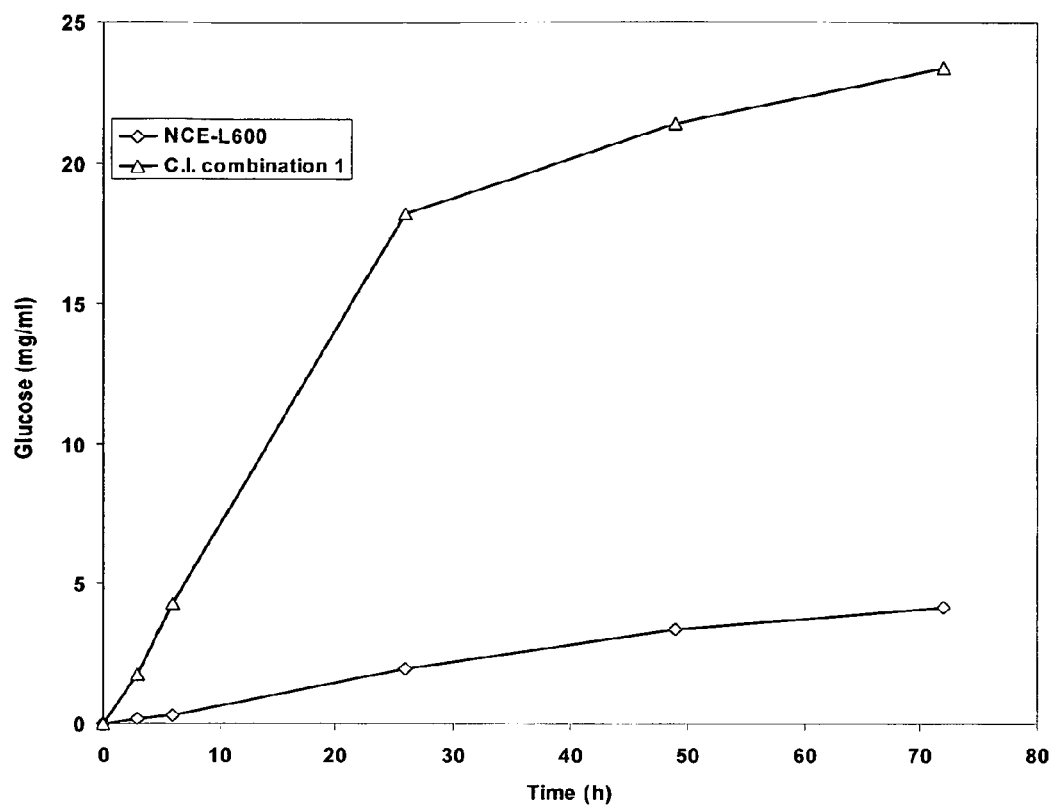
FIG. 4: Progress kinetics of cotton (25 mg ml$^{-1}$) hydrolysis by combination #1 of purified *C. lucknowense* enzymes and NCE L-600, a commercial *C. lucknowense* multienzyme cellulase preparation at protein loading of 0.5 mg ml$^{-1}$, 50° C., pH 5.0 (see text and Table 4 for details).
Figure 5:
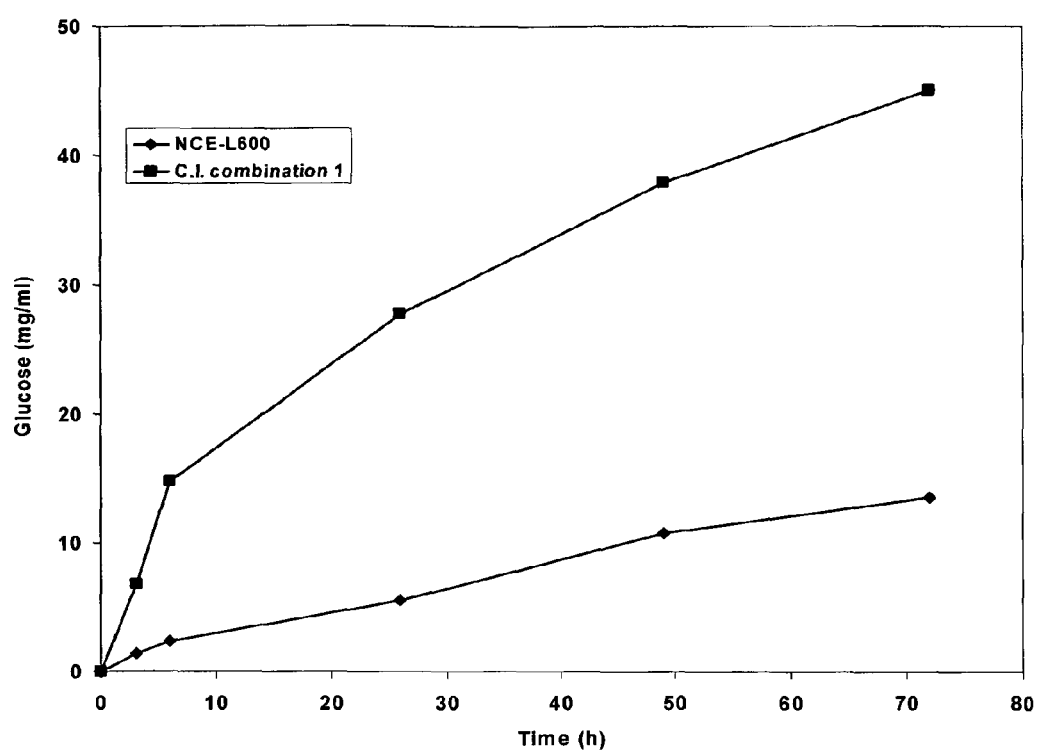
FIG. 5: Progress kinetics of Avicel (50 mg ml$^{-1}$) hydrolysis by combination #1 of purified *C. lucknowense* enzymes and NCE-L, a commercial *C. lucknowense* multienzyme cellulase preparation at protein loading of 0.5 mg ml$^{-1}$, 50° C., pH 5.0 (see text and Table 4 for details).
Figure 6:
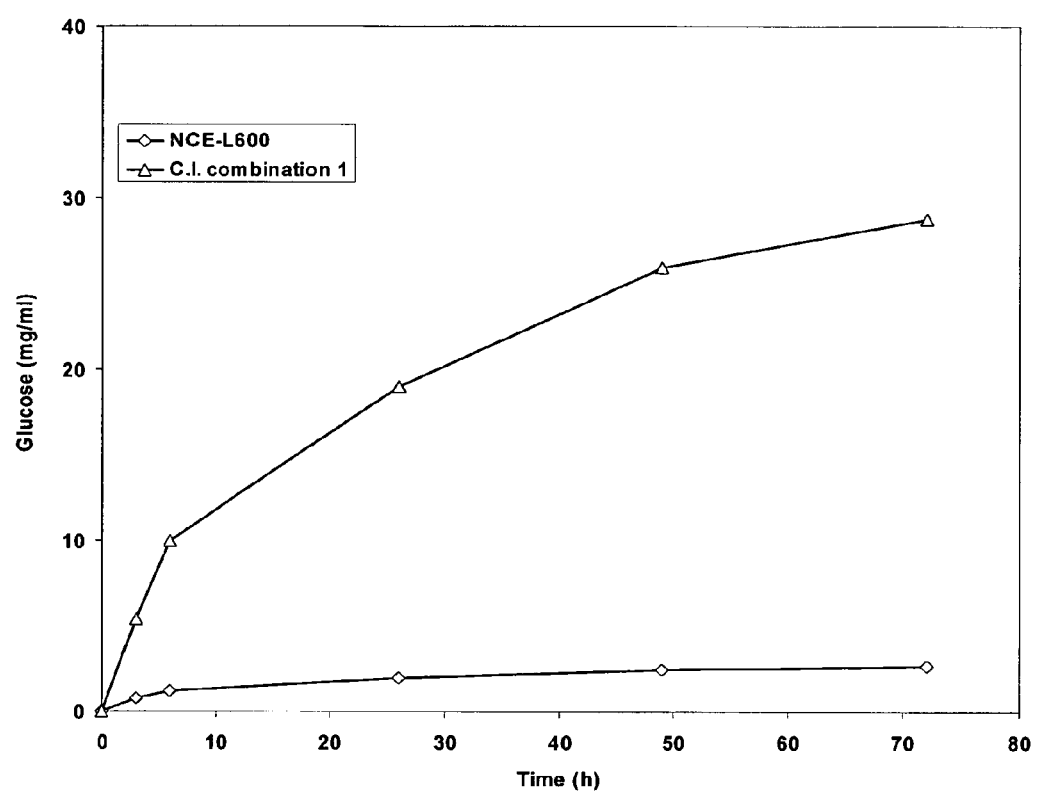
FIG. 6: Progress kinetics of hydrolysis of pretreated Douglas fir wood (50 mg ml$^{-1}$) by combination #1 of purified *C. lucknowense* enzymes and NCE-L 600, a commercial *C. lucknowense* at protein loading of 0.5 mg ml$^{-1}$, 50° C., pH 5.0 (see text and Table 4 for details).

Using four purified *C. lucknowense* enzymes (CBH Ia and IIb, EG II, BGL), an artificial cellulase complex was constructed (C.l. combination #1) that demonstrated an extremely high ability to convert different cellulosic substrates to glucose (FIGS. 4-6). This multienzyme composition was notably more effective in hydrolysis of pure crystalline cellulose (cotton and Avicel) than the crude *C. lucknowense* multienzyme preparation NCE-L600. In 72-h hydrolysis of a lignocellulosic substrate (Douglas fir wood pretreated by organosolv), the C.l. combination #1 was also very effective in cellulose hydrolysis.

In *C. lucknowense* combination #1, the enzyme consisted of the two cellobiohydrolases CBH Ia and CBH Ib, and the endoglucanase EG II, the enzymes with strong adsorption ability on crystalline cellulose (the molecules of these enzymes have CBM). The activity of tightly adsorbed cellulases is gradually decreased during in the course of hydrolysis of insoluble cellulose as a result of the enzyme limited mobility along the substrate surface or unproductive binding (so called pseudoinactivation). Without wishing to be bound by theory, it is believed that there may exist a synergism between tightly and loosely adsorbed cellulases wherein loosely binding cellulases (enzymes without CBM) may destroy obstacles hindering the processive action of the tightly adsorbed cellobiohydrolases, thus helping them to move to the next cellulose reactive sites. The total protein concentration in the reaction system was 0.5 mg ml$^{-1}$. The composition of the multienzyme composition (C.l. combination #1) was the following: 0.2 mg ml$^{-1}$ of CBH Ia+0.2 mg ml$^{-1}$ of CBH IIb+0.08 mg ml$^{-1}$ of EG II+0.02 mg ml$^{-1}$ of BGL. Avicel (50 mg ml$^{-1}$) and cotton (25 mg ml$^{-1}$) were used as substrates representing pure crystalline cellulose in these experiments. Sample of Douglas fir wood pretreated by organosolv (50 mg ml$^{-1}$) was taken as an example of real lignocellulosic feedstock that may be used for bioconversion to ethanol. A crude *C. lucknowense* multienzyme cellulase preparation NCE L-600 (diluted so that the protein concentration in the reaction system would also be 0.5 mg ml$^{-1}$) was taken for a comparison in these studies. The hydrolysis experiments with them were carried out also in the presence of extra added *A. japonicus* BGL (0.5 U ml$^{-1}$).

The progress kinetics of cotton, Avicel and Douglas fir hydrolysis by different cellulase multienzyme preparations are shown in FIGS. 4-6. It should be noted that in all cases, the concentrations of glucose and reducing sugars after 24-72 h of hydrolysis in a concrete experiment were practically the same, i.e. glucose made up >96% of the total soluble sugars. So, the glucose yield can be taken as reliable criterion in comparison of the hydrolytic efficiency of different multienzyme samples.

In hydrolysis of cotton (FIG. 4), the combination #1 of purified *C. lucknowense* enzymes provided much higher glucose yield after 72 h of the reaction (23.4 mg ml$^{-1}$, i.e. 84% degree of substrate conversion) than the 4.2 mg ml$^{-1}$ exhibited by (NCE-L600). In hydrolysis of Avicel (FIG. 5), the C.l. combination #1 was also superior (45.0 mg ml$^{-1}$ of glucose, or 81% substrate conversion after 72 h of hydrolysis). In the case of pretreated Douglas fir (FIG. 6), the C.l. combination #1 was also effective (28.8 mg ml$^{-1}$ glucose, 63% conversion after 72 hours).

Unlike Avicel and cotton, the pretreated wood sample contained not only cellulose (~85%) but also lignin (13%) and hemicellulose (2%). The artificial *C. lucknowense* four-enzyme combination #1 was composed of only cellulases; all of them, except for the BGL, having CBM. All other multienzyme samples possessed not only cellulase but also xylanase and other types of carbohydrase activity, i.e. they contained non-cellulase accessory enzymes. This may explain relatively lower efficiency of the C.l. combination #1 on pretreated Douglas fir compared to the *P. verruculosum* #151 preparation (FIG. 6).

In one set of experiments (FIG. 7), the pretreated wood sample was hydrolysed by different compositions of purified *C. lucknowense* enzymes, to which cellulases lacking a CBM were included (EG V or EG V in combination with CBH Ib). The total protein concentration in the reaction system was maintained at the same level of 0.5 mg ml$^{-1}$ (Table 5). Indeed, two C.l. combinations (#3 and #4), containing weakly adsorbed enzymes, provided a notable enhancement of the glucose yield after 72 h of the enzymatic reaction in comparison with the C.l. combination #1.

In two experiments, the highly active *C. lucknowense* Xyl II (Xyn11A) was added to the above-mentioned four enzymes (C.l. combinations #2 and #4). Since a synergism between tightly and loosely adsorbed cellulases has been described [38], EG V or EG V together with CBH Ib (both enzymes have lack CBM) were used in the C.l. combinations #3 and #4.

Figure 7:
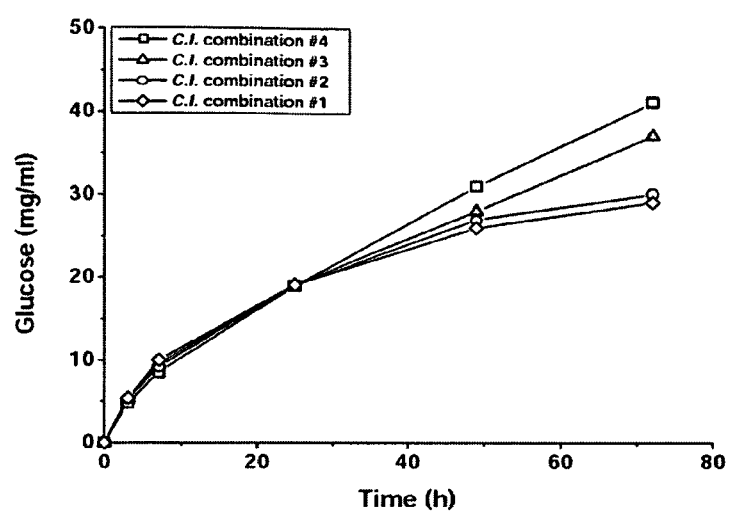
FIG. 7: Progress kinetics of hydrolysis of pretreated Douglas fir wood (50 mg ml$^{-1}$) by different combinations of purified *C. lucknowense* enzymes at protein loading of 0.5 mg ml$^{-1}$, 50° C., pH 5.0 (see text and Table 5 for details).

As can be seen from FIG. 7, the initial rate of glucose formation decreased sequentially from C.l. combination #1 to combination #4, however the glucose yield after 2-3 days of hydrolysis increased in the same sequence. The Xyl II demonstrated only slight positive effect on the glucose yield, while the EG V or EG V together with CBH Ib provided a very notable increase in the product concentration after 72 h hydrolysis of wood (37 and 41 mg ml$^{-1}$, respectively) compared to the C.l. combination #1 (29 mg ml$^{-1}$), i.e. the combinations #3 and #4 performed much better than all crude multienzyme samples (FIG. 6).

The low performance of the crude *C. lucknowense* preparation (NCE-L600) in hydrolysis of different cellulosic substrates (FIGS. 4-6) deserves a special attention. Without wishing to be bound by theory, it may be explained by the low total content of different cellobiohydrolases in the NCE-L600 (35-40% of the total protein content). Moreover, two of four *C. lucknowense* cellobiohydrolases (Ib and IIa) lack CBM, while two other enzymes (CBH Ia and IIb) also partially lose the CBM during the course of fermentation. The CBM absence in major part of cellobiohydrolases from the NCE-L600 may lead to the lower activity of the crude preparation toward crystalline cellulose.

TABLE 1

Identification of peptides in the isolated
*C. lucknowense* proteins using MALDI-TOF MS/MS

| Enzyme | m/z | Peptide$^a$ | BLAST identification$^b$ | UniProtKB No. |
|---|---|---|---|---|
| Protein 60 kDa | 1133.6 | HEYGTNIGSR | 118 HEYGTNIGSR 127 (cbh1.2 *Humicola grisea* - GH7) | O94093 |
| | 1829.9 | MGNQDFYGPGLTVDTK | 291 LGNTDFYGPGLTVDT 305 (cbhB *Aspergillus niger* - GH7) | Q9UVS8 |

TABLE 1-continued

Identification of peptides in the isolated
*C. lucknowense* proteins using MALDI-TOF MS/MS

| Enzyme | m/z | Peptide[a] | BLAST identification[b] | UniProtKB No. |
|---|---|---|---|---|
| Protein 70 kDa | 1061.4 | YPANDYYR | 127 ANNYYR 132 (Avicelase 2 *Humicola insolens* - GH6) | Q9C1S9 |
| | 1990.0 | HYIEAFSPLLNSAGFPAR | 367 KYIEAFSPLLNAAGFPA 383 (CBH II *Neurospora crassa* - GH6) | Q872J7 |
| | 2073.5 | LWQPTGQQQWGDWCNVK | 381 QPTGQQQWGDWCNV 394 (CBH II *T. reesei* - GH6) | P07987 |

[a]Since the MS/MS can not distinguish between Leu and Ile residues (they have the same masses), there may be ambiguity in the appropriate positions of the identified peptides.
[b]Residues conserved in the *C. lucknowense* enzymes are shown in bold.

TABLE 2

Specific activities (U mg$^{-1}$ of protein) of purified cellobiohydrolases from *C. lucknowense* toward different substrates at pH 5.0 and 40° C.

| Enzyme | Mol. mass (kDa) | Cat. domain designation | CBM presence | Avicel | CMC[a] | Barley β-glucan[a] | p-NP-β-D-cellobioside | p-NP-β-D-lactoside |
|---|---|---|---|---|---|---|---|---|
| CBH Ia | 65 | Cel7A | Yes | 0.21 | 0.1 | <0.1 | 0.021 | 0.12 |
| CBH Ib | 60 | Cel7B | No | 0.12 | 0.3 | <0.1 | 0.020 | 0.09 |
| CBH IIa | 43 | Cel6A | No | 0.08 | 1.1 | 2.0 | 0 | 0 |
| CBH IIb | 70 | Cel6B | Yes | 0.22 | 0.2 | 0.2 | 0 | 0 |

[a]Activity was determined at 50° C.

TABLE 3

Synergism between *C. lucknowense* cellulases in hydrolysis of cotton cellulose (5 mg ml$^{-1}$) at pH 5.0 and 40° C. in the presence of 0.5 U ml$^{-1}$ of *A. japonicus* BGL. In all cases the CBH concentration was 0.15 mg ml$^{-1}$, the EG concentration was 0.05 mg ml$^{-1}$.

| Enzyme | Glucose concentration after 140 h, experimental (mg ml$^{-1}$) | Glucose concentration after 140 h, theoretical[a] (mg ml$^{-1}$) | $K_{syn}$ |
|---|---|---|---|
| CBH Ia | 0.81 | — | — |
| CBH IIb | 1.18 | — | — |
| EG II | 0.64 | — | — |
| EG V | 0.70 | — | — |
| EG VI | 0.40 | — | — |
| CBH Ia + EG II | 4.05 | 1.45 | 2.79 |
| CBH Ia + EG V | 3.68 | 1.51 | 2.44 |
| CBH Ia + EG VI | 3.93 | 1.21 | 3.25 |
| CBH IIb + EG II | 4.72 | 1.82 | 2.59 |
| CBH IIb + EG V | 3.81 | 1.88 | 2.03 |
| CBH IIb + EGVI | 4.05 | 1.58 | 2.56 |
| CBH Ia + CBH IIb | 5.47 | 1.99 | 2.75 |

[a]Calculated as a sum of glucose concentrations obtained under the action of individual enzymes.

TABLE 4

Specific activities (U mg$^{-1}$ of protein) of multienzyme preparations toward different substrates at pH 5.0 and 50° C.

| Preparation | Protein (mg ml$^{-1}$ or mg g$^{-1}$) | Filter paper | CMC | Xylan | Cellobiose[a] |
|---|---|---|---|---|---|
| NCE-L600 | 45 | 0.25 | 12.2 | 4.8 | 0.07 |
| C.l. combination #1 | 1000 | 1.10 | 6.6 | 0 | 1.05 |

[a]Activity was determined at 40° C.

TABLE 5

Composition of artificial multienzyme combinations based on purified *C. lucknowense* enzymes and yields of glucose after 72-h hydrolysis of pretreated Douglas fir wood (50 mg ml$^{-1}$), pH 5.0, 50° C. The total protein concentration in the reaction system was 0.5 mg ml$^{-1}$, the concentration of each component and glucose yields are given in mg ml$^{-1}$.

| Combination | CBH Ia | CBH Ib | CBH IIb | EG II | EG V | BGL | Xyl II | Glucose yield |
|---|---|---|---|---|---|---|---|---|
| #01 | 0.2 | 0 | 0.2 | 0.08 | 0 | 0.02 | 0 | 28.8 |
| #02 | 0.2 | 0 | 0.2 | 0.07 | 0 | 0.02 | 0.01 | 30.1 |

TABLE 5-continued

Composition of artificial multienzyme combinations based on purified *C. lucknowense* enzymes and yields of glucose after 72-h hydrolysis of pretreated Douglas fir wood (50 mg ml$^{-1}$), pH 5.0, 50° C. The total protein concentration in the reaction system was 0.5 mg ml$^{-1}$, the concentration of each component and glucose yields are given in mg ml$^{-1}$.

| Combination | CBH Ia | CBH Ib | CBH IIb | EG II | EG V | BGL | Xyl II | Glucose yield |
|---|---|---|---|---|---|---|---|---|
| #03 | 0.2 | 0 | 0.2 | 0.04 | 0.04 | 0.02 | 0 | 37.3 |
| #04 | 0.1 | 0.1 | 0.2 | 0.03 | 0.04 | 0.02 | 0.01 | 41.0 |

We claim:

1. A method of producing a fermentation product or a starting material for a fermentation product from a fermentable sugar, wherein said method comprises: (a) providing an enzyme formulation, wherein said enzyme formulation comprises at least two enzymes selected from the group consisting of EG II (SEQ ID NO. 10) and BGL (SEQ ID NO 12); (b) applying said enzyme formulation to lignocellulosic material to produce a fermentable sugar; and (c) fermenting said fermentable sugar to produce a fermentation product.

2. The method according to claim 1, wherein the fermentable sugar is selected from the group consisting of glucose, xylose, arabinose, galactose, mannose, rhamnose, sucrose and fructose.

3. The method according to claim 1, wherein the lignocellulosic material is selected from the group consisting of orchard prunings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, prairie grass, gamagrass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn kernel, fiber from kernels, products and by-products from wet or dry milling of grains, municipal solid waste, waste paper, yard waste, herbaceous material, agricultural residues, forestry residues, municipal solid wastes, waste paper, pulp, paper mill residues, branches, bushes, canes, corn, corn husks, energy crops, forests, fruits, flowers, grains, grasses, herbaceous crops, leaves, bark, needles, logs, roots, saplings, shrubs, switch grasses, trees, vegetables, fruit peels, vines, sugar beet pulp, wheat midlings, oat hulls, hard and soft woods, organic waste materials generated from agricultural processes, forestry wood waste, or combinations thereof.

4. The method according to claim 1, wherein said fermentation product is a biofuel.

5. The method according to claim 1, wherein said fermentation product is selected from the group consisting of lactic acid, organic acids, animal feed supplements, pharmaceuticals, vitamins, amino acids, industrial enzymes, and chemical feedstocks.

6. The method according to claim 4, wherein said combustible fermentation product is an alcohol.

7. The method according to claim 1, wherein the lignocellulosic material is subjected to a pretreatment prior to being exposed to enzymes;
wherein said pretreatment comprises exposing the lignocellulosic biomass to an acid, base, solvent, heat, peroxide, ozone, mechanical shredding, grinding, milling, rapid depressurization, or a combination thereof.

8. The method according to claim 7, wherein said solvent is an acetone/ethanol mixture or organosolv.

9. A method for degrading a lignocellulo sic material to fermentable sugars, said method comprising contacting the lignocellulosic material with an effective amount of a multi-enzyme product derived from a microorganism, to produce at least one fermentable sugar wherein at least one of enzyme in the multi-enzyme product is selected from the group consisting of EG II (SEQ ID NO. 10) and BGL (SEQ ID NO. 12).

10. A method of producing energy from a fermentable sugar, said method comprising (a) providing an enzyme formulation, wherein said enzyme formulation comprises at least one enzyme selected from the group consisting of EG II (SEQ ID NO. 10) and BGL (SEQ ID NO 12); (b) applying said enzyme formulation to lignocellulosic material to produce a fermentable sugar; (c) fermenting said fermentable sugar to produce a combustible fermentation product; (d) combusting said combustible fermentation product to produce energy.

11. The method according to claim 10, wherein the fermentable sugar is selected from the group consisting of glucose, xylose, arabinose, galactose, mannose, rhamnose, sucrose and fructose.

12. The method according to claim 10, wherein the lignocellulosic material is selected from the group consisting of orchard prunings, chaparral, mill waste, urban wood waste, municipal waste, logging waste, forest thinnings, short-rotation woody crops, industrial waste, wheat straw, oat straw, rice straw, barley straw, rye straw, flax straw, soy hulls, rice hulls, rice straw, corn gluten feed, oat hulls, sugar cane, corn stover, corn stalks, corn cobs, corn husks, prairie grass, gamagrass, foxtail; sugar beet pulp, citrus fruit pulp, seed hulls, cellulosic animal wastes, lawn clippings, cotton, seaweed, trees, shrubs, grasses, wheat, wheat straw, sugar cane bagasse, corn, corn husks, corn kernel, fiber from kernels, products and by-products from wet or dry milling of grains, municipal solid waste, waste paper, yard waste, herbaceous material, agricultural residues, forestry residues, municipal solid wastes, waste paper, pulp, paper mill residues, branches, bushes, canes, corn, corn husks, energy crops, forests, fruits, flowers, grains, grasses, herbaceous crops, leaves, bark, needles, logs, roots, saplings, shrubs, switch grasses, trees, vegetables, fruit peels, vines, sugar beet pulp, wheat midlings, oat hulls, hard and soft woods, organic waste materials generated from agricultural processes, forestry wood waste, or combinations thereof.

13. The method according to claim 10, wherein said combustible fermentation product is an alcohol.

14. The method according to claim 10, wherein the lignocellulosic material is subjected to a pretreatment prior to being exposed to enzymes;
   wherein said pretreatment comprises exposing the lignocellulosic biomass to an acid, base, solvent, heat, peroxide, ozone, mechanical shredding, grinding, milling, rapid depressurization, or a combination thereof.

15. The method according to claim 14, wherein said solvent is an acetone/ethanol mixture or organosolv.

* * * * *

SEQUENCE LISTING

<160> NUMBER OF SEQ ID NOS: 28

<210> SEQ ID NO 1
<211> LENGTH: 6360
<212> TYPE: DNA
<213> ORGANISM: Chrysosporium lucknowense

<400> SEQUENCE: 1

```
ctcagattct aggggtaggg cgggagcaga ggcgaaaatt gggttgtaga atatgaggag      60
ctagggttgt taaactcaaa gaacttcttg ctcttgttct tagtcttctc tcctgggaaa     120
aggggttttt tccgaaagcg cgcctatacg aagccagagg ctactttcct tgctttggat     180
ggcccttgtc caccgttctt gtttcccgtt tgtcaattgc gacgttgccg gcaacctagg     240
tcctaataat taggtagata tttcggtaga ggtagtttaa ttatgcttca gtagagaaat     300
cgttgtctcc acgtctcgca accttgcgaa acttcgccac attgaagata gcattgtctg     360
agttgatttt aacccttcc agagacgata taatagtgca gtttctttg atcggaatca      420
tcgacattcg gatttttccct taattatatg aagtattcgg cccacggaac cgggccccga     480
gcaggttgaa ccgcgcaaaa cctcaaccga gtcacctcgc gtccatgttt gtcatggaat     540
caggctccga atcccgtcag atcagtcagt tctggtggct atggacgcgg gagttacggc     600
cagtcgtccc gttgttctgg ggggttgatc aacaggagga agagatctga gatcgaacta     660
cacccattga tttatcgacg cataatcaag tttaataaaa accaaacagc gtgtttggtg     720
ctaccaccga atgcgagatc cgggctagcc cgcggaagga tgatggccac agatctagcg     780
tcatgtatga ttattaccta tgcatctatc ttcgtatctg cctcgggttg caacacctg     840
accgagagac gactcgacaa cctgacactt ggcaaaagac atttcggttg acagcgggag     900
aactccagcg aggaagtcgc ccagagatgc ggatgagaag acaacgccga gacgtgccgg     960
cgttggctct ccacgaatcg gagccgactc ttccgtttgg ccaatctccg ggataaatcc    1020
cagcggcggg tcacgtcacg tttcatgggg aggcgcggac agccatccca gccaggccat    1080
ggaagagaac aattcttggg ggtagcgacc gagccaaaag gggggggggg gaagcgggag    1140
gggaagaagt ggtattagag cacgcaccgg aaaacgcatt tgggcccttg ccaacaaaca    1200
ccacaccccg cgtcctggga gcaagacatc caggatgcaa cccagtaggg gatgccaaga    1260
agcatctacg gcaccatctg ccggcgcctc gcctgttaga gtcccggcac ccgccaatgg    1320
ggccgtgctg ggccctgccc ggcaatgctg gcgcagcggc atcaacaaca ttgctcgggg    1380
aggggcccga tttattgat tagcaaaaaa acaattaaat tacccttcca ttccagcaga    1440
gcttctcctc cacgcggcgg cgggaccgct tgtggacggc ggtacactac aaccgcgggg    1500
ctccagtctc cgtgctgggc gtgcagatca cgacccggaa gagaaatgat cgcggtctga    1560
cgccgggtac ggagtactga gccgccaacc acagccgatg gaccgtgata tctcaatgcg    1620
```

-continued

```
ttcaagcaac acagcaacac cctggacgag tctctcctcc cctaccaccc cctccccccc    1680
tgccctggcc gcgaacgggg cgcgtacccc agatttctac tccgtactga cacccccaatc    1740 tattcccgct ggcgtcgccc agtctggggc ggtccggcca agactctcgg tgcacgatac    1800
cgcgacgaaa tcggattaac cgttggctga tcaattccaa gtcaagggag aagtggtatg    1860
gaaagtcggc tcagttttcc actgccccg acaggcaggt tccggatctg gacagcagtc     1920
ttccgaatct ttggcagaga ctcatgataa tataaaaagg caaatgaggc ggcgccttgg    1980
acaggtccat tctcccaccg ctcaaccagc ctccaattcc tcagaagtct gttgctctct    2040
cgcagtcgca gtcaagatga agcagtacct ccagtacctc gcggcgaccc tgcccctggt    2100
gggcctggcc acggcccagc aggcgggtaa cctgcagacc gagactcacc ccaagctcac    2160
ttggtcgaag tgcacggccc cgggatcctg ccaacaggtc aacggcgagg tcgtcatcga    2220
ctccaactgg cgctgggtgc acgacgagaa cgcgcagaac tgctacgacg gcaaccagtg    2280
gaccaacgct tgcagctctg ccaccgactg cgccgagaat tgcgcgctcg agggtgccga    2340
ctaccagggc acctatggcg cctcgaccag cggcaatgcc ctgacgctca ccttcgtcac    2400
taagcacgag tacggcacca acattggttc gcgcctctac ctcatgaacg cgcgaacaa     2460 gtaccagatg ttcacccctca agggcaacga gctggccttc gacgtcgacc tctcggccgt    2520
cgagtgcggc ctcaacagcg ccctctactt cgtggccatg gaggaggatg gcggtgtgtc    2580
gagctacccg accaacacgg ccggtgctaa gttcggcact ggggtaagtt caacgacccg    2640
agacgggtgc ccttattatc tgctgcgaaa acggacggtc ccctttgct aactaccctc      2700 ctccaaacag tactgcgacg cccaatgcgc acgcgacctc aagttcgtcg gcggcaaggg    2760
caacatcgag ggctggaagc cgtccaccaa cgatgccaat gccggtgtcg gtccttatgg     2820
cgggtgctgc gctgagatcg acgtctggta agttttgttg cctgggcagc aatggtatat    2880
tagctcgagt ggttcccgtc gttgctgacc ctctcttacc agggagtcga acaagtatgc    2940
tttcgctttc accccgcacg gttgcgagaa ccctaaatac cacgtctgcg agaccaccaa    3000
ctgcggtggc acctactccg aggaccgctt cgctggtgac tgcgatgcca acggctgcga    3060 ctacaaccccc taccgcatgg gcaaccagga cttctacggt cccggcttga cggtcgatac    3120
cagcaagaag ttcacgtgag tacaccgtgc ttgaagcccc ctccccccc cccccaaaa      3180 aaaaaaagaa aaaagaagtc aaatgattga tgctaaccaa atcaaataac agcgtcgtca    3240
gccagttcga ggagaacaag ctcacccagt tcttcgtcca ggacggcaag aagattgaga    3300
tccccggccc caaggtcgag ggcatcgatg cggacagcgc cgctatcacc cctgagctgt    3360
gcagtgccct gttcaaggcc ttcgatgacc gtgaccgctt ctcggaggtt ggcggcttcg    3420
atgccatcaa cacggccctc agcactccca tggtcctcgt catgtccatc tgggatgatg    3480
tacgttacct aaccccccc cccttttttt ttcccgcttc tctccccgaa actgccacta     3540
cttatatacg tcccgcgtcc atgatgctta ccttttctcc ttccagcact acgccaatat    3600
gctctggctc gactcgagct acccccctga gaaggctggc cagcctggcg gtgaccgtgg    3660
cccgtgtcct caggactctg gcgtcccggc cgacgttgag gctcagtacc ctaatgcgtg    3720
agtcgaaacc gtaaaatgtc gggcaaaaaa aagatcgctc aagctaacga aataatatga    3780
ttagcaaggt catctggtcc aacatccgct tcggcccat cggctcgact gtcaacgtct     3840
aaactgcaac ctgaccgggc cctttctctc caccccacc cctctcaagt tctctctggt    3900
ggagccctcg tgtccttctt ttcctaggtt cgcgaacctt tgagcttgtg tatccgtaggg   3960 tcattgtgta catacacaaa aacttaacat ctgctaccaa gatcttggcg ctttgccagg   4020
```

```
tcttctcaaa cctcgaagca ctgagccttt gtcctccgag tgaagtagga tgactattta    4080
cgttgcaaga ctacgcggta aagggggacgg agcagacctg ccacagatat tcgtttggtt    4140
gcttgattta tagcagagtc cgaacgtaga catggcccct gaaggtgcca accctagata    4200
gccagaagcc ttgttttacg aaagggtggt caaccaacgg tgctcctcgc tcagcgaatc    4260
tacccgcacg caatgtatcg taagaatgtg aactaaaggg aacgacgagg catagggaaa    4320
cgtcaatgtg gcttgaataa cagagttaaa tacctaatag aagaaattag catgccaaga    4380
ttgagccagc aacacatggt agaatagcca gcaaaggacg cttgttcgct tgatctcgaa    4440
ccgtccaacc tgattcgaag gaggaggaa aagttgaaga ataccggcaa taattactcg    4500
aggttcctat gccctgcaga gtctaattaa tattaaaggc accacccgca tgattccgca    4560
attataagca taataagctc gcgggcccca cacgtgcctt caccctccca tgtgtataca    4620
atctgtacct cgttattgtc gaatcgctat tccgatagcg aaggtctggc actcatcaga    4680
taccgtgaca tcgattgaga tttggccggg ccaccggtag taagcgatga gttggtcatc    4740
aattatcaac aatgcgctca atcagcgata tcagcctat caaccgcgaa atcatacgcg    4800
catcaacgaa ttgtccatca tgcacgtagc ttgtcggcag tgccgcatac cctccagagc    4860
atcatagccg ggatagaaag ctcgctttca gccgtcccag agtccgagat gcaggtagca    4920
agccttcaag accagttata tgtgacccgg gtaaaatact tggtgagatg caatgggcgt    4980
agcttcgggc acttataagc tttactagat attatctcaa ggtttctttt tgaactcctc    5040
ctagacattt actataaact accgagcttc aatgctagac gccctccttc tgttaaatag    5100
tcttttcctt ctaagagcat ctgccttttt tcccttaggc ttagaggata gggcccctcc    5160
atcttgctgc gacggcctta gccttgggga gtaattattg gtatccgcgt acctgtttcc    5220
cagacagccg aagtttcgac gacaaagtaa ttattgcgac aataccaccg ccatatgcta    5280
ttccgagtgg gtgagccccg aaaacatcgc ttaccgcatc gccatcccag acgacagagg    5340
gcgactttga tgtcttgctc cagatcgccg cacctaacac ggtgggatgg gctggtatcg    5400
tatgggacgg catcatggtc aacaaccccc tgacggggtg ttgggccaat ggaaacacca    5460
ccgttgtctc gagccggatc gcaaggtaag ccgaagagga caaatgacga tgagactttc    5520
tttctttttt attttatttt tttttaaatt tcttttttaa gcgtaatgaa aagagctaca    5580
tatctgtggt tcgttcctca atttcagcga cctctccacc gaagcatcgt caaataagaa    5640
gttgtcggaa acaaagggtg tcagaagcta tagagcttct aaggatatta gccacataca    5700
tgccatagct gtataaggct atttaacgct ttggccagtc cctttgtcta taaatattag    5760
tcgttttgtc tcctttgtag ataatttaaa caaggcactc ttttccttta tatagccacc    5820
tactatagac tgctttcaac gctcccggaa gcttattact acgttcggca gttataagcc    5880
tggcgccttg actactcctc tgccgacgta tctttaatat tagtagtagc ttcttctatt    5940
acgaactctc ttaccctgct ttaatacgct ttcgacgacg tgtctattat atctaagatc    6000
ctagtcgaga cttctatatg ccttactagg cctagttctt agaacttgta gtatattaaa    6060
ctatagttat aggctaaatt tgctagtata tagagatttg ttaaccttaa tagtaattat    6120
aaactagatc tagaagtttt atagtgccta acctataaat aagctagaga taaccttatt    6180
ttagcttcct aggagtaatt cctagaagga gtattccctt taatatctat agatttgata    6240
ccttctaata tagctatcat agctaaattt atataattat aagattccctt ttataaaaat    6300
attatatata ctatagatat tagtaagtag ataggatagc tataatacta gctagtatat    6360
```

<210> SEQ ID NO 2
<211> LENGTH: 450
<212> TYPE: PRT
<213> ORGANISM: Chrysosporium lucknowense

<400> SEQUENCE: 2

```
Met Lys Gln Tyr Leu Gln Tyr Leu Ala Ala Thr Leu Pro Leu Val Gly
1               5                   10                  15

Leu Ala Thr Ala Gln Gln Ala Gly Asn Leu Gln Thr Glu Thr His Pro
            20                  25                  30

Lys Leu Thr Trp Ser Lys Cys Thr Ala Pro Gly Ser Cys Gln Gln Val
        35                  40                  45

Asn Gly Glu Val Val Ile Asp Ser Asn Trp Arg Trp Val His Asp Glu
    50                  55                  60

Asn Ala Gln Asn Cys Tyr Asp Gly Asn Gln Trp Thr Asn Ala Cys Ser
65                  70                  75                  80

Ser Ala Thr Asp Cys Ala Glu Asn Cys Ala Leu Glu Gly Ala Asp Tyr
                85                  90                  95

Gln Gly Thr Tyr Gly Ala Ser Thr Ser Gly Asn Ala Leu Thr Leu Thr
            100                 105                 110

Phe Val Thr Lys His Glu Tyr Gly Thr Asn Ile Gly Ser Arg Leu Tyr
        115                 120                 125

Leu Met Asn Gly Ala Asn Lys Tyr Gln Met Phe Thr Leu Lys Gly Asn
    130                 135                 140

Glu Leu Ala Phe Asp Val Asp Leu Ser Ala Val Glu Cys Gly Leu Asn
145                 150                 155                 160

Ser Ala Leu Tyr Phe Val Ala Met Glu Glu Asp Gly Gly Val Ser Ser
                165                 170                 175

Tyr Pro Thr Asn Thr Ala Gly Ala Lys Phe Gly Thr Gly Tyr Cys Asp
            180                 185                 190

Ala Gln Cys Ala Arg Asp Leu Lys Phe Val Gly Gly Lys Gly Asn Ile
        195                 200                 205

Glu Gly Trp Lys Pro Ser Thr Asn Asp Ala Asn Ala Gly Val Gly Pro
    210                 215                 220

Tyr Gly Gly Cys Cys Ala Glu Ile Asp Val Trp Glu Ser Asn Lys Tyr
225                 230                 235                 240

Ala Phe Ala Phe Thr Pro His Gly Cys Glu Asn Pro Lys Tyr His Val
                245                 250                 255

Cys Glu Thr Thr Asn Cys Gly Gly Thr Tyr Ser Glu Asp Arg Phe Ala
            260                 265                 270

Gly Asp Cys Asp Ala Asn Gly Cys Asp Tyr Asn Pro Tyr Arg Met Gly
        275                 280                 285

Asn Gln Asp Phe Tyr Gly Pro Gly Leu Thr Val Asp Thr Ser Lys Lys
    290                 295                 300

Phe Thr Val Val Ser Gln Phe Glu Glu Asn Lys Leu Thr Gln Phe Phe
305                 310                 315                 320

Val Gln Asp Gly Lys Lys Ile Glu Ile Pro Gly Pro Lys Val Glu Gly
                325                 330                 335

Ile Asp Ala Asp Ser Ala Ala Ile Thr Pro Glu Leu Cys Ser Ala Leu
            340                 345                 350

Phe Lys Ala Phe Asp Asp Arg Asp Arg Phe Ser Glu Val Gly Gly Phe
        355                 360                 365

Asp Ala Ile Asn Thr Ala Leu Ser Thr Pro Met Val Leu Val Met Ser
    370                 375                 380
```

```
Ile Trp Asp Asp His Tyr Ala Asn Met Leu Trp Leu Asp Ser Ser Tyr
385                 390                 395                 400

Pro Pro Glu Lys Ala Gly Gln Pro Gly Gly Asp Arg Gly Pro Cys Pro
            405                 410                 415

Gln Asp Ser Gly Val Pro Ala Asp Val Glu Ala Gln Tyr Pro Asn Ala
        420                 425                 430

Lys Val Ile Trp Ser Asn Ile Arg Phe Gly Pro Ile Gly Ser Thr Val
        435                 440                 445

Asn Val
    450

<210> SEQ ID NO 3
<211> LENGTH: 3900
<212> TYPE: DNA
<213> ORGANISM: Chrysosporium lucknowense

<400> SEQUENCE: 3
```

| | | | | | |
|---|---|---|---|---|---|
| ccgcaagtga | atatgtaatt | actcaatgga | agttctcgaa | acggagtcca | gaaatgatgt | 60 |
| ggttctgtgg | gaatgcggca | agaggcgacg | ttgccgtgaa | tgcgtgaaca | ttcccgcctc | 120 |
| ttcttcttct | cgtcttcttc | cttcttcttc | tttcgggtcg | cggatggttg | acggccagcg | 180 |
| tgcgcacggc | tgcgtgttat | cgagcgtcgg | tacgtctagc | caacatcccg | tagacacgac | 240 |
| gaccaagcgt | cttgagaatg | caacaacgtc | tcggaacctg | cacgcatct | tccgccgcag | 300 |
| gtcggcagac | gccgcctggg | caataccacc | cctgtccagg | ccctttcccc | gcaggcagag | 360 |
| ccgcgctctt | cctttcatgg | ttattcagga | acgtggcttc | cgagattctc | gcctgttctc | 420 |
| ccccagtcaa | cctgccgacc | gtaacccggt | tccaccaccg | cggactgtcc | gcaaaacctg | 480 |
| gttcgcccga | gattaatatg | ctatttccgg | actaagtgca | caacacacaa | gcaccccttc | 540 |
| cgcctcgcgc | tctagaatct | gctttctaac | ccggttctcg | ggcccttccc | tttcgcgacg | 600 |
| cctccgctct | ccttaccagg | caccatccgc | aataggtaag | gtagccaacc | gttttggagc | 660 |
| gtgattctgc | caaggaccgc | atccttgcat | cgccatctg | gtcaaggacc | cctctttccc | 720 |
| gctccattct | ggtggctcta | tcgggacggc | gttccccatg | gctctccagg | agagtgatgt | 780 |
| gcgagtctgg | agagccgggg | ttggcgtcac | gatgctgccc | acctagggcc | ggccagcccg | 840 |
| gcactgcgct | cccgttgatc | cgtctatccc | cgtcaagagc | accagccccg | gcgctcgtga | 900 |
| attttcgact | tgttcgactt | gctacaggtg | ataaagagga | tgcacgccgc | cctcgatcgg | 960 |
| cctgtgtggt | ttctctccct | cgtgccaaac | cactcccacc | tcccgccccg | agatagttgc | 1020 |
| ttgtttcgct | ccgtgagagg | gacacacacc | aatggccaag | aagcttttca | tcaccgccgc | 1080 |
| gcttgcggct | gccgtgttgg | cggccccccgt | cattgaggag | cgccagaact | gcggcgctgt | 1140 |
| gtggtaagaa | agcccggtcc | gagtctccca | tgattttctc | gtcgagtaat | ggcataaggg | 1200 |
| ccaccccttc | gactgaccgt | gagaatcgat | caaatccagg | actcaatgcg | gcggtaacgg | 1260 |
| gtggcaaggt | cccacatgct | gcgcctcggg | ctcgacctgc | gttgcgcaga | acgagtggta | 1320 |
| ctctcagtgc | ctgcccaaca | gccaggtgac | gagttccacc | actccgtcgt | cgacttccac | 1380 |
| ctcgcagcgc | agcaccagca | cctcagcag | caccaccagg | agcggcagct | cctcctcctc | 1440 |
| ctccaccacg | ccccgccccg | tctccagccc | cgtgaccagc | attccggcg | gtgcgacctc | 1500 |
| cacggcgagc | tactctggca | accccttctc | gggcgtccgg | ctcttcgcca | acgactacta | 1560 |
| caggtccgag | gtccacaatc | tcgccattcc | tagcatgact | ggtactctgg | cggccaaggc | 1620 |
| ttccgccgtc | gccgaagtcc | ctagcttcca | gtggctcgac | cggaacgtca | ccatcgacac | 1680 |

-continued

```
cctgatggtc cagactctgt cccaggtccg ggctctcaat aaggccggtg ccaatcctcc    1740
ctatgctggt gagttacatg gcgacttgcc ttctcgtccc ctacctttct tgacgggatc    1800
ggttacctga cctggaggca aaacaacaac agcccaactc gtcgtctacg acctccccga    1860
ccgtgactgt gccgccgctg cgtccaacgg cgagttttcg attgcaaacg cggcgccgc    1920 caactacagg agctacatcg acgctatccg caagcacatc attgagtact cggacatccg    1980
gatcatcctg gttatcgagc ccgactcgat ggccaacatg gtgaccaaca tgaacgtggc    2040
caagtgcagc aacgccgcgt cgacgtacca cgagttgacc gtgtacgcgc tcaagcagct    2100
gaacctgccc aacgtcgcca tgtatctcga cgccggccac gccggctggc tcggctggcc    2160
cgccaacatc cagcccgccg ccgagctgtt tgccggcatc tacaatgatg ccggcaagcc    2220
ggctgccgtc cgcggcctgg ccactaacgt cgccaactac aacgcctgga gcatcgcttc    2280
ggccccgtcg tacacgtcgc ctaaccctaa ctacgacgag aagcactaca tcgaggcctt    2340
cagcccgctc ttgaactcgg ccggcttccc cgcacgcttc attgtcgaca ctggccgcaa    2400
cggcaaacaa cctaccggta tgttttttttt tcttttgtct ctgtcccccc cttttctccc    2460
ccttcagttg gcgtccacaa ggtctcttag tcctgcttca tctgtgacca acctcccccc    2520
ccccggcacc gcccacaacc gtttgactct atactcttgg gaatgggcgc cgaaactgac    2580
cgttccacag gccaacaaca gtggggtgac tggtgcaatg tcaagggcac cggctttggc    2640
gtgcgcccga cggccaacac gggccacgag ctggtcgatg cctttgtctg ggtcaagccc    2700
ggcggcgagt ccgacggcac aagcgacacc agcgccgccc gctacgacta ccactgcggc    2760
ctgtccgatg ccctgcagcc tgcccccgag gctggacagt ggttccaggc ctacttcgag    2820
cagctgctca ccaacgccaa cccgcccttc taaacctcgt cataaagaga gagagatggc    2880
gggcatgggc ctgattgggt tcattgacca tgcggctctt ctgggggtac atattttacc    2940
tacctaccta taaataaggc ggcctatcgg gctctcgctt cgtttattag gtacttgttc    3000
ttgtacatac tttgtttata catacagcag ttagcatcca ctattcgttt cgacaaagcg    3060
gaactttcca gaaaaaaaaa ggttgtacat aattagtctt taggcttcga ttctttgtgc    3120
cttttctttt ggtaaaaaaa aaattttttt tgaggcatga ttaccttagg tacgttcgtc    3180
gttgtattgg tccccctgca tttttggcgcg agagcagctc agccccttgc aaatccctca    3240
acgggcgttc aattccctcc actcgggtct tcagcgagac cagccgtcca gagtatccca    3300
gcgtgtagtt gccccacgaa ccagtcgtcc tcgtaagcct cgtcaaagtg tccaagagca    3360
gtatagaagc aacgacctcc gtcaaaagtc tggcaccatg cgatcgggtg gtcctccccg    3420
tgcgccccgc cctcgtagga cttctcatcc acgccaagga gcacgtgcag gccgtcggac    3480
gtcgcccgcg ggtgcgcctt gaagttgtac cattcgtcct tccagacgcg ctccagctgc    3540
gcctgcttgg gttcctgcgg ttcctgcggt tcctgcgctg gccggtcggc gccgccgtct    3600
tggtcacacg cccgcagcga catgactggg tgtttcgggt cgagcagctt gacgagcccg    3660
acctggggtt ccgggtggtt gtcgaacacg gcgccaatga ggtggccgta ccattcggat    3720
gactgcatgg cgaagctggc gcagtgtacc gccacgatcc gccgcccgc ctggacgaaa    3780 ccccgcaggg cgcccagctg cgcgccgtcc aggaactcgc ccgagcactg caggaggacg    3840
atgacgcgat acgccgagag ggagccgggg ctgaacacgg cgggatcctc gctgtcgtcc    3900
```

<210> SEQ ID NO 4
<211> LENGTH: 481
<212> TYPE: PRT

<213> ORGANISM: Chrysosporium lucknowense

<400> SEQUENCE: 4

```
Met Ala Lys Lys Leu Phe Ile Thr Ala Ala Leu Ala Ala Ala Val Leu
1               5                   10                  15

Ala Ala Pro Val Ile Glu Glu Arg Gln Asn Cys Gly Ala Val Thr Gln
            20                  25                  30

Cys Gly Gly Asn Gly Trp Gln Gly Pro Thr Cys Cys Ala Ser Gly Ser
        35                  40                  45

Thr Cys Val Ala Gln Asn Glu Trp Tyr Ser Gln Cys Leu Pro Asn Ser
    50                  55                  60

Gln Val Thr Ser Ser Thr Thr Pro Ser Ser Thr Ser Thr Ser Gln Arg
65                  70                  75                  80

Ser Thr Ser Thr Ser Ser Ser Thr Thr Arg Ser Gly Ser Ser Ser Ser
                85                  90                  95

Ser Ser Thr Thr Pro Pro Pro Val Ser Ser Pro Val Thr Ser Ile Pro
            100                 105                 110

Gly Gly Ala Thr Ser Thr Ala Ser Tyr Ser Gly Asn Pro Phe Ser Gly
        115                 120                 125

Val Arg Leu Phe Ala Asn Asp Tyr Tyr Arg Ser Glu Val His Asn Leu
    130                 135                 140

Ala Ile Pro Ser Met Thr Gly Thr Leu Ala Ala Lys Ala Ser Ala Val
145                 150                 155                 160

Ala Glu Val Pro Ser Phe Gln Trp Leu Asp Arg Asn Val Thr Ile Asp
                165                 170                 175

Thr Leu Met Val Gln Thr Leu Ser Gln Val Arg Ala Leu Asn Lys Ala
            180                 185                 190

Gly Ala Asn Pro Pro Tyr Ala Ala Gln Leu Val Val Tyr Asp Leu Pro
        195                 200                 205

Asp Arg Asp Cys Ala Ala Ala Ala Ser Asn Gly Glu Phe Ser Ile Ala
    210                 215                 220

Asn Gly Gly Ala Ala Asn Tyr Arg Ser Tyr Ile Asp Ala Ile Arg Lys
225                 230                 235                 240

His Ile Ile Glu Tyr Ser Asp Ile Arg Ile Ile Leu Val Ile Glu Pro
                245                 250                 255

Asp Ser Met Ala Asn Met Val Thr Asn Met Asn Val Ala Lys Cys Ser
            260                 265                 270

Asn Ala Ala Ser Thr Tyr His Glu Leu Thr Val Tyr Ala Leu Lys Gln
        275                 280                 285

Leu Asn Leu Pro Asn Val Ala Met Tyr Leu Asp Ala Gly His Ala Gly
    290                 295                 300

Trp Leu Gly Trp Pro Ala Asn Ile Gln Pro Ala Ala Glu Leu Phe Ala
305                 310                 315                 320

Gly Ile Tyr Asn Asp Ala Gly Lys Pro Ala Ala Val Arg Gly Leu Ala
                325                 330                 335

Thr Asn Val Ala Asn Tyr Asn Ala Trp Ser Ile Ala Ser Ala Pro Ser
            340                 345                 350

Tyr Thr Ser Pro Asn Pro Asn Tyr Asp Glu Lys His Tyr Ile Glu Ala
        355                 360                 365

Phe Ser Pro Leu Leu Asn Ser Ala Gly Phe Pro Ala Arg Phe Ile Val
    370                 375                 380

Asp Thr Gly Arg Asn Gly Lys Gln Pro Thr Gly Gln Gln Gln Trp Gly
385                 390                 395                 400
```

```
Asp Trp Cys Asn Val Lys Gly Thr Gly Phe Gly Val Arg Pro Thr Ala
            405                 410                 415

Asn Thr Gly His Glu Leu Val Asp Ala Phe Val Trp Val Lys Pro Gly
        420                 425                 430

Gly Glu Ser Asp Gly Thr Ser Asp Thr Ser Ala Ala Arg Tyr Asp Tyr
            435                 440                 445

His Cys Gly Leu Ser Asp Ala Leu Gln Pro Pro Glu Ala Gly Gln
        450                 455                 460

Trp Phe Gln Ala Tyr Phe Glu Gln Leu Leu Thr Asn Ala Asn Pro Pro
465                 470                 475                 480

Phe
```

<210> SEQ ID NO 5
<211> LENGTH: 1648
<212> TYPE: DNA
<213> ORGANISM: Chyrsosporium lucknowense
<220> FEATURE:
<221> NAME/KEY: misc_feature
<222> LOCATION: (812)..(812)
<223> OTHER INFORMATION: n is a, c, g, or t
<220> FEATURE:
<221> NAME/KEY: misc_feature
<222> LOCATION: (1162)..(1162)
<223> OTHER INFORMATION: n is a, c, g, or t

<400> SEQUENCE: 5

```
atgtacgcca agttcgcgac cctcgccgcc cttgtggctg gcgccgctgc tcagaacgcc      60
tgcactctga ccgctgagaa ccaccccctcg ctgacgtggt ccaagtgcac gtctggcggc    120
agctgcacca gcgtccaggg ttccatcacc atcgacgcca actggcggtg gactcaccgg    180
accgatagcg ccaccaactg ctacgagggc aacaagtggg atacttcgta ctgcagcgat    240
ggtccttctt gcgcctccaa gtgctgcatc gacggcgctg actactcgag cacctatggc    300
atcaccacga gcgtaactc cctgaacctc aagttcgtca ccaagggcca gtactcgacc    360
aacatcggct cgcgtaccta cctgatggag agcgacacca gtaccagag taagttcctc    420 tcgcacccgg ccgccgggag atgatggcgc cagcccgct gacgcgaatg acacagtgtt    480
ccagctcctc ggcaacgagt tcaccttcga tgtcgacgtc tccaacctcg gctgcggcct    540
caatggcgcc ctctacttcg tgtccatgga tgccgatggt ggcatgtcca agtactcggg    600
caacaaggca ggtgccaagt acggtaccgg ctactgtgat tctcagtgcc ccgcgacct    660 caagttcatc aacggcgagg ccaacgtaga gaactggcag agctcgacca acgatgccaa    720
cgccggcacg gcaagtacg gcagctgctg ctccgagatg gacgtctggg aggccaacaa    780
catggccgcc gccttcactc cccaccctg cnccgtgatc ggccagtcgc gctgcgaggg    840
cgactcgtgc ggcggtacct acagcaccga ccgctatgcc ggcatctgcg accccgacgg    900
atgcgacttc aactcgtacc gccagggcaa caagaccttc tacggcaagg gcatgacggt    960
cgacacgacc aagaagatca cggtcgtcac ccagttcctc aagaactcgg ccggcgagct   1020
ctccgagatc aagcggttct acgtccagaa cggcaaggtc atccccaact ccgagtccac   1080
catcccgggc gtcgagggca actccatcac ccaggactgg tgcgaccgcc agaaggccgc   1140
cttcggcgac gtgaccgact ncaggacaa gggcggcatg gtccagatgg caaggccct   1200 cgcggggccc atggtcctcg tcatgtccat ctggacgac cacgccgtca acatgctctg   1260
gctcgactcc acctgcccca tcgacggcgc cggcaagccg ggcgccgagc cggtgcctg   1320 ccccaccacc tcgggcgtcc ccgctgaggt cgaggccgag gccccaact ccaacgtcat   1380
```

-continued

```
cttctccaac atccgcttcg gccccatcgg ctccaccgtc tccggcctgc ccgacggcgg   1440
cagcggcaac cccaacccgc ccgtcagctc gtccaccccg gtcccctcct cgtccaccac   1500
atcctccggt tcctccggcc cgactggcgg cacgggtgtc gctaagcact atgagcaatg   1560
cggaggaatc gggttcactg gccctaccca gtgcgagagc ccctacactt gcaccaagct   1620
gaatgactgg tactcgcagt gcctgtaa                                      1648
```

```

<210> SEQ ID NO 6
<211> LENGTH: 526
<212> TYPE: PRT
<213> ORGANISM: Chrysosporium lucknowense
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (365)..(365)
<223> OTHER INFORMATION: Xaa can be any naturally occurring amino acid

<400> SEQUENCE: 6

Met Tyr Ala Lys Phe Ala Thr Leu Ala Ala Leu Val Ala Gly Ala Ala
1               5                   10                  15

Ala Gln Asn Ala Cys Thr Leu Thr Ala Glu Asn His Pro Ser Leu Thr
            20                  25                  30

Trp Ser Lys Cys Thr Ser Gly Gly Ser Cys Thr Ser Val Gln Gly Ser
        35                  40                  45

Ile Thr Ile Asp Ala Asn Trp Arg Trp Thr His Arg Thr Asp Ser Ala
    50                  55                  60

Thr Asn Cys Tyr Glu Gly Asn Lys Trp Asp Thr Ser Tyr Cys Ser Asp
65                  70                  75                  80

Gly Pro Ser Cys Ala Ser Lys Cys Cys Ile Asp Gly Ala Asp Tyr Ser
                85                  90                  95

Ser Thr Tyr Gly Ile Thr Thr Ser Gly Asn Ser Leu Asn Leu Lys Phe
            100                 105                 110

Val Thr Lys Gly Gln Tyr Ser Thr Asn Ile Gly Ser Arg Thr Tyr Leu
        115                 120                 125

Met Glu Ser Asp Thr Lys Tyr Gln Met Phe Gln Leu Leu Gly Asn Glu
    130                 135                 140

Phe Thr Phe Asp Val Asp Val Ser Asn Leu Gly Cys Gly Leu Asn Gly
145                 150                 155                 160

Ala Leu Tyr Phe Val Ser Met Asp Ala Asp Gly Gly Met Ser Lys Tyr
                165                 170                 175

Ser Gly Asn Lys Ala Gly Ala Lys Tyr Gly Thr Gly Tyr Cys Asp Ser
            180                 185                 190

Gln Cys Pro Arg Asp Leu Lys Phe Ile Asn Gly Glu Ala Asn Val Glu
        195                 200                 205

Asn Trp Gln Ser Ser Thr Asn Asp Ala Asn Ala Gly Thr Gly Lys Tyr
    210                 215                 220

Gly Ser Cys Cys Ser Glu Met Asp Val Trp Glu Ala Asn Asn Met Ala
225                 230                 235                 240

Ala Ala Phe Thr Pro His Pro Cys Xaa Val Ile Gly Gln Ser Arg Cys
                245                 250                 255

Glu Gly Asp Ser Cys Gly Gly Thr Tyr Ser Thr Asp Arg Tyr Ala Gly
            260                 265                 270

Ile Cys Asp Pro Asp Gly Cys Asp Phe Asn Ser Tyr Arg Gln Gly Asn
        275                 280                 285
```

-continued

```
Lys Thr Phe Tyr Gly Lys Gly Met Thr Val Asp Thr Thr Lys Lys Ile
    290                 295                 300

Thr Val Val Thr Gln Phe Leu Lys Asn Ser Ala Gly Glu Leu Ser Glu
305                 310                 315                 320

Ile Lys Arg Phe Tyr Val Gln Asn Gly Lys Val Ile Pro Asn Ser Glu
                325                 330                 335

Ser Thr Ile Pro Gly Val Glu Gly Asn Ser Ile Thr Gln Asp Trp Cys
            340                 345                 350

Asp Arg Gln Lys Ala Ala Phe Gly Asp Val Thr Asp Xaa Gln Asp Lys
        355                 360                 365

Gly Gly Met Val Gln Met Gly Lys Ala Leu Ala Gly Pro Met Val Leu
    370                 375                 380

Val Met Ser Ile Trp Asp Asp His Ala Val Asn Met Leu Trp Leu Asp
385                 390                 395                 400

Ser Thr Trp Pro Ile Asp Gly Ala Gly Lys Pro Gly Ala Glu Arg Gly
                405                 410                 415

Ala Cys Pro Thr Thr Ser Gly Val Pro Ala Glu Val Glu Ala Glu Ala
            420                 425                 430

Pro Asn Ser Asn Val Ile Phe Ser Asn Ile Arg Phe Gly Pro Ile Gly
        435                 440                 445

Ser Thr Val Ser Gly Leu Pro Asp Gly Gly Ser Gly Asn Pro Asn Pro
    450                 455                 460

Pro Val Ser Ser Ser Thr Pro Val Pro Ser Ser Ser Thr Thr Ser Ser
465                 470                 475                 480

Gly Ser Ser Gly Pro Thr Gly Gly Thr Gly Val Ala Lys His Tyr Glu
                485                 490                 495

Gln Cys Gly Gly Ile Gly Phe Thr Gly Pro Thr Gln Cys Glu Ser Pro
            500                 505                 510

Tyr Thr Cys Thr Lys Leu Asn Asp Trp Tyr Ser Gln Cys Leu
        515                 520                 525
```

<210> SEQ ID NO 7
<211> LENGTH: 4376
<212> TYPE: DNA
<213> ORGANISM: Chrysosporium lucknowense
<220> FEATURE:
<221> NAME/KEY: CDS
<222> LOCATION: (2509)..(2950)
<220> FEATURE:
<221> NAME/KEY: CDS
<222> LOCATION: (3061)..(3385)
<220> FEATURE:
<221> NAME/KEY: CDS
<222> LOCATION: (3479)..(3896)

<400> SEQUENCE: 7

```
ggatccacac ctaccatacc ggatagtatg ctacccaagt gacatagggt tggtaaagta      60
atacgagaac tcagagagca ctgcccatat ggctcgccaa tgacctcaag tgccaggtca     120
gctttgcgag acagacctga gcgcgtcgga tgtgtgacat ggaacgcgcc ggatcgcctt     180
gttgattaat tatagggaag tagcgaggaa ggtttcagca attgacgtga gcgtacatta     240
aaagctgtat gatttcagga agacgagcca tggaccaggt ttcaaggctg aatggcttga     300
cgacttaagc accgaacgag gaatgaaaga atgaaaagtg ggggatcatt ctggcccctc     360
ctcgtatgtc gagtgttaaa gaaggcggtt ctacggagga cctaaagagc tccaatttgc     420
tctgttgagc ttaagccaca tatctcaaga tgaatacatg tcaggcatag tcaccctgat     480
```

| | |
|---|---|
| cttgttcatc agtccacaca cttttcagtt cagcatgttg attcctcatc catatcactt | 540 |
| tccattacta tctctttatg tccttggtca agactccaag gaaccgatag gtgagcatcg | 600 |
| gtgaggctcc ctcaaggtac caaagtagcc atcatcaccg aggtctggga atggcgccgt | 660 |
| gcccgatctg agtcctccaa ctccacggta cgacgacagc acgtcacatt gacgcaccac | 720 |
| ggttgaacaa gcagagaggg acacgtcttg ctacgcgaat cctggcactg gatggagacg | 780 |
| cgtgtgagca ggtttccgga accatgacgg cctggtccgg cttctcgaac aaagaagtgg | 840 |
| aacacaaaaa gaaccgaaac ggaaacgcag gcacggcatc gacgaccgga ttgtcccacg | 900 |
| gggacctcgg ccagtcaagc gttgccctgg ccgtcagctc cctggcgacg gggattcagc | 960 |
| acatctcacg ttataggcga cctcatcccc cttccgtctt gtgcggtcgt tgctccgtgc | 1020 |
| cgagtaccca ggcgtgccgg ggcctttagc cggggcggaa tcagagtcaa gatgcggccg | 1080 |
| aattggacgg cagacgaagt ttcgtagagg gtcatgatcg gcactgacga cacccacccc | 1140 |
| tgcgtgatcc cgtggccctg ggctgggaat tgccggctaa taatctacgg cttaatagat | 1200 |
| atgcactttg cacgcggtgc agataaataa gctgtggttt caaacactgg cctccgtact | 1260 |
| ttacccacca actgccgctt agcgccggga cctgagtctt gggagtgcgc ggagcggcag | 1320 |
| ccacctcggg ttagcgtaca cacgacggct gcatgcgggg atgccgcgtg catggcttca | 1380 |
| tagtgtacga cagaccgtca agtccaaatc tgggtgatgc ttgatgagat gacagcgagc | 1440 |
| cccgtcggcg gcaccccggc tatgcatcgc gaattgacaa cactctcagc tctattgcga | 1500 |
| cccatcggat aaaagaagaa gaaaaaaatg gaccttgagt acgggcgtca gaaaccaaaa | 1560 |
| aaaaactccg gaaccaaata tgtcgggcat ggccggggtg aacgaccgct actccccgtt | 1620 |
| cccttcttcg caaacagaac gctacagagg gttttctggt ttgtcaaaga gttcggaggt | 1680 |
| cctctgctcc gcgaatgcgt ggtgaaccca ccagcagcca ttgttcttgc atgcgtggcg | 1740 |
| gaccgttagc cgctgatcga catggcgagc ttcccacctc agacctggag cagacggttg | 1800 |
| cgaggagcaa ggggctgccc tcccctgac ggtcggaccc caatgacttc cccaaacggg | 1860 |
| gacatcgagg gtcgtgcatg atggtggaaa gtagttgcag tatgggaagt accccgggtt | 1920 |
| gccaggaacc gttgttcggc cccccacatt ttctctctgc catgtcaact gtgtgtcgtt | 1980 |
| cgagagttcc tggctccggc ccccgtcca attccctaac gggaccgcgg ggcatcgcct | 2040 |
| gtaactaact tccaaatgaa gccggatatg agggagggag attggatctg caagccagc | 2100 |
| cattcgctgc gatcggcact cgtccgtcag ccccgcagtc catatcccca aaggcaactg | 2160 |
| ctcggcgcgg ctcaagtctt cttcggaacg tccagcccga aggcgcgcgc cagcaccggc | 2220 |
| cctatgttcc tgattgcgat cctcgatctc cagagacggg tcacctcgcc tcgaggacgg | 2280 |
| tgcaggggca tcggcttcgc ttcctagagc tccgggctgt gtgtggtcaa ggggagaagg | 2340 |
| cggcggcgcc aaggtgcgtc tcggcgcact cacccatcgc ctttaccccc ctcccccca | 2400 |
| gtatataaaa gatggccatc gtctcctcgt ctgcttggga agaaaggatc tctcgaccat | 2460 |
| gcaccacagc ctagctctaa cccagcttgt cgtgtgttgt tgcccagc atg aag ttc | 2517 |
|                                                                                                                                                     Met Lys Phe<br>                                                                                                                                                     1 | |
| gtg cag tcc gcc acc ctg gcg ttc gcc gcc acg gcc ctc gct gcg ccc<br>Val Gln Ser Ala Thr Leu Ala Phe Ala Ala Thr Ala Leu Ala Ala Pro<br>     5                      10                      15 | 2565 |
| tcg cgc acg act ccc cag aag ccc cgc cag gcc tcg gcg ggc tgc gcg<br>Ser Arg Thr Thr Pro Gln Lys Pro Arg Gln Ala Ser Ala Gly Cys Ala<br>20                     25                      30                      35 | 2613 |
| tcg gcc gtg acg ctc gat gcc agc acc aac gtg ttc cag cag tac acg | 2661 |

```
                                                   -continued

Ser Ala Val Thr Leu Asp Ala Ser Thr Asn Val Phe Gln Gln Tyr Thr
            40                  45                  50 ctg cac ccc aac aac ttc tac cgt gcc gag gtc gag gct gcc gcc gag    2709
Leu His Pro Asn Asn Phe Tyr Arg Ala Glu Val Glu Ala Ala Ala Glu
                55                  60                  65 gcc atc tcc gac tcg gcg ctg gcc gag aag gcc cgc aag gtc gcc gac    2757
Ala Ile Ser Asp Ser Ala Leu Ala Glu Lys Ala Arg Lys Val Ala Asp
                70                  75                  80 gtc ggt acc ttc ctg tgg ctc gac acc atc gag aac att ggc cgg ctg    2805
Val Gly Thr Phe Leu Trp Leu Asp Thr Ile Glu Asn Ile Gly Arg Leu
            85                  90                  95 gag ccc gcg ctc gag gac gtg ccc tgc gag aac atc gtg ggt ctc gtc    2853
Glu Pro Ala Leu Glu Asp Val Pro Cys Glu Asn Ile Val Gly Leu Val
100                 105                 110                 115 atc tac gac ctc ccg ggc cgt gac tgc gcg gcc aag gcc tcc aac ggc    2901
Ile Tyr Asp Leu Pro Gly Arg Asp Cys Ala Ala Lys Ala Ser Asn Gly
                120                 125                 130 gag ctc aag gtc ggc gag ctc gac agg tac aag acc gag tac atc gac a  2950
Glu Leu Lys Val Gly Glu Leu Asp Arg Tyr Lys Thr Glu Tyr Ile Asp
            135                 140                 145 gtgagttaac cctttgtggc cccttctttt cccccgagag agcgtctggt tgagtggggt   3010
tgtgagagag aaaatggggc gagcttaaag actgacgtgt tggctcgcag ag atc       3065
                                                         Lys Ile gcc gag atc ctc aag gcc cac tcc aac acg gcc ttc gcc ctc gtc atc    3113
Ala Glu Ile Leu Lys Ala His Ser Asn Thr Ala Phe Ala Leu Val Ile
150                 155                 160                 165 gag ccc gac tcg ctc ccc aac ctg gtc acc aat agc gac ctg cag acg    3161
Glu Pro Asp Ser Leu Pro Asn Leu Val Thr Asn Ser Asp Leu Gln Thr
                170                 175                 180 tgc cag cag agc gct tcc ggc tac cgc gag ggt gtc gcc tat gcc ctc    3209
Cys Gln Gln Ser Ala Ser Gly Tyr Arg Glu Gly Val Ala Tyr Ala Leu
            185                 190                 195 aag cag ctc aac ctc ccc aac gtg gtc atg tac atc gat gcc ggc cac    3257
Lys Gln Leu Asn Leu Pro Asn Val Val Met Tyr Ile Asp Ala Gly His
                200                 205                 210 ggt ggc tgg ctc ggc tgg gac gcc aac ctc aag ccc ggc gcc cag gag    3305
Gly Gly Trp Leu Gly Trp Asp Ala Asn Leu Lys Pro Gly Ala Gln Glu
215                 220                 225 ctc gcc agc gtc tac aag tct gct ggt tcg ccc tcg caa gtc cgc ggt    3353
Leu Ala Ser Val Tyr Lys Ser Ala Gly Ser Pro Ser Gln Val Arg Gly
230                 235                 240                 245 atc tcc acc aac gtg gct ggt tgg aac gcc tg gtaagacact ctatgtcccc    3405
Ile Ser Thr Asn Val Ala Gly Trp Asn Ala Trp
                250                 255 ctcgtcggtc aatggcgagc ggaatggcgt gaaatgcatg gtgctgacct ttgatctttt   3465 cccccctccta tag g gac cag gag ccc ggt gag ttc tcg gac gcc tcg gat  3515
                 Asp Gln Glu Pro Gly Glu Phe Ser Asp Ala Ser Asp
                                 260                 265 gcc cag tac aac aag tgc cag aac gag aag atc tac atc aac acc ttt    3563
Ala Gln Tyr Asn Lys Cys Gln Asn Glu Lys Ile Tyr Ile Asn Thr Phe
        270                 275                 280 ggc gct gag ctc aag tct gcc ggc atg ccc aac cac gcc atc atc gac    3611
Gly Ala Glu Leu Lys Ser Ala Gly Met Pro Asn His Ala Ile Ile Asp
285                 290                 295                 300 act ggc cgc aac ggt gtc acc ggt ctc cgc gac gag tgg ggt gac tgg    3659
Thr Gly Arg Asn Gly Val Thr Gly Leu Arg Asp Glu Trp Gly Asp Trp
                305                 310                 315 tgc aac gtc aac ggc gcc ggc ttc ggt gtg cgc ccg act gcc aac act    3707
```

-continued

```
Cys Asn Val Asn Gly Ala Gly Phe Gly Val Arg Pro Thr Ala Asn Thr
            320                 325                 330 ggc gac gag ctc gcc gac gcc ttc gtg tgg gtc aag ccc ggt ggc gag     3755
Gly Asp Glu Leu Ala Asp Ala Phe Val Trp Val Lys Pro Gly Gly Glu
        335                 340                 345 tcc gac ggc acc agc gac tcg tcg gcg gcg cgc tac gac agc ttc tgc     3803
Ser Asp Gly Thr Ser Asp Ser Ser Ala Ala Arg Tyr Asp Ser Phe Cys
    350                 355                 360 ggc aag ccc gac gcc ttc aag ccc agc ccc gag gcc ggt acc tgg aac     3851
Gly Lys Pro Asp Ala Phe Lys Pro Ser Pro Glu Ala Gly Thr Trp Asn
365                 370                 375                 380 cag gcc tac ttc gag atg ctc ctc aag aac gcc aac ccg tcc ttc         3896
Gln Ala Tyr Phe Glu Met Leu Leu Lys Asn Ala Asn Pro Ser Phe
                385                 390                 395 taagctcctc gacggcttct tgctgtcagt cgctctgacg gtggtgtgct ggtggtgccc   3956
ctgctcctgc tgctgctgct ccgcggggag gggaggcaac gaaaatgaag tcctgcttca   4016
aaacaaaaca gaaacaagcg aggcgcggtg caatggtcgt gcgttcgtct tttttcatgt   4076
tcccttctag tgtagtagtt tgatagtcgt acataagggg tttcagaacc gtctctctgt   4136
ctcggtcttt ttgcgagttg ttgcgactcg tgattatggc ctttgttgct cgttgcggca   4196
gagtagaacc acagcgtgtt ggggtagcag cttgctccgt aggacgtagg gaaacaacct   4256
gagactctgg aattgcagtc agcctgcgtc gcccctctag gaaacgaagg ggagaaccag   4316
tagtggctgc agcttacaaa cgcgagcatg gtgaacatct ccgagaaaag ggagggatcc   4376

<210> SEQ ID NO 8
<211> LENGTH: 395
<212> TYPE: PRT
<213> ORGANISM: Chrysosporium lucknowense

<400> SEQUENCE: 8

Met Lys Phe Val Gln Ser Ala Thr Leu Ala Phe Ala Ala Thr Ala Leu
1               5                   10                  15

Ala Ala Pro Ser Arg Thr Thr Pro Gln Lys Pro Arg Gln Ala Ser Ala
            20                  25                  30

Gly Cys Ala Ser Ala Val Thr Leu Asp Ala Ser Thr Asn Val Phe Gln
        35                  40                  45

Gln Tyr Thr Leu His Pro Asn Asn Phe Tyr Arg Ala Glu Val Glu Ala
    50                  55                  60

Ala Ala Glu Ala Ile Ser Asp Ser Ala Leu Ala Glu Lys Ala Arg Lys
65                  70                  75                  80

Val Ala Asp Val Gly Thr Phe Leu Trp Leu Asp Thr Ile Glu Asn Ile
                85                  90                  95

Gly Arg Leu Glu Pro Ala Leu Glu Asp Val Pro Cys Glu Asn Ile Val
            100                 105                 110

Gly Leu Val Ile Tyr Asp Leu Pro Gly Arg Asp Cys Ala Ala Lys Ala
        115                 120                 125

Ser Asn Gly Glu Leu Lys Val Gly Glu Leu Asp Arg Tyr Lys Thr Glu
    130                 135                 140

Tyr Ile Asp Lys Ile Ala Glu Ile Leu Lys Ala His Ser Asn Thr Ala
145                 150                 155                 160

Phe Ala Leu Val Ile Glu Pro Asp Ser Leu Pro Asn Leu Val Thr Asn
                165                 170                 175

Ser Asp Leu Gln Thr Cys Gln Gln Ser Ala Ser Gly Tyr Arg Glu Gly
            180                 185                 190
```

-continued

```
Val Ala Tyr Ala Leu Lys Gln Leu Asn Leu Pro Asn Val Val Met Tyr
        195                 200                 205

Ile Asp Ala Gly His Gly Gly Trp Leu Gly Trp Asp Ala Asn Leu Lys
    210                 215                 220

Pro Gly Ala Gln Glu Leu Ala Ser Val Tyr Lys Ser Ala Gly Ser Pro
225                 230                 235                 240

Ser Gln Val Arg Gly Ile Ser Thr Asn Val Ala Gly Trp Asn Ala Trp
                245                 250                 255

Asp Gln Glu Pro Gly Glu Phe Ser Asp Ala Ser Asp Ala Gln Tyr Asn
            260                 265                 270

Lys Cys Gln Asn Glu Lys Ile Tyr Ile Asn Thr Phe Gly Ala Glu Leu
        275                 280                 285

Lys Ser Ala Gly Met Pro Asn His Ala Ile Ile Asp Thr Gly Arg Asn
    290                 295                 300

Gly Val Thr Gly Leu Arg Asp Glu Trp Gly Asp Trp Cys Asn Val Asn
305                 310                 315                 320

Gly Ala Gly Phe Gly Val Arg Pro Thr Ala Asn Thr Gly Asp Glu Leu
                325                 330                 335

Ala Asp Ala Phe Val Trp Val Lys Pro Gly Gly Glu Ser Asp Gly Thr
            340                 345                 350

Ser Asp Ser Ser Ala Ala Arg Tyr Asp Ser Phe Cys Gly Lys Pro Asp
        355                 360                 365

Ala Phe Lys Pro Ser Pro Glu Ala Gly Thr Trp Asn Gln Ala Tyr Phe
    370                 375                 380

Glu Met Leu Leu Lys Asn Ala Asn Pro Ser Phe
385                 390                 395
```

<210> SEQ ID NO 9
<211> LENGTH: 5777
<212> TYPE: DNA
<213> ORGANISM: Chrysosporium lucknowense

<400> SEQUENCE: 9

```
tgctgctctg atgtgctgat gcacagcttc ccctcgcgat tgccggcagg atctccaacc      60
ctctggatcg gagcagacga tcagcgggca caatggccag cttgccagcg ttcaactcca     120
agttgacccg cttttatcac gcccaagctg gacatgcaca ggcttggctt ctcgtgttcc     180
tacgatctgc acagtaggtt tgactgctga tcttcgcttt cctgtgcgcc ctccccctcc     240
ctcacgggta ccttatcctt gcctgtaacc ccgcgttatg tcaaacttga gtttgaccaa     300
tgctagcgca aaagtaccta catagtacta tgtaataagg taggtacata catcagtagg     360
cgtttatcta gtaaattttg gctttttgaa actcaattgc tcctctcctc gcctccacct     420
ctgcttggca attgacaacc ctggctgtgc ctagaggtag catcgacgat caatcaaatc     480
taaagtattc gagattgacc tttctgctct aattatatta attatccgca caatgctgta     540
gtcattgact ctcctttcaa gttgccttct cgtttatgta tgtacaatgg gcggtcatgc     600
ttcatgccaa cagatggttc tatcggaaca atgtttgact ttctggtcgc cccgtcgaac     660
tgttttgatt tcgcacggga agtgttctta ccaaagctaa gtcgactcgt ggagcttcgt     720
aacggccagt gatcgttgat cgcttttgga ggagttgcga tggagcgaga ccggctacga     780
gcacgttcgc aaaggcagca cgatagacga ccctccgtgg cgccattcgg gagatgcaca     840
tgacataagc atatcaatac tcacctgaac tcatcggccg atgcctcgca ggtagttaca     900
agacatattt gtgtgggtat attatcccaa cccgtacctt tgtcgcgtca tttcggtatg     960
```

```
tgctgatgcc tacttaggga gcaaagacgc ctctcctcac ctgcgggtta cttacttact    1020
gtgcagcatg gccttatgtt ctcccgggtc ttgcttgcgc gaatgaacaa aaacgcccga    1080
agaaaagccg cttcttcgag ttgtgtctac ccgaacataa gaggttattg tcgcagaccg    1140
ccagcaaatg tcaacaaccc acccacggcg ttccagaacc ttcgaaatat catctagttt    1200
aagtttaaat gacggcccga gtcccagccg agattcccat attggccgat accagcgttc    1260
ccttgttttt ccaaggttgt ctcgtcaact ggcgcatctg cctacaacga gatataatta    1320
ccgttttctt ttgcaaaagg gcatgcatgg atgtatatta tttatgcctg cagaacgaga    1380
agcaatcatg gtgtaggttt tgtgcggtat ggagctaata atattgaacg gatctctggt    1440
ccgtcctaaa tcgttgaaac gctaggccca ggaggacctg ctcgacttgg cgaacggaga    1500
tttccaggat gaaggtcgg aacatgtcca tccgcggcca gcctgaacac ttttgctcgt    1560
ttccggacca tcgacccacg aaaacagtgc ggttgctggc acagtcagca ctcacgatgg    1620
cgatggtcca gcccgttccc gcccgatgcc cacttgcagc gcaactctcc ttcattcggc    1680
ggcccggcgg tgtctggcct attagtacga ttttggatac cggcttggtc gccgcgcgg     1740
tttttcttgg ccgatacggg aatctcggtg gtcccaactc cacctgggca cgctctggtg    1800
ccaacatgga acttcgggat gccgctccgg gcacagtcaa gcgctttaaa atacgacttt    1860
accccacaag aatcgaggcg taaccccgaa ttagggacac ctggacggcg caaccctgg     1920
accgaagggc ctcgctaacc gggttcctgg agccgcatgc gcggctgccc gcttgccgc     1980
tcttgagatg acacttcttt tcagcgaggg atggtcgggc agggaaatga tgtattataa    2040
gaagcgagcc gattccgaag gactcgaccc cctctctcgc cctgtgtccg ccagctaatt    2100
acagcactcc ttctcgactt gaaacgcccg agatgaagtc ctccatcctc gccagcgtct    2160
tcgccacggg cgccgtggct caaagtggtc cgtggcagca atgtggtggc atcggatggc    2220
aaggatcgac cgactgtgtg tcgggttacc actgcgtcta ccagaatgat tggtacagcc    2280
agtgcgtgcc tggcgcggcg tcgacaacgc tccagacatc taccacgtcc aggcccaccg    2340
ccaccagcac cgcccctccg tcgtccacca cctcgcctag caagggcaag ctcaagtggc    2400
tcggcagcaa cgagtcgggc gccgagttcg gggagggcaa ctaccccggc ctctggggaa    2460
agcacttcat cttcccgtcg acttcggcga ttcaggtacg ggccaataat aatatattat    2520
tatagcaggc aggagggagc aggagaagaa gggaggggca ggtggccaac aatcggaaga    2580
agaccgggag gcactgaccg ttgattcctt tgtgtaatag acgctcatca atgatggata    2640
caacatcttc cggatcgact tctcgatgga gcgtctggtg cccaaccagt tgacgtcgtc    2700
cttcgacgag ggctacctcc gcaacctgac cgaggtggtc aacttcgtga cgaacgcggg    2760
caagtacgcc gtcctggacc cgcacaacta cggccggtac tacggcaacg tcatcacgga    2820
cacgaacgcg ttccggacct tctggaccaa cctggccaag cagttcgcct ccaactcgct    2880
cgtcatcttc gacaccaaca acgagtacaa cacgatggac cagaccctgg tgctcaacct    2940
caaccaggcc gccatcgacg gcatccgggc cgccggcgcg acctcgcagt acatcttcgt    3000
cgagggcaac gcgtggagcg gggcctggag ctggaacacg accaacacca acatggccgc    3060
cctgacggac ccgcagaaca agatcgtgta cgagatgcac cagtacctcg actcggacag    3120
ctcgggcacc cacgccgagt gcgtcagcag caacatcggc gcccagcgcg tcgtcggagc    3180
cacccagtgg ctccgcgcca acggcaagct cggcgtcctc ggcgagttcg ccggcggcgc    3240
caacgccgtc tgccagcagg ccgtcaccgg cctcctcgac cacctccagg acaacagcga    3300
ggtctggctg ggtgccctct ggtgggccgc cggtccctgg tggggcgact acatgtactc    3360
```

```
gttcggtaag tttctccctt gttcttggct ttcccccccag taaggagtc aggcaacatg    3420
cccaagaccg gctcggcttc gcttcaaggc gttcgttgta cacactgaag agttccaact    3480
tccaaccctg ttcgtgtcct ccgatcagct tcgacggggt gaaggggggaa gggatttggg   3540
agtgaggtgg aggtcaaaag gagggatatc cccagatctc cacaaacggc cctgagccaa    3600
caacagcctc tggggtcaaa atgggcgcca accatacggt cattcactca ggacacctgc    3660
taacgcgtct cttttttttg tttccagagc ctccttcggg caccggctat gtcaactaca    3720
actcgatcct aaagaagtac ttgccgtaag gggcatgcag caaggtcgag cgagcattat    3780
tcagggccat ctgcttgtgt cggcaggcat cacgtcaacc catcgaatcg gacagcggaa    3840
tgctccgaga tgccatacac taagtctggt gatgacgtga aatgctggc cctggtcggg     3900
ggttaccgcc aacaaaaagc acccggacg tgccgcgccc ggataccatg gtttcatgta    3960
catattggtt ctttgctttc ttacgggggg gggggggggg gggggctctg cagcgttgct    4020
gagcgattcg tttccaagta tatactttgt ctggaattga attttgagtg acattgaccc    4080
aatcaaccag ctcggtgtgc tcacctcccg ttaccccccc tcttctcccc ctgctcggct    4140
tggctttcct ctccggtgtg gagcacggcc acggcggtcc caatccatat aagatcgatg    4200
gtatactatg gtatacacta gcttgggaat aaactaatcc atacgctaac taatggacgg    4260
attatcctaa gggtcaccgg ctcaccgttg gatataacac ctaggatacg ggagagctga    4320
tagaaaggga tgtactccgt attgtactgt acaatacaaa gtacagatag cacacgaagt    4380
acggtaggtg gtcccgccta gtccggacca acaatagaac atgcgttcct ggggacctgc    4440
aggaaagaag gggggggggg ttgccaagac gcccggggtt caaagaaagc cccgggccgc    4500
cgatgagatg agacggacgc cggcccaagg agaggccggt ggtcgatcct gcaaatgcca    4560
gcaaaaaaaa tccataccat aatccagtca actttcgtca cactcctgtg aaacgagctg    4620
gagggactgc tggaaaggtt ttgcaggtta atcactgtat gtggagcatg ccgtacctac    4680
tgtgcttcgt taacagatag agttccagtt gaacacacaa agttctgccc cgcctgccag    4740
acgtgaaaag aagctcctcc gggggagctt taggcaactg ggagggctct ctcccaggtt    4800
catggtgtct gctcttcttc aaatttttat gctgccaccc catttgacag aggtgtgcac    4860
accgttgcca ggtcttgcca tccggcaaaa agcagaaaag tcgacccatc gcctaagaaa    4920
ggcggtcgga aggggatcgg atgctcattg cggcttagcg tctgcccatt ctgacgctgc    4980
ccattgtttt gtgtcgcatt cgtcttcgga tgtcggatca agagtcccgg attttttccc    5040
ctgtgcttcc agcctaatct gagcgggagc tggctcggtt tcgagtggag ttgccttgtt    5100
ggtggagcag caaccagcca attcactccc ccgcattttc gcggccgccc aggcatcccc    5160
ggcatgcgtt tgggcggtaa ctactccgta ctggggtagg tgaaattggt tctcccgtcg    5220
caggaggctc gtgctcggtc aggggagaac aaagtccaac tgctccttcc tggcaacaat    5280
gagaggggggt tctattgcca acgttgcacg aaaggagcag ccacaaaacc caaaagcagg    5340
ttaccttact gtacctgagc ttgaacgtcg cgtagcattg gagctctcgt ctaccggcgg    5400
cgtcacactc cattggcagg tcaaggcagt cagtggcagc gacccaacaa cgtcaatgct    5460
tgttacccca gaattacccc gggctgcaac actgcagggg ccgccgccga tgttgatcac    5520
cggttgatta cttctcggcc cgcaaccggg agatgagaag cagaactttg ttctccttc    5580
aaaaaggacc tgacttgcgg ggaacgcact gccggcagtg gagtggatgc acgctagtta    5640
tatgtttccc gccatcccca gtccgcccgt cgcgtccgtg aggctcagtt tggcttcccg    5700
```

-continued tgccgccgac aaacgagcgg tgcataatta catttcgctc catgtaccgt gcaccctccc 5760
cgttcgcgac cgtagta 5777

<210> SEQ ID NO 10
<211> LENGTH: 389
<212> TYPE: PRT
<213> ORGANISM: Chrysosporium lucknowense

<400> SEQUENCE: 10

Met Lys Ser Ser Ile Leu Ala Ser Val Phe Ala Thr Gly Ala Val Ala
1 5 10 15

Gln Ser Gly Pro Trp Gln Gln Cys Gly Gly Ile Gly Trp Gln Gly Ser
20 25 30

Thr Asp Cys Val Ser Gly Tyr His Cys Val Tyr Gln Asn Asp Trp Tyr
35 40 45

Ser Gln Cys Val Pro Gly Ala Ala Ser Thr Thr Leu Gln Thr Ser Thr
50 55 60

Thr Ser Arg Pro Thr Ala Thr Ser Thr Ala Pro Pro Ser Ser Thr Thr
65 70 75 80

Ser Pro Ser Lys Gly Lys Leu Lys Trp Leu Gly Ser Asn Glu Ser Gly
85 90 95

Ala Glu Phe Gly Glu Gly Asn Tyr Pro Gly Leu Trp Gly Lys His Phe
100 105 110

Ile Phe Pro Ser Thr Ser Ala Ile Gln Thr Leu Ile Asn Asp Gly Tyr
115 120 125

Asn Ile Phe Arg Ile Asp Phe Ser Met Glu Arg Leu Val Pro Asn Gln
130 135 140

Leu Thr Ser Ser Phe Asp Glu Gly Tyr Leu Arg Asn Leu Thr Glu Val
145 150 155 160

Val Asn Phe Val Thr Asn Ala Gly Lys Tyr Ala Val Leu Asp Pro His
165 170 175

Asn Tyr Gly Arg Tyr Tyr Gly Asn Val Ile Thr Asp Thr Asn Ala Phe
180 185 190

Arg Thr Phe Trp Thr Asn Leu Ala Lys Gln Phe Ala Ser Asn Ser Leu
195 200 205

Val Ile Phe Asp Thr Asn Asn Glu Tyr Asn Thr Met Asp Gln Thr Leu
210 215 220

Val Leu Asn Leu Asn Gln Ala Ala Ile Asp Gly Ile Arg Ala Ala Gly
225 230 235 240

Ala Thr Ser Gln Tyr Ile Phe Val Glu Gly Asn Ala Trp Ser Gly Ala
245 250 255

Trp Ser Trp Asn Thr Thr Asn Thr Asn Met Ala Ala Leu Thr Asp Pro
260 265 270

Gln Asn Lys Ile Val Tyr Glu Met His Gln Tyr Leu Asp Ser Asp Ser
275 280 285

Ser Gly Thr His Ala Glu Cys Val Ser Ser Asn Ile Gly Ala Gln Arg
290 295 300

Val Val Gly Ala Thr Gln Trp Leu Arg Ala Asn Gly Lys Leu Gly Val
305 310 315 320

Leu Gly Glu Phe Ala Gly Gly Ala Asn Ala Val Cys Gln Gln Ala Val
325 330 335

Thr Gly Leu Leu Asp His Leu Gln Asp Asn Ser Glu Val Trp Leu Gly
340 345 350

Ala Leu Trp Trp Ala Ala Gly Pro Trp Trp Gly Asp Tyr Met Tyr Ser

```
                355                 360                 365
Phe Glu Pro Pro Ser Gly Thr Gly Tyr Val Asn Tyr Asn Ser Ile Leu
    370                 375                 380
Lys Lys Tyr Leu Pro
385

<210> SEQ ID NO 11
<211> LENGTH: 6060
<212> TYPE: DNA
<213> ORGANISM: Chrysosporium lucknowense

<400> SEQUENCE: 11
ccggcctcca gttccaggag cttggctctg ccgacatact gtgtacacta ggaattctct      60 tatgcgggt  gtgcgcgggg aaatgttggg gaactcgagt tgggtcatgt ggacaagacc     120
aatgggagct gacatcattg tgcgacccgt taaaccggaa gctacaacaa cattctggat     180
tctacactag tggaagaggt aagtaattga cgacaagcaa gaagcattgc catgttctgc     240
gaaggatgcg ggtgtttttg catgagcagg aagctgtggc tttttagtgc tcctttgtgc     300
tcgccgggcg cgcagaacac taccgaaacg caggggactg cgtgcctctg ggtcgaatg     360 ccgatcccca tcttcacatt cccaccatcg tgttctgtta acgaagccgg agcggcggga     420
actcgaagct ccactacgta tggatacttg ggaccgtacg gagtgtgttg gtacggatgc     480
ctgcacaagt gttgtgcttc ctacgaagac gccaacccac ataatacaca aaagctgttg     540
taagtcgagt tacctcaggc acgttcgggc aactcgggca acctgacgag atttccccgc     600
cattccgcca agaggccggc gcctgccctg attaggcagc tcttggaaca atactatgta     660
gaatggaagc tccatccata gtcagctcca ttggcggtcc cagtgatctc gatggctgga     720
tggctgctct gtacggtaca tacatagtaa gttctcgcct tgagagccca attcgctgca     780
atagcatctt tcccgcagt  gcgccggccg ccctgggtcc cgctccacaa tgaccttgct     840
tctggagctt ctcgacgaac agatcggccc gtttcttctc cacaccaatc cgaaccagtc     900
gggagcatgg ctgcggatgc gacgcagcct tccttcgcgc tgtacaaaca gctccgggaa     960
cgtcgactgg tatgtacgga ctacagtaag tacactacga gtgcacatac tgacgaatac    1020
cggcctcaga ggaacctggc aggaccctac cccacacgaa accacagcga gaaagcgcaa    1080
tggatcagta actactgcga agtaaccgtg gtcccgggca aaggatctga ggccgatcg     1140 ctcgtggggc tgcgaggcga gggagagcaa acaagccagt cctcccgcga acctggaaaa    1200
tcacttataa acacacgtca ccggcgccgg ggtgcgcgcc atgtgtcacc tccaggctcc    1260 tccccgggcga tgatctctgc cggtgccatc aatcatctcg gttcgccgca gctgcttctt    1320
tctgtgcagt gaacgctctc aaactgcaac gacgctgtcc gacatgaagg ctgctgcgct    1380
ttcctgcctc ttcggcagta cccttgccgt tgcaggcgcc attgaatcga gaaaggtatg    1440
gacgggcttt cgtcaaagac tcgctccccg atcaacttcc cctttcatcc agaccacccc    1500
aaccctccca gtcctgcttc gagcacgatc tcttcgggca gcaccccacc cacatccact    1560
cagattagcg gcgacaccgt tgactgttgc aatccgcaat cgacatgcaa cttccagccg    1620
cagcccaatg gctgctcacg cttcccgcga aagcctcact tgctgacaat catcgtcagg    1680
ttcaccagaa gcccctcgcg agatctgaac cttttttaccc gtcgccatgg atgaatccca    1740
acgccgacgg ctgggcggag gcctatgccc aggccaagtc ctttgtctcc caaatgactc    1800
tgctagagaa ggtcaacttg accacgggag tcgggtaagt tttgtcattt tgtccaggta    1860
acatgcaaat ggttctgcta acaataactt accgtagctg gggggctgag cagtgcgtcg    1920
```

```
gccaagtggg cgcgatccct cgccttggac ttcgcagtct gtgcatgcat gactcccctc   1980
tcggcatccg aggagccgac tacaactcag cgttcccctc tggccagacc gttgctgcta   2040
cctgggatcg cggtctgatg taccgtcgcg gctacgcaat gggccaggag gccaaaggca   2100
agggcatcaa tgtccttctc ggaccagtcg ccggcccccct tggccgcatg cccgagggcg   2160
gtcgtaactg ggaaggcttc gctccggatc ccgtccttac cggcatcggc atgtccgaga   2220
cgatcaaggg cattcaggat gctggcgtca tcgcttgtgc gaagcacttt attggaaacg   2280
agcagggtga gtagtcaaag acgggccgtc tcggacccgc ggcttcaagc tgctgactct   2340
gctgcagagc acttcagaca ggtgccagaa gcccagggat acggttacaa catcagcgaa   2400
accctctcct ccaacattga cgacaagacc atgcacgagc tctacctttg gccgtttgcc   2460
gatgccgtcc gggccggcgt cggctctgtc atgtgctcgt accagcaggt caacaactcg   2520
tacgcctgcc agaactcgaa gctgctgaac gacctcctca agaacgagct ggggtttcag   2580
ggcttcgtca tgagcgactg gcaggcacag cacactggcg cagcaagcgc cgtggctggt   2640
ctcgatatgt ccatgccggg cgacacccag ttcaacactg gcgtcagttt ctggggcgcc   2700
aatctcaccc tcgccgtcct caacggcaca gtccctgcct accgtctcga cgacatggcc   2760
atgcgcatca tggccgccct cttcaaggtc accaagacca cccacctgga acccatcaac   2820
ttctccttct ggaccgacga cacttatggc ccgatccact gggccgccaa gcatggctac   2880
cagaagatta attcccacgt tgacgtccgc gccgaccacg gcaacctcat ccgggagatt   2940
gccgccaagg gtacggtgct gctgaagaat accggctctc tacccctgaa caagccaaag   3000
ttcgtggccg tcatcggcga ggatgctggg tcgagcccca acgggcccaa cggctgcagc   3060
gaccgcggct gtaacgaagg cacgctcgcc atgggctggg gatccggcac agccaactat   3120
ccgtacctcg tttccccga cgccgcgctc caggcccggg ccatccagga cggcacgagg   3180
tacgagagcg tcctgtccaa ctacgccgag gaaaagacaa aggctctggt ctcgcaggcc   3240
aatgcaaccg ccatcgtctt cgtcaatgcc gactcaggcg agggctacat caacgtggac   3300
ggtaacgagg gcgaccgtaa gaacctgact ctctggaaca acggtgatac tctggtcaag   3360
aacgtctcga gctggtgcag caacaccatc gtcgtcatcc actcggtcgg cccggtcctc   3420
ctgaccgatt ggtacgacaa ccccaacatc acggccattc tctgggctgg tcttccgggc   3480
caggagtcgg gcaactccat caccgacgtg ctttacggca aggtcaaccc cgccgcccgc   3540
tcgcccttca cttggggcaa gacccgcgaa agctatggcg cggacgtcct gtacaagccg   3600
aataatggca atggtgcgcc ccaacaggac ttcaccgagg gcgtcttcat cgactaccgc   3660
tacttcgaca aggttgacga tgactcggtc atctacgagt tcggccacgg cctgagctac   3720
accaccttcg agtacagcaa catccgcgtc gtcaagtcca acgtcagcga gtaccggccc   3780
acgacgggca ccacggccca ggccccgacg tttggcaact ctccaccga cctcgaggac   3840 tatctcttcc ccaaggacga gttccctac atctaccagt acatctaccc gtacctcaac   3900
acgaccgacc cccggagggc ctcggccgat ccccactacg gccagaccgc cgaggagttc   3960
ctcccgcccc acgccaccga tgacgacccc cagccgctcc tccggtcctc gggcggaaac   4020
tcccccggcg gcaaccgcca gctgtacgac attgtctaca caatcacggc cgacatcacg   4080
aatacgggct ccgttgtagg cgaggaggta ccgcagctct acgtctcgct gggcggtccc   4140
gaggatccca aggtgcagct gcgcgacttt gacaggatgc ggatcgaacc cggcgagacg   4200
aggcagttca ccggccgcct gacgcgcaga gatctgagca actgggacgt cacggtgcag   4260
```

```
gactgggtca tcagcaggta tcccaagacg gcatatgttg ggaggagcag ccggaagttg    4320
gatctcaaga ttgagcttcc ttgaatgagt ttcatcaggg gctgcagagg gatggtaaca    4380
cgttcttaat cagaagtatg atggagaaaa gcacttggca agttccggtg agcaaaaaga    4440
aggcacttat taagtgtagg gcggtgttct atgtttaata ggtgctatgt ttacatataa    4500
ttagtatata atgatttaat aattatgttt agcagttgct aatgtcgtaa atttcggcgt    4560
gtgatgactg ctacaacact ggttctgtct tctagtcgcc attgttaatt atgaaggtta    4620
ttgtctacaa tttctaatac cttatggatg attgcccagc tggtttcaaa ctcgttacgc    4680
gcaaatggta cgattgaggt attattcatt gtaagtacct ccgtacagcg tccccaacta    4740
tttccattca cgagatgcct cgcttttcgg tgctttcgga acagggctgg cagcggatca    4800
tggcgcgatc aaaacatggc gagcagctgt ccaggacgga ggacaggttg gggactgatg    4860
cctcccggac gcattaaggt cagaagatag acacgtttta cacagcgttg agaccgacaa    4920
gccacattag gcagcgccgg ttgcaccacc gccgtcacgg gcaacggttc aatcaatcga    4980
caacagtgga agacaaagta ctgaagatca ggtattaata gtgtgagaga gaaacagacg    5040
gtggaactag ggtgctaata tttctcttga tttcggtgtc catggtagta cagaacacaa    5100
gaaaagaag gaggagtgag cggagaagga ggaggggggaa gccagaaaaa agaacatgaa    5160
aaagcataca cattggagtc ggtcagtcgg ttgattggtt tggtagagag cgaaaaagca    5220
agcgtcacct gtaggattcg aacctacgct cccgaaggaa ctgcctaaga acgctaagca    5280
aggttagcag ggcagcgcgt taaccactcc gccaaagtga ctgtcgttga tcatggtcga    5340
attcaagtag cttataggag ttcaaccaga tcacaaatgc ataggtgctc gtagaacggt    5400
ctaagtatga gttgattata agcaaccgaa tggctctcag cggcaacacc gtagctgaag    5460
taacaaaacg cacctttggt tactttctga ctataaaaat gggatatttg gaaatgacca    5520
cccgataagg tgtcaaattc taaatgactg tctgggtgtg aagatgttac tgtggttcca    5580
ccacgaacca gttttagtat ccgcatgctt cagtctctgc gcctcgacag gcggagggtg    5640
tgtgttagat cagaatcgat gtgacgctgt gaccgcgagg ctctcgagcc taggtgcggt    5700
agttctgttc aaaaagaagt gtgtggccgg gtttgggcgc ccttatagcc taccatcctg    5760
gctgtggttc ccgagcggga gccggttctc cgttttggtt ccgataaagt gtcatatctg    5820
cctcccggtt tcgcatctaa tttctgactt cgttcgggac ctctggagac gtagggatag    5880
gtatgggata tgcccggcat ttcgtaaatg tccatagtct ctttcgggac gaggcggcaa    5940
gctctcagag ctatctaagc ttaaccaacc cctgatcctt aaccctccca gaccacacct    6000
cctgggagaa taaaccgggc tccaagatcg aaatcgaaat cagtgcgcga acttgaaatc    6060
```

<210> SEQ ID NO 12
<211> LENGTH: 871
<212> TYPE: PRT
<213> ORGANISM: Chrysosporium lucknowense

<400> SEQUENCE: 12

Met Gln Leu Pro Ala Ala Ala Gln Trp Leu Leu Thr Leu Pro Ala Lys
1               5                   10                  15

Ala Ser Leu Ala Asp Asn His Arg Gln Val His Gln Lys Pro Leu Ala
            20                  25                  30

Arg Ser Glu Pro Phe Tyr Pro Ser Pro Trp Met Asn Pro Asn Ala Asp
        35                  40                  45

Gly Trp Ala Glu Ala Tyr Ala Gln Ala Lys Ser Phe Val Ser Gln Met
    50                  55                  60

```
Thr Leu Leu Glu Lys Val Asn Leu Thr Thr Gly Val Gly Trp Gly Ala
 65                  70                  75                  80

Glu Gln Cys Val Gly Gln Val Gly Ala Ile Pro Arg Leu Gly Leu Arg
                 85                  90                  95

Ser Leu Cys Met His Asp Ser Pro Leu Gly Ile Arg Gly Ala Asp Tyr
            100                 105                 110

Asn Ser Ala Phe Pro Ser Gly Gln Thr Val Ala Ala Thr Trp Asp Arg
        115                 120                 125

Gly Leu Met Tyr Arg Arg Gly Tyr Ala Met Gly Gln Glu Ala Lys Gly
    130                 135                 140

Lys Gly Ile Asn Val Leu Leu Gly Pro Val Ala Gly Pro Leu Gly Arg
145                 150                 155                 160

Met Pro Glu Gly Gly Arg Asn Trp Glu Gly Phe Ala Pro Asp Pro Val
                165                 170                 175

Leu Thr Gly Ile Gly Met Ser Glu Thr Ile Lys Gly Ile Gln Asp Ala
            180                 185                 190

Gly Val Ile Ala Cys Ala Lys His Phe Ile Gly Asn Glu Gln Glu His
        195                 200                 205

Phe Arg Gln Val Pro Glu Ala Gln Gly Tyr Gly Tyr Asn Ile Ser Glu
    210                 215                 220

Thr Leu Ser Ser Asn Ile Asp Asp Lys Thr Met His Glu Leu Tyr Leu
225                 230                 235                 240

Trp Pro Phe Ala Asp Ala Val Arg Ala Gly Val Gly Ser Val Met Cys
                245                 250                 255

Ser Tyr Gln Gln Val Asn Asn Ser Tyr Ala Cys Gln Asn Ser Lys Leu
            260                 265                 270

Leu Asn Asp Leu Leu Lys Asn Glu Leu Gly Phe Gln Gly Phe Val Met
        275                 280                 285

Ser Asp Trp Gln Ala Gln His Thr Gly Ala Ala Ser Ala Val Ala Gly
    290                 295                 300

Leu Asp Met Ser Met Pro Gly Asp Thr Gln Phe Asn Thr Gly Val Ser
305                 310                 315                 320

Phe Trp Gly Ala Asn Leu Thr Leu Ala Val Leu Asn Gly Thr Val Pro
                325                 330                 335

Ala Tyr Arg Leu Asp Asp Met Ala Met Arg Ile Met Ala Ala Leu Phe
            340                 345                 350

Lys Val Thr Lys Thr Thr His Leu Glu Pro Ile Asn Phe Ser Phe Trp
        355                 360                 365

Thr Asp Asp Thr Tyr Gly Pro Ile His Trp Ala Ala Lys His Gly Tyr
    370                 375                 380

Gln Lys Ile Asn Ser His Val Asp Val Arg Ala Asp His Gly Asn Leu
385                 390                 395                 400

Ile Arg Glu Ile Ala Ala Lys Gly Thr Val Leu Leu Lys Asn Thr Gly
                405                 410                 415

Ser Leu Pro Leu Asn Lys Pro Lys Phe Val Ala Val Ile Gly Glu Asp
            420                 425                 430

Ala Gly Ser Ser Pro Asn Gly Pro Asn Gly Cys Ser Asp Arg Gly Cys
        435                 440                 445

Asn Glu Gly Thr Leu Ala Met Gly Trp Gly Ser Gly Thr Ala Asn Tyr
    450                 455                 460

Pro Tyr Leu Val Ser Pro Asp Ala Ala Leu Gln Ala Arg Ala Ile Gln
465                 470                 475                 480
```

```
Asp Gly Thr Arg Tyr Glu Ser Val Leu Ser Asn Tyr Ala Glu Glu Lys
                485                 490                 495

Thr Lys Ala Leu Val Ser Gln Ala Asn Ala Thr Ala Ile Val Phe Val
        500                 505                 510

Asn Ala Asp Ser Gly Glu Gly Tyr Ile Asn Val Asp Gly Asn Glu Gly
            515                 520                 525

Asp Arg Lys Asn Leu Thr Leu Trp Asn Asn Gly Asp Thr Leu Val Lys
        530                 535                 540

Asn Val Ser Ser Trp Cys Ser Asn Thr Ile Val Ile His Ser Val
545                 550                 555                 560

Gly Pro Val Leu Leu Thr Asp Trp Tyr Asp Asn Pro Asn Ile Thr Ala
                565                 570                 575

Ile Leu Trp Ala Gly Leu Pro Gly Gln Glu Ser Gly Asn Ser Ile Thr
            580                 585                 590

Asp Val Leu Tyr Gly Lys Val Asn Pro Ala Ala Arg Ser Pro Phe Thr
        595                 600                 605

Trp Gly Lys Thr Arg Glu Ser Tyr Gly Ala Asp Val Leu Tyr Lys Pro
    610                 615                 620

Asn Asn Gly Asn Gly Ala Pro Gln Gln Asp Phe Thr Glu Gly Val Phe
625                 630                 635                 640

Ile Asp Tyr Arg Tyr Phe Asp Lys Val Asp Asp Ser Val Ile Tyr
                645                 650                 655

Glu Phe Gly His Gly Leu Ser Tyr Thr Thr Phe Glu Tyr Ser Asn Ile
            660                 665                 670

Arg Val Val Lys Ser Asn Val Ser Glu Tyr Arg Pro Thr Thr Gly Thr
        675                 680                 685

Thr Ala Gln Ala Pro Thr Phe Gly Asn Phe Ser Thr Asp Leu Glu Asp
    690                 695                 700

Tyr Leu Phe Pro Lys Asp Glu Phe Pro Tyr Ile Tyr Gln Tyr Ile Tyr
705                 710                 715                 720

Pro Tyr Leu Asn Thr Thr Asp Pro Arg Arg Ala Ser Ala Asp Pro His
                725                 730                 735

Tyr Gly Gln Thr Ala Glu Glu Phe Leu Pro Pro His Ala Thr Asp Asp
            740                 745                 750

Asp Pro Gln Pro Leu Leu Arg Ser Gly Gly Asn Ser Pro Gly Gly
        755                 760                 765

Asn Arg Gln Leu Tyr Asp Ile Val Tyr Thr Ile Thr Ala Asp Ile Thr
    770                 775                 780

Asn Thr Gly Ser Val Val Gly Glu Glu Val Pro Gln Leu Tyr Val Ser
785                 790                 795                 800

Leu Gly Gly Pro Glu Asp Pro Lys Val Gln Leu Arg Asp Phe Asp Arg
                805                 810                 815

Met Arg Ile Glu Pro Gly Glu Thr Arg Gln Phe Thr Gly Arg Leu Thr
            820                 825                 830

Arg Arg Asp Leu Ser Asn Trp Asp Val Thr Val Gln Asp Trp Val Ile
        835                 840                 845

Ser Arg Tyr Pro Lys Thr Ala Tyr Val Gly Arg Ser Ser Arg Lys Leu
    850                 855                 860

Asp Leu Lys Ile Glu Leu Pro
865                 870

<210> SEQ ID NO 13
<211> LENGTH: 995
<212> TYPE: DNA
```

```
<213> ORGANISM: Chrysosporium lucknowense
<220> FEATURE:
<221> NAME/KEY: CDS
<222> LOCATION: (1)..(432)
<220> FEATURE:
<221> NAME/KEY: CDS
<222> LOCATION: (542)..(572)
<220> FEATURE:
<221> NAME/KEY: CDS
<222> LOCATION: (680)..(806)
<220> FEATURE:
<221> NAME/KEY: CDS
<222> LOCATION: (908)..(992)

<400> SEQUENCE: 13
```

| | | | | | | | | | | | | | | | | |
|---|---|---|

-continued

```
                                             Phe Gln Asn Ala
                                                 200
gac aac ccg tcg gtc acc ttc cag gag gtg gcc tgc ccg tcg gag ctc      968
Asp Asn Pro Ser Val Thr Phe Gln Glu Val Ala Cys Pro Ser Glu Leu
            205                 210                 215
acg tcc aag agc ggc tgc tcc cgt taa                                  995
Thr Ser Lys Ser Gly Cys Ser Arg
        220                 225

<210> SEQ ID NO 14
<211> LENGTH: 225
<212> TYPE: PRT
<213> ORGANISM: Chrysosporium lucknowense

<400> SEQUENCE: 14

Met His Leu Ser Ala Thr Thr Gly Phe Leu Ala Leu Pro Ala Leu Ala
1               5                   10                  15

Leu Ala Gln Leu Ser Gly Ser Gly Gln Thr Thr Arg Tyr Trp Asp Cys
            20                  25                  30

Cys Lys Pro Ser Cys Ala Trp Pro Gly Lys Gly Pro Ser Ser Pro Val
        35                  40                  45

Gln Ala Cys Asp Lys Asn Asp Asn Pro Leu Asn Asp Gly Gly Ser Thr
    50                  55                  60

Arg Ser Gly Cys Asp Ala Gly Gly Ser Ala Tyr Met Cys Ser Ser Gln
65                  70                  75                  80

Ser Pro Trp Ala Val Ser Asp Glu Leu Ser Tyr Gly Trp Ala Ala Val
                85                  90                  95

Lys Leu Ala Gly Ser Ser Glu Ser Gln Trp Cys Cys Ala Cys Tyr Glu
            100                 105                 110

Leu Thr Phe Thr Ser Gly Pro Val Ala Gly Lys Lys Met Ile Val Gln
        115                 120                 125

Ala Thr Asn Thr Gly Gly Asp Leu Gly Asp Asn His Phe Asp Leu Ala
    130                 135                 140

Ile Pro Gly Gly Gly Val Gly Ile Phe Asn Ala Cys Thr Asp Gln Tyr
145                 150                 155                 160

Gly Ala Pro Pro Asn Gly Trp Gly Asp Arg Tyr Gly Gly Ile His Ser
                165                 170                 175

Lys Glu Glu Cys Glu Ser Phe Pro Glu Ala Leu Lys Pro Gly Cys Asn
            180                 185                 190

Trp Arg Phe Asp Trp Phe Gln Asn Ala Asp Asn Pro Ser Val Thr Phe
        195                 200                 205

Gln Glu Val Ala Cys Pro Ser Glu Leu Thr Ser Lys Ser Gly Cys Ser
    210                 215                 220

Arg
225

<210> SEQ ID NO 15
<211> LENGTH: 4190
<212> TYPE: DNA
<213> ORGANISM: Chrysosporium lucknowense
<400> SEQUENCE: 15
gcgcttccgg cctgggcgag taaaatgacg gaagccgggc cccgtccgac tgcgtttgtc      60
ccaactcgga agcaggcatc gtttttgggg cgggaggaag cgttgcaaca cgcactatcg     120
ccaaggtgga ctcggcgcaa tctggaggtt cggcccgcgg aggacggaat ccgggctgaa     180
tctgcgcaaa ggctgaccct gcgatggtgg gaaaatgtaa atatgtgaag ttataggcat     240
```

```
ataggactca gcgatgacat ggaaattgca gaggcatgtg ggatttcagc gtttggcatg      300
cattggtcgg atctctcgcc ttgtctgatg tgatcccgcc ggaggtgttt cggtctctgg      360
ggaagggacc cccctggcc ccccacctgc cccgcatcat gcctcgccac gactcccgcg       420
cgccgaggaa gaacttcggg tctttgtgac gggagattcc actgagtgag cattggccaa     480
ccaagcacac aattactccg tacatacaca gtacttctga ctccgtaaag taaaccgtgt     540
gtttcaaaga tcggtaatcc gtaacaggta ctccgtatct aaggtaaatt taccctgtgc     600
acggagcaga acctgaactt cttccccct cttactcgag tagtcaccct actccaacca      660
gcggcttttc aactcgcaaa gtcttgttta taacagtgca tatacctgca tttcgtatct    720
cgctagtgta aagacgacca cacgcggaca agaaagaaa atccaattg cccgatggct       780 cttagtttga ggacagcagc gaaggactac actgcgccgt agtgaccagg ccaagaaacg     840
cgaatcgtat attaacggca aatcaaaatg gattatatgc catttcgctt ccggggttgcg    900 tgctcgtccg aagtctggtg ccgatcgatt gcgaaccccc ggaatcgcgg gatgattcct    960
acagccgccg aaaggggggg ggggggaggg gggtctggac gggacgtgca taacttcgaa    1020
tttctagaat attgcggatt gggttccctt cagccctgcg agcgcgcccc cttctggaac    1080
cgcacccttc accggttcca cacacagagg acatgggtgg aaatgtgtac ctgacggttg    1140
cccctttggg acagtggaga ggcggatgtt cggataacca tccggagccg cagtgtcgac    1200
caagatcttg gcttaccatc gacaccaaca tgcggactcg tccctcagtc atggagcctt    1260
ggctcgcgga gcctccgttc gaagcggcta tcccgtcctg ccagcggagg atctcgtacc    1320
gcttccgcga actgtgaatg tcctgggtat aagagcatgg cgcgaccttg tctcgtcagg    1380
aacggggagg aggagggctt ggttagggtc gcgttcgttt ggagattgct gagctctgag    1440
ccttcggtcc ttggatccct gcggtccccg gtctcctctc tctctctctc tctctctctc   1500
tctctctctt cttcccacgc tcgttcgaca gacgcctccc cttcttcgct ctcctttccc   1560
tcgcacgtag cacactaata gtgcaccatg cgcgtctcta gtttggtcgc ggcccttgct    1620
accggtggtc ttgtcgccgc cacgcctaag cccaaggggt cgtcgccccc tggggccgtg    1680
gacgcgaacc ctttcaaggg caagacgcag ttcgtcaacc cggcatgggc ggccaagctg   1740
gaacagacca aaaaggcgtt cctggccagg aacgacaccg tcaatgccgc caagacggag   1800
aaggtccagc agaccagctc gttcgtctgg gtctcgagga tcgccgagct ctccaacatc   1860
gacgacgcca tcgcggctgc ccgcaaggcg cagaagaaga cgggcaggag gcagatcgtc    1920
ggcctggtgc tctacaacct tccggaccgc gactgcagcg cgggcgagag cgcgggcgag    1980
ctcagcagcg acaagaacgg gctcgagatc tacaagactg agttcgtcaa gcccttcgcc    2040
gacaaggtgg cggccgcaaa ggacctcgac ttcgccatcg tcctggagcc cgactcgctg    2100
gccaacctgg tcaccaacct gggcatcgag ttctgcgcca acgccgcccc cgtctaccgc    2160
gagggcatcg cctatgccat ctccagcctt cagcagccaa acgtgcactt gtacatcgat    2220
gctgcccacg gcggctggct cggctgggac gacaacctgc cgctggccgc caaggagttt    2280
gccgaggtgg tcaagcttgc cggcgagggc aagaagatcc gcggcttcgt caccaacgtg    2340
tccaactaca accccttcca cgccgtcgtg cgcgagaact ttaccgagtg gagcaactcg    2400
tgggacgagt ctcactacgc ctcctcgctc acaccgttcc tcgagaaaga ggggctgccg    2460
gcacgcttca tcgtcgacca gggtcgcgtt ccctcccgg gagcccgcaa ggagtggtga    2520
gtttcgacca gattgaccct cgacccatgc gaccgagatt gctgacgatt gaattgcgtg    2580
```

-continued

```
tcccgtcccc caggggtgaa tggtgcaacg tggcacccgc cggatttggc cccgcgccca   2640
cgaccagggt caacaacacc gtcgtcgatg ctctcgtctg ggtcaagcct ggcggcgaga   2700
gcgacggcga gtgtggcttg gctggcgccc ccaaggccgg ccagtggttc gacgagtacg   2760
cccagatgct ggtcgagaat gcccacccgt ctgtcgtcca caagtggtag ataaattttg   2820
gagtccgaga agggtcccag atagactttt gttttaaaac aaaatgcaag gtgtcgacag   2880
atactggctt aacattaacc aagcaccatg aacatgactt gtcaacatat tgatacattc   2940
cgctgctttc ccatacgtgc tctcaggtct cagggatcaa atggataggt cggtaatgca   3000
aaacgatcca ttggatatcc agaagagaga aaaaaaaaag gacatgcatg ccttgtctgt   3060
catcatgagg aaacaaagga aaaacaaacg atcgtcgtgt tccaacaagc tttccaagac   3120
cacaagaccc atccaccaac acaaccaaac gacaagcaat acgatggacc gccgttgttc   3180
catctctcaa gagctgacta aacgaacagt cgttgaaatc atcctacatg agtacgccgc   3240
accacctgtt atcgtgtaaa ccaaatcgcc tgttaaagtg catcatctct taggtatgat   3300
cgtaagttcc ggtcacggtc acggatcagg gatggttctc aattcgtgtg tcgcgtagcc   3360
gccgccgtat ctggacaaga cttcttgtat tgctccgaaa ccgcttttgc cgccctaata   3420
atctgtagcc ttcttacctg gtggtgcctt gaaagacgcg gcaggcaaca cttcgcaggt   3480
ctgtggcgca ccagcaccag gctgtggtga tgccccggaa ccggtcgtcg acttgctcgc   3540
ggtgtcctcg gctggtgggg atgggggtga tgagggcttg gagggtgttg ttgcgcccgc   3600
aacatccggc tccggctccg gaccgtccac agacattgga cctgcgagca tgactcgtgc   3660
cttcagccag accaaagcca tgccatcatc gcctctgccg acgctgttga gcgggaggct   3720
gatgttctca gccagaactg cgggctgtac ggccatgacc atgggctgtt cggtctggcc   3780
gtcttgcggc ggtttctccc tgccagcttg ttgtgcgcgg tgcctgcgag attcgacttc   3840
gacctgggcg tggcagaggg tgacgaggga cgttgacgcc ttgatctcct tgctccccat   3900
gtccttccac ccgtacaggc ggacgggtgc catacgcgtc cacagcctgc acgagaacct   3960
cagggcgtcg tcaatgagtt ctgtcaactt gctctccagc ctctctatgc cgcgagcatc   4020
ctgatcctgg agcagaaacc gtgccgagcc tccgaggaaa cgctccttca gcttccgcgc   4080
gtagtttagg cgtgattcaa caaacgtccg gcgggactcg ttgttgcccg cagcagcgac   4140
gtccttgatg ctgaagccgc cgtcggcgaa caggcgcatc atctgggccc              4190
```

```

<210> SEQ ID NO 16
<211> LENGTH: 381
<212> TYPE: PRT
<213> ORGANISM: Chrysosporium lucknowense

<400> SEQUENCE: 16

Met Arg Val Ser Ser Leu Val Ala Ala Leu Ala Thr Gly Gly Leu Val
1               5                   10                  15

Ala Ala Thr Pro Lys Pro Lys Gly Ser Ser Pro Pro Gly Ala Val Asp
            20                  25                  30

Ala Asn Pro Phe Lys Gly Lys Thr Gln Phe Val Asn Pro Ala Trp Ala
        35                  40                  45

Ala Lys Leu Glu Gln Thr Lys Lys Ala Phe Leu Ala Arg Asn Asp Thr
    50                  55                  60

Val Asn Ala Ala Lys Thr Glu Lys Val Gln Gln Thr Ser Ser Phe Val
65                  70                  75                  80

Trp Val Ser Arg Ile Ala Glu Leu Ser Asn Ile Asp Asp Ala Ile Ala
                85                  90                  95
```

```
Ala Ala Arg Lys Ala Gln Lys Lys Thr Gly Arg Arg Gln Ile Val Gly
            100                 105                 110

Leu Val Leu Tyr Asn Leu Pro Asp Arg Asp Cys Ser Ala Gly Glu Ser
        115                 120                 125

Ala Gly Glu Leu Ser Ser Asp Lys Asn Gly Leu Glu Ile Tyr Lys Thr
    130                 135                 140

Glu Phe Val Lys Pro Phe Ala Asp Lys Val Ala Ala Ala Lys Asp Leu
145                 150                 155                 160

Asp Phe Ala Ile Val Leu Glu Pro Asp Ser Leu Ala Asn Leu Val Thr
                165                 170                 175

Asn Leu Gly Ile Glu Phe Cys Ala Asn Ala Ala Pro Val Tyr Arg Glu
            180                 185                 190

Gly Ile Ala Tyr Ala Ile Ser Ser Leu Gln Gln Pro Asn Val His Leu
        195                 200                 205

Tyr Ile Asp Ala Ala His Gly Gly Trp Leu Gly Trp Asp Asp Asn Leu
    210                 215                 220

Pro Leu Ala Ala Lys Glu Phe Ala Glu Val Val Lys Leu Ala Gly Glu
225                 230                 235                 240

Gly Lys Lys Ile Arg Gly Phe Val Thr Asn Val Ser Asn Tyr Asn Pro
                245                 250                 255

Phe His Ala Val Val Arg Glu Asn Phe Thr Glu Trp Ser Asn Ser Trp
            260                 265                 270

Asp Glu Ser His Tyr Ala Ser Ser Leu Thr Pro Phe Leu Glu Lys Glu
        275                 280                 285

Gly Leu Pro Ala Arg Phe Ile Val Asp Gln Gly Arg Val Ala Leu Pro
    290                 295                 300

Gly Ala Arg Lys Glu Trp Gly Glu Trp Cys Asn Val Ala Pro Ala Gly
305                 310                 315                 320

Phe Gly Pro Ala Pro Thr Thr Arg Val Asn Asn Thr Val Val Asp Ala
                325                 330                 335

Leu Val Trp Val Lys Pro Gly Gly Glu Ser Asp Gly Glu Cys Gly Leu
            340                 345                 350

Ala Gly Ala Pro Lys Ala Gly Gln Trp Phe Asp Glu Tyr Ala Gln Met
        355                 360                 365

Leu Val Glu Asn Ala His Pro Ser Val Val His Lys Trp
    370                 375                 380
```

<210> SEQ ID NO 17
<211> LENGTH: 3000
<212> TYPE: DNA
<213> ORGANISM: Chrysosporium lucknowense

<400> SEQUENCE: 17

```
cgcggccccg tctttgaacg cttgagaagc gcacggtgaa gaaccatcaa ctccgattcc      60
gctcctcatc ctcccacgaa gccgattgaa atagccacag cggctatgta cggattactc     120
tgctccgttt gcacatccat acacagcgct atttttaaaa gttcaggacg gccaagcccg     180
gttcttggaa cggacgaccc ggattccgaa agctccagcg ctcaatgcgg tcagtcgtgg     240
cgctgatcct gctgatctgc tgatctcata aacccgcaac ttcaactttt cactttgaag     300
cgtatacacg cagcgcctct ttcaccggcg cattcatact cgcaaattaa ccgctaatat     360
cctcgcactt ggataatgtg tagccgacac ggaggagggg ggttgggggg gggttggggg     420
gagacatgat ggtctgccca acggatatta ttattttgtt gttttgtata attactgcgg     480
```

```
caacattctc aaaggggccg tgcctcgcgg cgggaaagcc catgacagag aattggacag      540
ctccaagctc gcgatatact ctaacaacgg cgtgactcgg caatgaaggc ctgccgctcg      600
agtgataggg cgaagtaaaa cggacgttac atgcggcact tagccggctg atgccggaga      660
atacgggatt caacgataca atcacacgat gcgacacacc tcggcgactt ggcgctctat      720
ggaagaaggc tgggttaaag ctggcgtaga ttttgcgcgt cttggtttct taaccgggtt      780
atttctattt ctcatatgcc gcgagcgaat gcggggtgca gagcgccgg gagtcgatgg       840 tcctatcaga caagagcctg gccccggaac ctgggataat agaagccaaa ttaagccatg      900
ggagtatcgt ccgggggtag gaaccgcacg ggcaactaga ggaggaagaa tttggtataa      960
agggaggacg gcggaacagg cttgatggac atgaatcaga agacgacact gggcaactaa     1020
acagcttgca gcagagtttt gtgccttgca taggccctcg atatcatggt ctcgttcact     1080
ctcctcctca cggtcatcgc cgctgcggtg acgacggcca gccctctcga ggtggtcaag     1140
cgcggcatcc agccgggcac gggcacccac gaggggtact tctactcgtt ctggaccgac     1200
ggccgtggct cggtcgactt caaccccggg ccccgcggct cgtacagcgt cacctggaac     1260
aacgtcaaca actgggttgg cggcaagggc tggaacccgg gccgccgcg caagattgcg       1320 tacaacggca cctggaacaa ctacaacgtg aacagctgtg cgttgtcctc ctctttctcc     1380
ctttcgcttg ttttccttga tgattgggat ccattttaaa agagaaggaa aaaaaaaca       1440 aaggaaaata gaagataact aacgccaagc tctggcagac ctcgccctgt acggctggac     1500
tcgcaacccg ctggtcgagt attacatcgt ggaggcatac ggcacgtaca acccctcgtc     1560
gggcacggcg cggctgggca ccatcgagga cgacggcggc gtgtacgaca tctacaagac     1620
gacgcggtac aaccagccgt ccatcgaggg gacctccacc ttcgaccagt actggtccgt     1680
ccgccgccag aagcgcgtcg gcggcactat cgacacgggc aagcactttg acgagtggaa     1740
gcgccagggc aacctccagc tcggcacctg gaactacatg atcatggcca ccgagggcta     1800
ccagagctct ggttcggcca ctatcgaggt ccggaggcc taaagaagcc aggcgccttt       1860
cttttgtttt gcaggagggg gtagaggggg gggggaggg aaaacgaaaa gtagcagggt       1920
ggttttatgc cggcagccgt gggccattcg agtgcaacct gtatctctct ctctcccaag     1980
tctccgggct ccttctcaga gaacttcaat atgtctgggg acaaaccacc ttgtgaaata     2040
caacggtaat tatctaagtt tgagtgccct atcgtatgct tctgaaaatt tcctgctcct     2100
tgatacaagt cggtttgagc cgagccaatg agactgtgtc gattgataga ggccctgaag     2160
gatcaagcgc gatgcaacaa ttaagcatga ctacgtgcct agctgcagat aaatggaagc     2220
cactcaccaa ggtcaacccc gcatactggc acgtaagaac cttccgtgta caaggcccaa     2280
ccgactcaca tatctatctg cttgggtttt gggatgcggt tttttaccca caaacaaat      2340 ttgatacaat gctctgctgt gcccgggttg ctgagaccaa gccgtaatca gcgggcaggg     2400
aatcgagtag gtcacgcctg ttgcttggtc tagaacaaac taatattaaa aagcttgtg      2460 ctcggcacac atacagaact cgacctgagg catgttcttg gaaggcggct agccagtcaa     2520
gtctggcacc aggccttggt ctcgtcgagg ataccgaggg cgaggaggat gaggaagacc     2580
tctttctcgc ctcagatctc ttaggggacg aagaagacaa cgccggagcc acacaataat     2640
taggtctcat atcagacgtt tcggcctggc cgagctaata tgtctaatta tgcccatcag     2700
ccgtatgtcg aggcaggttg caccgatacg ctcgccgcgc cgcctcattc atctccgact     2760
gggcacaatg tcgccatctc ggccgtcaag gtggtgcaag atacctatta tgcaagcaga     2820
ggatcagatg gcgggccgat acgagcggct gctccggctt gcgagaaagc cgcttcgcag     2880
```

```
caaggtatcg tggcaggccg ccatttccgg ttgggtattc tttgtcttgt ttgcttcgta    2940
attatgtcct ggctggcatt gtgggaaggg gcgaacctct tgatttccga tgggggtcga    3000
```

<210> SEQ ID NO 18
<211> LENGTH: 218
<212> TYPE: PRT
<213> ORGANISM: Chrysosporium lucknowense

<400> SEQUENCE: 18

```
Met Val Ser Phe Thr Leu Leu Leu Thr Val Ile Ala Ala Ala Val Thr
1               5                   10                  15

Thr Ala Ser Pro Leu Glu Val Val Lys Arg Gly Ile Gln Pro Gly Thr
            20                  25                  30

Gly Thr His Glu Gly Tyr Phe Tyr Ser Phe Trp Thr Asp Gly Arg Gly
        35                  40                  45

Ser Val Asp Phe Asn Pro Gly Pro Arg Gly Ser Tyr Ser Val Thr Trp
    50                  55                  60

Asn Asn Val Asn Asn Trp Val Gly Gly Lys Gly Trp Asn Pro Gly Pro
65                  70                  75                  80

Pro Arg Lys Ile Ala Tyr Asn Gly Thr Trp Asn Asn Tyr Asn Val Asn
                85                  90                  95

Ser Tyr Leu Ala Leu Tyr Gly Trp Thr Arg Asn Pro Leu Val Glu Tyr
            100                 105                 110

Tyr Ile Val Glu Ala Tyr Gly Thr Tyr Asn Pro Ser Ser Gly Thr Ala
        115                 120                 125

Arg Leu Gly Thr Ile Glu Asp Asp Gly Gly Val Tyr Asp Ile Tyr Lys
    130                 135                 140

Thr Thr Arg Tyr Asn Gln Pro Ser Ile Glu Gly Thr Ser Thr Phe Asp
145                 150                 155                 160

Gln Tyr Trp Ser Val Arg Arg Gln Lys Arg Val Gly Gly Thr Ile Asp
                165                 170                 175

Thr Gly Lys His Phe Asp Glu Trp Lys Arg Gln Gly Asn Leu Gln Leu
            180                 185                 190

Gly Thr Trp Asn Tyr Met Ile Met Ala Thr Glu Gly Tyr Gln Ser Ser
        195                 200                 205

Gly Ser Ala Thr Ile Glu Val Arg Glu Ala
    210                 215
```

<210> SEQ ID NO 19
<211> LENGTH: 10
<212> TYPE: PRT
<213> ORGANISM: Chrysosporium lucknowense

<400> SEQUENCE: 19

```
His Glu Tyr Gly Thr Asn Ile Gly Ser Arg
1               5                   10
```

<210> SEQ ID NO 20
<211> LENGTH: 10
<212> TYPE: PRT
<213> ORGANISM: Humicola grisea

<400> SEQUENCE: 20

```
His Glu Tyr Gly Thr Asn Ile Gly Ser Arg
1               5                   10
```

<210> SEQ ID NO 21

<211> LENGTH: 17
<212> TYPE: PRT
<213> ORGANISM: Chrysosporium lucknowense

<400> SEQUENCE: 21

Met Gly Asn Gln Asp Phe Tyr Gly Pro Gly Leu Thr Val Asp Thr Ser
1 5 10 15

Lys

<210> SEQ ID NO 22
<211> LENGTH: 15
<212> TYPE: PRT
<213> ORGANISM: Aspergillus niger

<400> SEQUENCE: 22

Leu Gly Asn Thr Asp Phe Tyr Gly Pro Gly Leu Thr Val Asp Thr
1 5 10 15

<210> SEQ ID NO 23
<211> LENGTH: 8
<212> TYPE: PRT
<213> ORGANISM: Chrysosporium lucknowense

<400> SEQUENCE: 23

Leu Phe Ala Asn Asp Tyr Tyr Arg
1 5

<210> SEQ ID NO 24
<211> LENGTH: 8
<212> TYPE: PRT
<213> ORGANISM: Humicola insolens

<400> SEQUENCE: 24

Leu Trp Ala Asn Asn Tyr Tyr Arg
1 5

<210> SEQ ID NO 25
<211> LENGTH: 18
<212> TYPE: PRT
<213> ORGANISM: Chrysosporium lucknowense

<400> SEQUENCE: 25

His Tyr Ile Glu Ala Phe Ser Pro Leu Leu Asn Ser Ala Gly Phe Pro
1 5 10 15

Ala Arg

<210> SEQ ID NO 26
<211> LENGTH: 17
<212> TYPE: PRT
<213> ORGANISM: Neurospora crassa

<400> SEQUENCE: 26

Lys Tyr Ile Glu Ala Phe Ser Pro Leu Leu Asn Ala Ala Gly Phe Pro
1 5 10 15

Ala

<210> SEQ ID NO 27
<211> LENGTH: 18
<212> TYPE: PRT
<213> ORGANISM: Chrysosporium lucknowense

```
<400> SEQUENCE: 27

Asn Gly Lys Gln Pro Thr Gly Gln Gln Gln Trp Gly Asp Trp Cys Asn
1               5                   10                  15

Val Lys

<210> SEQ ID NO 28
<211> LENGTH: 17
<212> TYPE: PRT
<213> ORGANISM: Trichoderma reesei

<400> SEQUENCE: 28

Ser Gly Lys Gln Pro Thr Gly Gln Gln Gln Trp Gly Asp Trp Cys Asn
1               5                   10                  15

Val
```